(12) United States Patent
Ono et al.

(10) Patent No.: US 9,932,396 B2
(45) Date of Patent: Apr. 3, 2018

(54) ANTIBODY AGAINST HUMAN NRG1 PROTEIN

(71) Applicant: MEDICAL & BIOLOGICAL LABORATORIES CO., LTD., Nagoya-shi, Aichi (JP)

(72) Inventors: Kenichiro Ono, Nagoya (JP); Kasumi Yagi, Tokyo (JP)

(73) Assignee: MEDICAL & BIOLOGICAL LABORATORIES CO., LTD., Nagoya-shi, Aichi (JP)

( * ) Notice: Subject to any disclaimer, the term of this patent is extended or adjusted under 35 U.S.C. 154(b) by 0 days.

(21) Appl. No.: 14/765,581

(22) PCT Filed: Feb. 7, 2014

(86) PCT No.: PCT/JP2014/052939
§ 371 (c)(1),
(2) Date: Oct. 13, 2015

(87) PCT Pub. No.: WO2014/123227
PCT Pub. Date: Aug. 14, 2014

(65) Prior Publication Data
US 2016/0046706 A1 Feb. 18, 2016

(30) Foreign Application Priority Data
Feb. 8, 2013 (JP) ................. 2013-023125

(51) Int. Cl.
*C07K 16/22* (2006.01)
*A61K 39/00* (2006.01)
(52) U.S. Cl.
CPC ........ *C07K 16/22* (2013.01); *A61K 2039/505* (2013.01); *C07K 2317/24* (2013.01); *C07K 2317/33* (2013.01); *C07K 2317/34* (2013.01); *C07K 2317/73* (2013.01); *C07K 2317/76* (2013.01)

(58) Field of Classification Search
None
See application file for complete search history.

(56) References Cited

FOREIGN PATENT DOCUMENTS

WO       2010/127181 A1    11/2010
WO  WO 2002/051870     *   7/2012
WO       2013/025853 A1    2/2013

OTHER PUBLICATIONS

Leung et al., British Journal of Urology, 79:212-216, 1997.*
Rajpal et al., PNAS, 102(24):8466-8471, 2005.*
Dubreuil et al., Journal of Biological Chemistry, 280(26): 24880-24887, 2005.*
Sela-Culang et al., Frontiers in Immunology, vol. 4, Article 302, Oct. 2013, doi: 10.3389/fimmu.2013.00302.*
Extended European Search Report dated Oct. 10, 2016, issued from the European Patent Office in corresponding European application No. 14748891.0.*

Radhika Srinivasan, et al., "Expression of the c-erb B-3/HER-3 and c-erbB-4/HER-4 Growth Factor Receptors and Their Ligands, Neuregulin-1 α, Neuregulin-1 β, and Betacellulin, in Normal Endometrium and Endometrial Cancer", Clinical Cancer Research, Oct. 1999, pp. 2877-2883, vol. 5, No. 10.
Mai M. Hijazi, et al., "Heregulin regulates the actin cytoskeleton and promotes invasive properties in breast cancer cell lines", International Journal of Oncology, 2000, pp. 629-641, vol. 17, No. 4.
William E. Holmes, et al., "Identification of Heregulin, a Specific Activator of p185$^{erB2}$", Science, 1992, pp. 1205-1210, vol. 256.
Sen-Yung Hsieh, et al., "Neuregulin/Erythroblastic Leukemia Viral Oncogene Homolog 3 Autocrine Loop Contributes to Invasion and Early Recurrence of Human Hepatoma", Hepatology, 2011, pp. 504-516, vol. 53, No. 2.
Andreas Martin Herrlich, et al., "Heregulin, a necessary intermediate in osmotic stress-induced AQP5 expression.", FASEB Journal, Annual Meeting of the Professional Research Scientists on Experimental Biology, 2002, p. A56, vol. 16, No. 4.
Duanzhi Wen, et al., "Structural and Functional Aspects of the Multiplicity of Neu Differentiation Factors", Molecular and Cellular Biology, Mar. 1994, pp. 1909-1919, vol. 14, No. 3.
Jeffrey A. Loeb, et al., "The Neuregulin Precursor proARIA Is Processed to ARIA after Expression on the Cell Surface by a Protein Kinase C-Enhanced Mechanism", Molecular and Cellular Neuroscience, 1998, vol. 11, pp. 77-91.
Juan Carlos Montero, et al., "Differential Shedding of Transmembrane Neuregulin Isoforms by the Tumor Necrosis Factor-α-Converting Enzyme", Molecular and Cellular Neuroscience, 2000, pp. 631-648, vol. 16.
Kyoko Shirakabe, et al., "Roles of Meltrin β/ADAM19 in the Processing of Neuregulin", The Journal of Biological Chemistry, Mar. 23, 2001, pp. 9352-9358, vol. 276, No. 12.
Juan Carlos Montero, "Mitogen-activated protein kinase-dependent and -independent routes control shedding of transmembrane growth factors through multiple secretases", Biochem. J., 2002, pp. 211-221, vol. 363.
Claudia Rosenbaum, et al., "Schwann Cells Express NDF and SMDF/n-ARIA mRNAs, Secrete Neuregulin, and Show Constitutive Activation of erbB3 Receptors: Evidence for a Neuregulin Autocrine Loop", Experimental Neurology, 1997, pp. 604-615, vol. 148.
Marlan R. Hansen, et al., "Constitutive Neuregulin-1/ErbB Signaling Contributes to Human Vestibular Schwannoma Proliferation", GLIA, 2006, pp. 593-600, vol. 53 (6).

(Continued)

*Primary Examiner* — Marianne P Allen
(74) *Attorney, Agent, or Firm* — Sughrue Mion, PLLC

(57) ABSTRACT

An object is to provide an antibody capable of specifically recognizing a human NRG1 protein isoform, and suppressing signal transduction in which the isoform is involved. An antibody capable of binding to a region at positions 221 to 234 of a human NRG1-α protein or an antibody capable of binding to a region at positions 213 to 239 of a human NRG1-β1 protein was successfully obtained. Further, it was also found that these antibodies had an activity of suppressing cleavage of the NRG1 protein, an activity of suppressing phosphorylation of an ErbB3 protein in a cancer cell, and an activity of suppressing in vivo tumor proliferation.

2 Claims, 26 Drawing Sheets

(56) References Cited

OTHER PUBLICATIONS

Phyllis L. Osheroff, et al., "Receptor Binding and Biological Activity of Mammalian Expressed Sensory and Motor Neuron-derived Factor (SMDF)", Growth Factors, 1999, pp. 241-253, vol. 16, No. 3.

Bernstein, et al., "Localization of neuregulin-1α (heregulin-α) and one of its receptors, ErbB-4 tyrosine kinase, in developing and adult human brain", Brain Research Bulletin, May 15, 2006, vol. 69, No. 5, pp. 546-559 (14 pages).

Lu, et al., "Studies on the Structure and Function of Glycosylated and Nonglycosylated neu Differentiation Factors: Similarities and Differences of The α and β Isoforms", The Journal of Biological Chemistry, Mar. 3, 1995, vol. 270, No. 9, pp. 4784-4791 (8 pages).

Gilmour, et al., "Neuregulin Expression, Function, and Signaling in Human Ovarian Cancer Cells", Clinical Cancer Research, Dec. 1, 2002, vol. 8, No. 12, pp. 3933-3942 (10 pages).

Edwards, et al., "Neuregulin 1 growth factors regulate proliferation but not apoptosis of a CNS neuronal progenitor cell line", Brain Research, Sep. 7, 2006, vol. 1108, No. 1, pp. 63-75 (14 pages).

Atlas, et al., "Heregulin Is Sufficient for the Promotion of Tumorigenicity and Metastasis of Breast Cancer Cells in Vivo", Molecular Cancer Research, Jan. 1, 2003, vol. 1, No. 3, pp. 165-175 (11 pages).

\* cited by examiner

ANTIBODY AGAINST HUMAN NRG1 PROTEIN

CROSS REFERENCE TO RELATED APPLICATIONS

This application is a National Stage of International Application No. PCT/JP2014/052939 filed Feb. 7, 2014, claiming priority based on Japanese Patent Application No. 2013-023125 filed Feb. 8, 2013, the contents of all of which are incorporated herein by reference in their entirety.

TECHNICAL FIELD

The present invention relates to an antibody against a human NRG1 protein. More specifically, the present invention relates to an antibody capable of specifically binding to any one of a human NRG1-α protein and a human NRG1-β1 protein, a DNA encoding the antibody, a hybridoma comprising any one of the antibody and the DNA, and a composition for treating or preventing a cancer, the composition comprising the antibody as an active ingredient.

BACKGROUND ART

NRG1 (neuregulin 1) is a member of the EGF family, and particularly soluble NRG1 binds to ErbB3 or ErbB4 and functions as a ligand of these receptors. Additionally, ErbB3 and ErbB4 are members of the EGF (epidermal growth factor) receptor family. It is also known that when soluble NRG1 binds to these receptors, the structures of the receptors change, forming homodimers or heterodimers. Further, such dimerization leads to phosphorylation of intracellular domains of these receptors. The phosphorylated intracellular domains further bind to signaling proteins, activating a variety of signal transduction events. Then, such NRG1-involved signal transduction regulates a series of biological reactions such as cell proliferation, cell differentiation, apoptosis, and cell migration, adhesion, and infiltration. More concretely, it has been revealed that NRG1 is involved in the growth and development of nervous systems and heart, as well as various cancers such as breast cancer, ovarian cancer, colorectal cancer, stomach cancer, lung cancer, thyroid cancer, gliomas, medulloblastoma, and melanoma.

Furthermore, soluble NRG1 is derived from a transmembrane precursor, like other factors belonging to the EGF family. To be more specific, it is believed that after produced as a transmembrane precursor (pro-NRG1), soluble NRG1 is transported to the cell surface (plasma membrane), and a cleavage enzyme such as metalloprotease cleaves (sheds) and re leases a membrane neighboring portion of an extracellular domain of the pro-NRG1. There is a report on the pro-NRG1 cleavage mechanism that the cleavage and release of pro-NRG1 by a protease at the cell surface are activated by a factor in a serum or PMA (phorbol-12-myristate-13-acetate): an activation factor for protein kinase C (PKC) (NPL 1). Further, two such proteases have been reported so far: TACE (tumor necrosis factor-α (TNFα) converting enzyme, ADAM17) and ADAM19 (meltrin β) (NPLs 2 and 3). It has been shown that PKC, Erk1/2, p38, and the like are involved in the mechanism of activating these proteases (NPL 4).

Meanwhile, nine NRG1 protein isoforms have been known. Among these, isoform 1 (NRG1-β1), isoform 2 (NRG1-α), isoform 3 (NRG1-β2), and the like are the aforementioned transmembrane precursors. Further, these isoforms are roughly classified into two types: α type (isoform 2) and β type (isoforms 1 and 3).

As described above, the NRG1-involved signal transduction regulates a variety of biological reactions. Hence, analyzing or controlling the signal transduction and the cleavage that would otherwise trigger the signaling for each isoform greatly contributes to the elucidation of a life phenomenon and eventually to the development of the medical field. In this regard, it is known generally that antibodies can be effective tools in specifically analyzing protein isoforms and controlling the functions thereof.

However, as shown in FIG. 1, α type and β type isoforms of the NRG1 protein substantially match for a portion from the N-terminus to an amino acid residue at position 212. The differences are just in a 10 amino-acid residue long C-terminal part of an EGF domain, and only approximately 20 amino acids of a juxtamembrane domain (which is a region located on the C-terminal side of the EGF domain and on the N-terminal side of the transmembrane sequence, and where the cleavage takes place). Further, the α type and β type isoforms match for the interval of six cysteine residues included in a C-terminal portion of the EGF domain. Thus, it is quite difficult to prepare an antibody capable of identifying such slight differences, so that an antibody capable of specifically recognizing these isoforms and also suppressing signal transduction in which these isoforms are involved has not been developed under current situations.

On the other hand, since it has been revealed that NRG1 is involved in various life phenomena as described above, antibodies against NRG1 have been developed, although the antibodies do not specifically bind to isoforms (NPLs 5 to 8).

For example, NPL 5 discloses that an anti-NRG1 antibody inhibits the mitogenic response of Schwann cells. In NPL 6, an anti-NRG1 antibody was able to suppress the cell division of schwannoma cells (benign tumor cells), suggesting a possibility to treat schwannoma using an anti-NRG1 antibody. Moreover, NPL 7 discloses that adding a culture supernatant of SK-Hep1, which is hepatocellular carcinoma (HCC)-derived cells, enhanced phosphorylation of ErbB3 in HepG2, which is also HCC-derived cells, but the phosphorylation was not enhanced by a culture supernatant pretreated with an anti-NRG1 antibody. Further, NPL 8 discloses an antibody (3G11) which exhibits a neutralizing activity against the growth stimulation by NRG1 isoform 6 (SMDF). Nevertheless, it has also been revealed that, even with such an antibody exhibiting a neutralizing activity, no inhibitory effect was observed against MCF7 and T47D, which are cancer cells (see the description of the fifth line from the bottom in the left column at page 248 of this literature to the line 13 in the left column at page 248). As such, under current situations, no antibody against NRG1 has been developed which has a sufficient activity in the treatments of various diseases in which NRG1 is presumably involved, particularly in the cancer treatments.

CITATION LIST

Non Patent Literatures

[NPL 1] Loeb et al., Mol. Cel. Neurosci., 1998, vol. 11, pp. 77 to 91
[NPL 2] Montero J. C. et al., Mol. Cell Neurosci., 2000, vol. 16, pp. 631 to 648
[NPL 3] Shirakabe K. et al., J. Biol. Chem., 2001, vol. 276, pp. 9352 to 9358
[NPL 4] Montero J. C. et al., Biochem. J., 2002, vol. 363, pp. 211 to 221

[NPL 5] Rosenbaum C. et al., Exp Neurol., 1997, vol. 148, iss. 2, pp. 604 to 615

[NPL 6] Hansen M R. et al., Glia, 2006, vol. 53, iss. 6, pp. 593 to 600

[NPL 7] Hsieh S Y. et al., Hepatology. 2011, vol. 53, iss. 2, pp. 504 to 516

[NPL 8] Osheroff P L. et al., Growth Factors, 1999, vol. 16, no. 3, pp. 241 to 253

SUMMARY OF INVENTION

Technical Problems

The present invention has been made in view of the above-described problems of the conventional techniques. An object of the present invention is to provide an antibody capable of specifically recognizing a human NRG1 protein isoform, and suppressing signal transduction in which the isoform is involved. Another object of the present invention is to provide an antibody specific to a human NRG1 protein isoform, the antibody having an anti-tumor activity.

Solution to Problems

In order to achieve the above objects, the present inventors immunized mice with a total of 11 partial-length proteins of human NRG1 protein isoforms 1 and 2 (a human NRG1-β1 protein and a human NRG1-α protein), and obtained a total of 80 clones of a monoclonal antibody against the human NRG1 protein. Further, among these monoclonal antibodies, four monoclonal antibodies (8a2, 8a4, 10bM3, and 10b2M3) were selected based on strong reactivities with an NRG1 protein at the cell surface. Then, these monoclonal antibodies were analyzed for the binding specificity to the human NRG1 protein isoforms, and epitopes were identified. As a result, it was found out that 8a2 was an antibody capable of binding to both the human NRG1-α protein and the human NRG1-β1 protein, and that its epitope was located on the N-terminal side of an EGF domain, which is a common region of the human NRG1-α protein and the human NRG1-β1 protein. Meanwhile, it was revealed that 8a4 was an antibody capable of specifically binding to the human NRG1-α protein but not to the human NRG1-β1 protein, and that the epitope for the antibody was particularly a region at positions 221 to 234 of the human NRG1-α protein. Further, it was revealed that both of 10bM3 and 10b2M3 were antibodies capable of specifically binding to the human NRG1-β1 protein but not to the human NRG1-α protein, and the epitope for the antibodies was particularly located in a region at positions 213 to 239 of the human NRG1-β1 protein. In this manner, the present inventors successfully obtained the antibodies specific to any one of the human NRG1-α protein and the human NRG1-β1 protein.

The present inventors determined sequences of heavy chain and light chain variable regions and CDRs of these mouse monoclonal antibodies specific to the human NRG1 protein isoforms. Further, based on the sequences thus determined, chimeric antibodies were also prepared by substituting the constant regions with one derived from human IgG. Then, the chimeric antibodies obtained in this manner and the mouse monoclonal antibodies on which these chimeric antibodies were based were earnestly studied. The result revealed that when specifically binding to any one of the region at positions 221 to 234 of the human NRG1-α protein and the region at positions 213 to 239 of the human NRG1-β1 protein, these antibodies were able to inhibit the human NRG1 protein cleavage that would otherwise trigger signal transduction in which the protein is involved. Moreover, it was found that these antibodies were also capable of suppressing phosphorylation of an ErbB3 protein in a cancer cell that would otherwise occur in the signal transduction. Further, it was also found that administering these antibodies specific to the human NRG1 protein isoforms to mice into which cancer cells had been transplanted suppressed an increase in the tumor and significantly increased the survival rate of the mice. On the other hand, it was also found that the antibody (8a2) capable of binding to both the human NRG1-α protein and the human NRG1-β1 protein did not have all of the activity of suppressing cleavage of the human NRG1 proteins, the activity of suppressing phosphorylation of an ErbB3 protein in a cancer cell, and the activity of suppressing in vivo tumor proliferation. These findings have led to the completion of the present invention. To be more specific, the present invention provides the following <1> to <11>.

<1> An antibody capable of binding to any one of a region at positions 221 to 234 of a human NRG1-α protein shown in SEQ ID NO: 1 and a region at positions 213 to 239 of a human NRG1-β1 protein shown in SEQ ID NO: 2.

<2> The antibody according to <1>, which has an activity of suppressing cleavage of any one of the human NRG1-α protein shown in SEQ ID NO: 1 and the human NRG1-β1 protein shown in SEQ ID NO: 2.

<3> The antibody according to <1> or <2>, which has an activity of suppressing phosphorylation of an ErbB3 protein in a cancer cell in response to a stimulus by any one of the human NRG1-α protein shown in SEQ ID NO: 1 and the human NRG1-β1 protein shown in SEQ ID NO: 2.

<4> The antibody according to any one of <1> to <3>, which has an activity of suppressing in vivo tumor proliferation.

<5> The antibody according to <1>, which has any one of the following features (a) to (c):

(a) comprising a light chain variable region including amino acid sequences of SEQ ID NOs: 3 to 5 or the amino acid sequences in at least any one of which one or more amino acids are substituted, deleted, added, and/or inserted, and a heavy chain variable region including amino acid sequences of SEQ ID NOs: 7 to 9 or the amino acid sequences in at least any one of which one or more amino acids are substituted, deleted, added, and/or inserted;

(b) comprising a light chain variable region including amino acid sequences of SEQ ID NOs: 11 to 13 or the amino acid sequences in at least any one of which one or more amino acids are substituted, deleted, added, and/or inserted, and a heavy chain variable region including amino acid sequences of SEQ ID NOs: 15 to 17 or the amino acid sequences in at least any one of which one or more amino acids are substituted, deleted, added, and/or inserted; and (c) comprising a light chain variable region including amino acid sequences of SEQ ID NOs: 19 to 21 or the amino acid sequences in at least any one of which one or more amino acids are substituted, deleted, added, and/or inserted, and a heavy chain variable region including amino acid sequences of SEQ ID NOs: 23 to 25 or the amino acid sequences in at least any one of which one or more amino acids are substituted, deleted, added, and/or inserted.

<6> The antibody according to <1>, which has any one of the following features (a) to (c):

(a) comprising
  a light chain variable region including an amino acid sequence of SEQ ID NO: 6 or the amino acid sequence in which one or more amino acids are substituted, deleted, added, and/or inserted, and
  a heavy chain variable region including an amino acid sequence of SEQ ID NO: 10 or the amino acid sequence in which one or more amino acids are substituted, deleted, added, and/or inserted;

(b) comprising
  a light chain variable region including an amino acid sequence of SEQ ID NO: 14 or the amino acid sequence in which one or more amino acids are substituted, deleted, added, and/or inserted, and
  a heavy chain variable region including an amino acid sequence of SEQ ID NO: 18 or the amino acid sequence in which one or more amino acids are substituted, deleted, added, and/or inserted; and (c) comprising
  a light chain variable region including an amino acid sequence of SEQ ID NO: 22 or the amino acid sequence in which one or more amino acids are substituted, deleted, added, and/or inserted, and
  a heavy chain variable region including an amino acid sequence of SEQ ID NO: 26 or the amino acid sequence in which one or more amino acids are substituted, deleted, added, and/or inserted.

<7> An antibody having any one of the following features (a) to (c):

(a) comprising
  a light chain variable region including amino acid sequences of SEQ ID NOs: 3 to 5 or the amino acid sequences in at least any one of which one or more amino acids are substituted, deleted, added, and/or inserted, and
  a heavy chain variable region including amino acid sequences of SEQ ID NOs: 7 to 9 or the amino acid sequences in at least any one of which one or more amino acids are substituted, deleted, added, and/or inserted;

(b) comprising
  a light chain variable region including amino acid sequences of SEQ ID NOs: 11 to 13 or the amino acid sequences in at least any one of which one or more amino acids are substituted, deleted, added, and/or inserted, and
  a heavy chain variable region including amino acid sequences of SEQ ID NOs: 15 to 17 or the amino acid sequences in at least any one of which one or more amino acids are substituted, deleted, added, and/or inserted; and (c) comprising
  a light chain variable region including amino acid sequences of SEQ ID NOs: 19 to 21 or the amino acid sequences in at least any one of which one or more amino acids are substituted, deleted, added, and/or inserted, and
  a heavy chain variable region including amino acid sequences of SEQ ID NOs: 23 to 25 or the amino acid sequences in at least any one of which one or more amino acids are substituted, deleted, added, and/or inserted.

<8> An antibody having any one of the following features (a) to (c):

(a) comprising
  a light chain variable region including an amino acid sequence of SEQ ID NO: 6 or the amino acid sequence in which one or more amino acids are substituted, deleted, added, and/or inserted, and
  a heavy chain variable region including an amino acid sequence of SEQ ID NO: 10 or the amino acid sequence in which one or more amino acids are substituted, deleted, added, and/or inserted;

(b) comprising
  a light chain variable region including an amino acid sequence of SEQ ID NO: 14 or the amino acid sequence in which one or more amino acids are substituted, deleted, added, and/or inserted, and
  a heavy chain variable region including an amino acid sequence of SEQ ID NO: 18 or the amino acid sequence in which one or more amino acids are substituted, deleted, added, and/or inserted; and (c) comprising
  a light chain variable region including an amino acid sequence of SEQ ID NO: 22 or the amino acid sequence in which one or more amino acids are substituted, deleted, added, and/or inserted, and
  a heavy chain variable region including an amino acid sequence of SEQ ID NO: 26 or the amino acid sequence in which one or more amino acids are substituted, deleted, added, and/or inserted.

<9> An antibody capable of binding to an epitope recognized by the antibody according to any one of <1> to <8>.

<10> A DNA encoding the antibody according to any one of <1> to <9>.

<11> A hybridoma which produces the antibody according to any one of <1> to <9>, or comprises the DNA according to <10>.

<12> A composition for treating or preventing a cancer, the composition comprising the antibody according to any one of <1> to <9> as an active ingredient.

<13> A method for preparing the antibody according to any one of <1> to <9>, the method comprising the steps of:
  immunizing an animal with any one of
    a peptide having the region at positions 221 to 234 of the human NRG1-α protein shown in SEQ ID NO: 1 or positions 213 to 239 of the human NRG1-β1 protein shown in SEQ ID NO: 2,
    a partial peptide of the peptide, and
    a protein containing the peptide;
  purifying antibodies from the immunized animal; and
  selecting, among the antibodies purified in the previous step, an antibody capable of binding to any one of the peptides.

Advantageous Effects of Invention

The present invention makes it possible to provide an antibody capable of specifically recognizing a human NRG1 protein isoform, and suppressing signal transduction in which the isoform is involved. Moreover, the present invention also makes it possible to provide an antibody specific to a human NRG1 protein isoform, the antibody having an anti-tumor activity.

DESCRIPTION OF EMBODIMENTS

Figure 1:
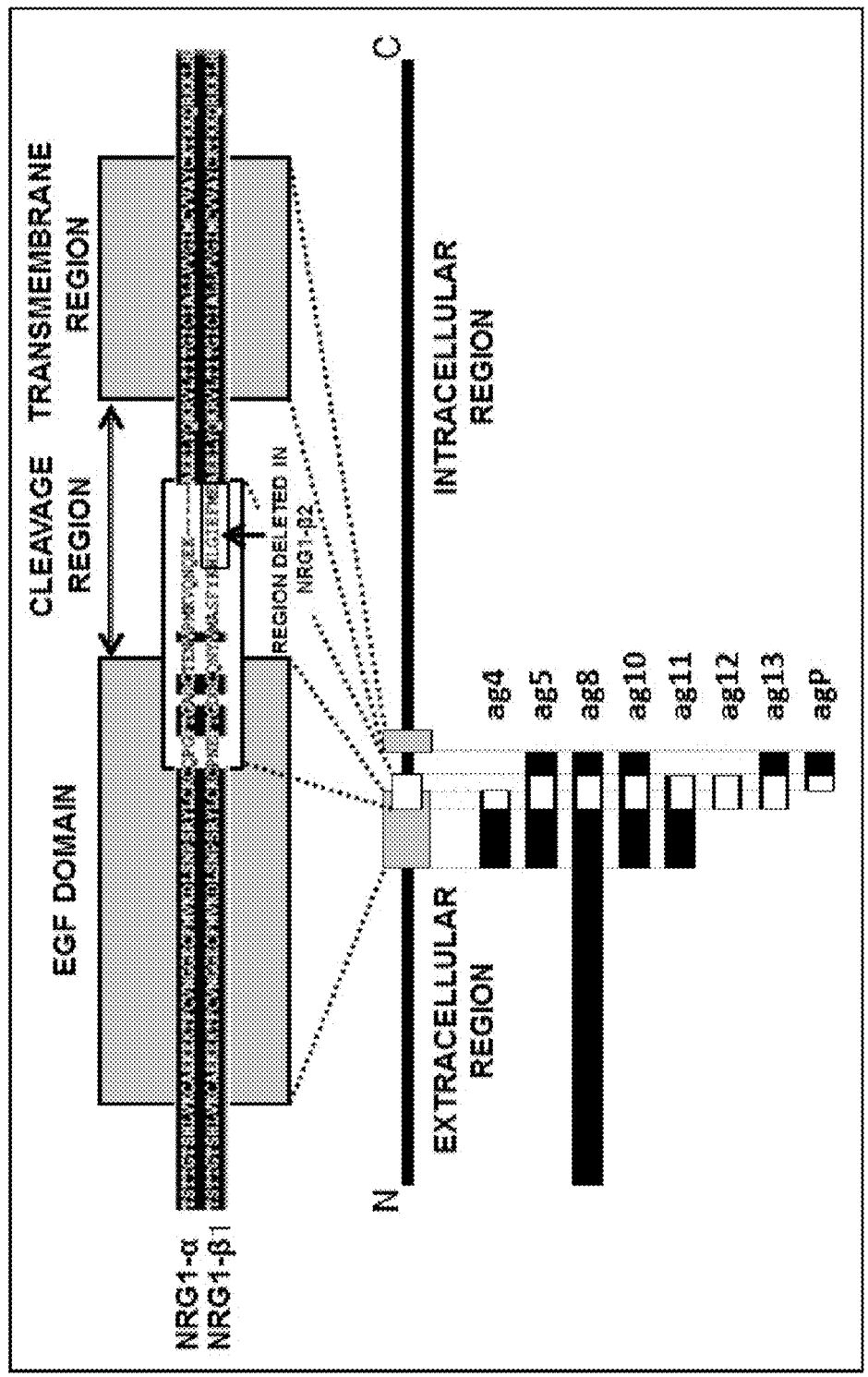
FIG. 1 is a schematic drawing showing the result of comparing the structure and the amino acid sequence between a human NRG1-α protein and a human NRG1-β1 protein, and also showing a positional relation of human NRG1 proteins of partial-length proteins (ag4 to ag13, and agP) used as immunogens to prepare antibodies of the present invention.

As described later in Examples, the present inventors have successfully prepared antibodies specific to any one of human NRG1 protein isoforms 1 and 2 (a human NRG1-β1 protein and a human NRG1-α protein). Further, the inventors have identified epitopes for the obtained antibodies, and also found that these antibodies have an activity of remarkably suppressing signal transduction in which the human NRG1 protein is involved. Thus, the pre sent invention provides the following antibody capable of specifically binding to a human NRG1 protein isoform.

An antibody capable of binding to anyone of a region at positions 221 to 234 of a human NRG1-α protein shown in SEQ ID NO: 1 and a region at positions 213 to 239 (preferably positions 232 to 239) of a human NRG1-β1 protein shown in SEQ ID NO: 2.

In the present invention, the term "antibody" includes all classes and subclasses of immunoglobulins. An "antibody" includes a polyclonal antibody and a monoclonal antibody, and is also meant to include the form of a functional fragment of an antibody. A "polyclonal antibody" is an antibody preparation including different antibodies against different epitopes. Meanwhile, a "monoclonal antibody" means an antibody (including an antibody fragment) obtained from a substantially uniform antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

In the present invention, "NRG1" is a protein also referred to as neuregulin 1, HRGα (heregulin-α), HGL, HRGA, NDF (Neu differentiation factor), ARIA (acetylcholine receptor inducing activator), GGF2 (glial growth factor 2), SMDF (sensory and motor-neuron derived factor), and so forth.

The human-derived NRG1 protein isoform 2 (human NRG1-α protein) is typically a protein having an amino acid sequence of SEQ ID NO: 1 (the protein is specified under RefSeq ID: NP_039258, and the protein is encoded by abase sequence specified under RefSeq ID: NM_013964). Thus, the "region at positions 221 to 234 of a human NRG1-α protein" is typically a region having an amino acid sequence from a threonine residue at position 221 to a lysine residue at position 234 of SEQ ID NO: 1.

The human-derived NRG1 protein isoform 1 (human NRG1-β1 protein) is typically a protein having an amino acid sequence of SEQ ID NO: 2 (the protein is specified under RefSeq ID: NP_039250, and the protein is encoded by a base sequence specified under RefSeq ID: NM_013956). Thus, the "region at positions 213 to 239 (or positions 232 to 239) of a human NRG1-β1 protein" is typically a region having an amino acid sequence from a proline residue at position 213 (or a histidine residue at position 232) to a glutamic acid residue at position 239 of SEQ ID NO: 2.

Note that whether a human NRG1 protein is α type or β type can be determined by a difference in selected exons encoding a 10 amino-acid residue long C-terminal part of an EGF domain and a juxtamembrane domain (which is a region located on the C-terminal side of the EGF domain and on the N-terminal side of the transmembrane sequence). To be more specific, the human NRG1-α protein is a protein encoded by a human NRG1 splicing variant containing exon 11, while a human NRG1-β protein is a protein encoded by a human NRG1 splicing variant containing exon 12a. Further, regarding β type, a protein encoded by a human NRG1 splicing variant having exon 13 as an exon following the exon 12a is the human NRG1-β1 protein, while a protein encoded by a human NRG1 splicing variant having no exon 13 is a human NRG1-β2 protein. As to the numbers assigned to the exons, see the description of exons of RefSeq ID: NM_013964 (human NRG1-α), RefSeq ID: NM_013956 (human NRG1-β1), and RefSeq ID: NM_013957 (human NRG1-β2).

Moreover, the region at positions 221 to 234 of the human NRG1-α protein or the region at positions 213 to 239 of the human NRG1-β1 protein may exist in a form having some amino acid naturally mutated, besides ones having typical amino acid sequences as described above. Thus, besides the above-described amino acid sequences, the region at positions 221 to 234 of SEQ ID NO: 1 or the region at positions 213 to 239 (or positions 232 to 239) of SEQ ID NO: 2 further includes the amino acid sequence in which one or more amino acids are substituted, deleted, inserted, or added. Generally, 10 amino acids or less (for example, 5 amino acids or less, 3 amino acids or less, 1 amino acid) in the amino acid sequence are substituted, deleted, inserted, or added.

Further, a site where the antibody of the present invention binds, that is, "epitope", means an antigen determinant present in an antigen (i.e., the aforementioned regions) (a site on an antigen where an antigen-binding domain in the antibody binds). Thus, in the present invention, the epitope may be a polypeptide (linear epitope) having several consecutive amino acids in a primary sequence of amino acids, or may be a polypeptide (discontinuous epitope, conformational epitope) formed of amino acids which are not next to each other in a primary sequence of amino acids, but which come near each other in a three-dimensional conformation by folding or the like of a peptide or protein. Moreover, such an epitope typically has at least 3 amino acids, most usually at least 5 amino acids (for example, 8 to 10, 6 to 20).

The "signal transduction in which the human NRG1 protein is involved" and which the antibody of the present invention is capable of suppressing by binding to the particular region in any one of the human NRG1-α protein and the human NRG1-β1 protein, is meant to include not only a series of biological reactions activated by binding between soluble human NRG1 protein and an EGF receptor, but also cleavage (so-called shedding) and release of the human NRG1 protein that trigger the signal transduction. To be more specific, the antibody of the present invention should have an activity of suppressing at least any one of processes: cleavage of any one of the human NRG1-α protein and the human NRG1-β1 protein, release of a soluble NRG1 protein after the cleavage, binding between the soluble NRG1 protein and an EGF receptor (ErbB3 or ErbB4), change in the structure of ErbB3 or ErbB4 attributable to the binding, homodimerization or heterodimerization of ErbB3 or ErbB4 induced by the structural change, phosphorylation of ErbB3 or ErbB4 attributable to the dimerization (in response to a stimulus by any one of the human NRG1-α protein and the human NRG1-β1 protein), activation of the MAPK pathway elicited by the phosphorylation, and activation of the PI3K-Akt pathway elicited by the phosphorylation, as well as cell proliferation, cell differentiation, cell migration, cell adhesion, cell infiltration, and the like induced by the activations of these pathways.

Further, among these processes, the antibody preferably has an activity of suppressing at least anyone of processes, "cleavage of any one of the human NRG1-α protein and the human NRG1-β1 protein," "phosphorylation of ErbB3 or ErbB4 in response to a stimulus by any one of the human NRG1-α protein and the human NRG1-β1 protein," and "cell proliferation." The antibody more preferably has an activity of suppressing all of the three processes.

The "cleavage of any one of the human NRG1-α protein and the human NRG1-β1 protein" means cleavage of the human NRG1-α or human NRG1-β1 protein in a juxtamembrane domain thereof by a protease such as TACE or ADAM19 activated by PMA, PKC, Erk1/2, p38, and the like. Additionally, the activity of suppressing such cleavage can be evaluated, for example, by a method described later in Example 5.

The "phosphorylation of ErbB3 or ErbB4 in response to a stimulus by any one of the human NRG1-α protein and the human NRG1-β1 protein" means tyrosine phosphorylation in an intracellular domain of ErbB3 or ErbB4 in response to the binding between the soluble NRG1 protein and ErbB3 or ErbB4, and so forth. A target to be suppressed by the antibody of the present invention is preferably phosphorylation of an ErbB3 protein, more preferably phosphorylation of an ErbB3 protein in a cancer cell. Additionally, the activity of suppressing such phosphorylation can be evaluated, for example, by a method described later in Example 6.

In the present invention, the phrase "suppressing cell proliferation" is meant to include not only suppression of cell proliferation (cell division) per se, but also suppression of cell proliferation by inducing cell death (such as apoptosis). Moreover, a target to be suppressed by the antibody of the present invention is preferably cancer cell proliferation, more preferably in vivo cancer cell (tumor) proliferation. Further, the activity of suppressing such in vivo tumor proliferation can be evaluated, for example, by a method described later in Example 11. A preferable embodiment of the antibody of the present invention is an antibody capable of making a tumor volume 30% or less (for example, 25% or less, 20% or less, 15% or less, 10% or less, 5% or less, 0%) 80 days after a cancer cell line is transplanted according to the method, provided that a tumor volume of a negative control group is taken as 100%.

Furthermore, the type of cancer as a target to be suppressed by the antibody of the present invention is not particularly limited because associations between NRG1 and various cancers have been revealed as described below.

For example, lung cancer has been examined for expressions of ErbB2, ErbB3, and ErbB4 frequently. It has been shown that ErbB3 is over-expressed (Poller, D. N. et al. (1992) J. Pathol., 168, 275-280), and that the ErbB3 over-expression correlates with a poor prognosis (Yi, E. S. et al. (1997) Mod. Pathol., 10, 142-148). Further, it has also been reported that the ErbB activation by NRG1 causes carcinogenesis (Al Moustafa, A. E. et al. (1999) Anticancer Res., 19, 481-486; Gollamudi, M. et al. (2004) Lung Cancer, 43, 135-143). Moreover, it has also been shown that EGFR forms a heterodimer with ErbB3 and is also involved in the signal transduction regulated by NRG1 (Engelman, J. A. et al. (2006) Clin. Cancer Res., 12, 4372-4376). Furthermore, it has also been reported that the ErbB3 gene amplification was observed in non-small-cell lung cancer patients having received gefitinib administration (Cappuzzo, F. et al. (2005) Br. J. Cancer, 93, 1334-1340).

Moreover, regarding ovarian cancer, associations have been shown between NRG1 expression and cell proliferation in the cancer and many cell lines derived therefrom. Further, it has been shown that expression levels of various ErbB receptors, particularly expression levels of ErbB3 and ErbB2, are closely associated with the NRG1 response (Aguilar, Z. et al. (1999) Oncogene, 18, 6050-6062; Gilmour, L. M. et al. (2002) Clin. Cancer Res., 8, 3933-3942).

Furthermore, in colorectal cancer, it has been shown that NRG1 activates ErbB2/ErbB3 in an autocrine manner and causes cell proliferation independent of other growth factors (Venkateswarlu, S. et al. (2002) Oncogene, 21, 78-86).

In addition, it has also been reported that the ErbB3 expression is enhanced in stomach cancer (Sanidas, E. E. et al. (1993) Int. J. Cancer, 54, 935-940). It has been suggested that NRG1-α produced by mesenchymal cells functions in a paracrine manner and contributes to carcinogenesis (Noguchi, H. et al. (1999) Gastroenteroloy, 117, 1119-1127). Further, there is a report that the ErbB4 is also over-expressed in stomach cancer, suggesting that NRG1-α functions via ErbB4, too.

Moreover, regarding breast cancer, NRG1 expression enhancement has been observed in 30% of patients not over-expressing ErbB2, indicating that NRG1 is associated with carcinogenesis of mammary gland epithelial cells via ErbB2/ErbB3 (Li, Q. et al. (2004) Cancer Res., 64, 7078-7085). In addition, the NRG1 expression is more likely to be observed in estrogen receptor-negative breast cancer than estrogen-positive breast cancer (Normanno, N. et al. (1995) Breast Cancer Res. Treat. 35, 293-297). Further, many studies have been conducted on the associations of NRG1 and ErbB with hormone requirements (Tang, C. K. et al. (1996) Cancer Res., 56, 3350-3358; Grunt, T. W. et al. (1995) Int. J. Cancer, 63, 560-567; Pietras, R. J. et al. (1995) Oncogene, 10, 2435-2446). It has been suggested that breast cancer expressing NRG1 leads to a poor prognosis (Lupu, R. et al. (1996) Breast Cancer Res. Treat., 38, 57-66). The NRG1 over-expression causes breast cancer progression and metastasis through MMP-9 and VEGF expression enhancements regardless of the presence or absence of estrogen stimulation and ErbB2 over-expression (Atlas, E. et al. (2003) Mol. Cancer Res., 1, 165-175).

Additionally, it has been shown that ErbB1, ErbB2, ErbB3, and NRG1 are expressed in the prostate. It has been suggested that NRG1 is associated with prostate differentiation in a paracrine manner, and that a dysfunction in the NRG1/ErbB signal transduction pathway causes early carcinogenesis (Grasso, A. W. et al. (1997) Oncogene, 15, 2705-2716; Lyne, J. C. et al. (1997) Cancer J. Sci. Am., 3, 21-30). Moreover, in another study, NRG1 and ErbB3 are over-expressed in many prostate cancers, indicating that NRG1-α functions in an autocrine manner (Leung, H. Y. et al. (1997) Br. J. Urol., 79, 212-216). Further, it has been shown that the ErbB2/ErbB3 activation by NRG1 is associated with the androgen receptor activation and prostate cancer recurrence in the absence of a hormone (Gregory, C. W. et al. (2005) Clin. Cancer Res., 11, 1704-1712.).

Moreover, it has been shown that the NRG1 expression is enhanced in thyroid cancer and lymph node metastasis, too. In addition, NRG1 is detected in nuclei in many cases of papillary thyroid cancer, which is the most frequently occurring type of thyroid cancer. It has been suggested that there may be an NRG1 action mechanism involving no ErbB because no correlation of the NRG1 expression enhancement and nuclear staining with the ErbB expression was observed (Fluge, O. et al. (2000) Int. J. Cancer, 87, 763-770).

Further, regarding gliomas also, it has been suggested that NRG1 is expressed (Westphal, M. et al. (1997) J. Neurooncol., 35, 335-346.), that NRG1 signaling is associated with the cell survival (Flores, A. I. et al. (2000) J. Neurosci., 20, 7622-7630), and further that NRG1 contributes to infiltration through the activation of adhesion related molecules (van der Horst, E. H. et al. (2005) Int. J. Cancer, 113, 689-698).

Furthermore, regarding medulloblastoma, it has been stated that the NRG1 expression is observed in 87% thereof, and that the expression tends to be stronger in cases expressing ErbB2 and ErbB4, and further there is also a description of the expressions of all of these three factors and metastases (Gilbertson, R. J. et al. (1998) Cancer Res., 58, 3932-3941).

Moreover, in melanocytes and many melanoma-derived culture cells, a possibility has been shown that the NRG1/ErbB system regulates the proliferation (Gordon-Thomson, C. et al. (2005) Melanoma Res., 15, 21-28). Further, it has also been shown that the NRG1 over-expression and secretion regulate the cell proliferation and migration in an autocrine or a paracrine manner (Stove, C. et al. (2003) J. Invest. Dermat., 121, 802-812).

Additionally, regarding pancreatic cancer, it has been shown that a large amount of NRG1 is expressed in the cancer tissue, and that the expression level of β type NRG1 correlates with the patient survival rate (Kolb, A. et al. (2007) Int. J. Cancer, 120, 514-523).

Further, it has also been shown that NRG1 promotes cancer cell infiltration through regulation of actin cytoskeleton (Hijazi, M. M. et al. (2000) Int. J. Oncol., 17, 629-641). Furthermore, although trastuzumab is an anti-HER2 antibody to be administered to a patient observed to over-express HER2, a possibility has been shown that trastuzumab is significantly effective in a case where NRG1 (NRGa2c) is expressed at a high level even if the HER2 expression level is not high (de Alava, E. et al. (2007) J. Clin. Oncol., 25, 2656-2663). In addition, a study using breast cancer cells has shown that NRG1 functions to regulate the self-renewal capacity of cancer stem cells, produce various extracellular secretory proteins such as IL-8, and mature the cancer stem cell niche (microenvironment) (Hinohara, K. et al. (2012) Proc. Nat. Acad. Sci. USA, 109, 6584-6589).

Another preferable embodiment of the antibody of the present invention is an antibody having any one of the following features (a) to (c), and another more preferable embodiment includes an antibody having any one of the following features (a) to (c) and being capable of binding to any one of the region at positions 221 to 234 of the human NRG1-α protein shown in SEQ ID NO: 1 and the region at positions 213 to 239 (preferably, positions 232 to 239) of the human NRG1-β1 protein shown in SEQ ID NO: 2:

(a) comprising
   a light chain variable region including amino acid sequences of light chain CDR1 to CDR3 (amino acid sequences of SEQ ID NOs: 3 to 5 or the amino acid sequences in at least any one of which one or more amino acids are substituted, deleted, added, and/or inserted), and
   a heavy chain variable region including amino acid sequences of heavy chain CDR1 to CDR3 (amino acid sequences of SEQ ID NOs: 7 to 9 or the amino acid sequences in at least any one of which one or more amino acids are substituted, deleted, added, and/or inserted);

(b) comprising
   a light chain variable region including amino acid sequences of light chain CDR1 to CDR3 (amino acid sequences of SEQ ID NOs: 11 to 13 or the amino acid sequences in at least any one of which one or more amino acids are substituted, deleted, added, and/or inserted), and
   a heavy chain variable region including amino acid sequences of heavy chain CDR1 to CDR3 (amino acid sequences of SEQ ID NOs: 15 to 17 or the amino acid sequences in at least any one of which one or more amino acids are substituted, deleted, added, and/or inserted); and (c) comprising
   a light chain variable region including amino acid sequences of light chain CDR1 to CDR3 (amino acid sequences of SEQ ID NOs: 19 to 21 or the amino acid sequences in at least any one of which one or more amino acids are substituted, deleted, added, and/or inserted), and
   a heavy chain variable region including amino acid sequences of heavy chain CDR1 to CDR3 (amino acid sequences of SEQ ID NOs: 23 to 25 or the amino acid sequences in at least any one of which one or more amino acids are substituted, deleted, added, and/or inserted).

Another more preferable embodiment of the antibody of the present invention is an antibody having any one of the following features (a) to (c), and still another more preferable embodiment includes an antibody having any one of the following features (a) to (c) and being capable of binding to any one the region at positions 221 to 234 of the human NRG1-α protein shown in SEQ ID NO: 1 and the region at positions 213 to 239 (preferably, positions 232 to 239) of the human NRG1-β1 protein shown in SEQ ID NO: 2:

(a) comprising
   a light chain variable region including an amino acid sequence of SEQ ID NO: 6 or the amino acid sequence in which one or more amino acids are substituted, deleted, added, and/or inserted, and
   a heavy chain variable region including an amino acid sequence of SEQ ID NO: 10 or the amino acid sequence in which one or more amino acids are substituted, deleted, added, and/or inserted;

(b) comprising
   a light chain variable region including an amino acid sequence of SEQ ID NO: 14 or the amino acid sequence in which one or more amino acids are substituted, deleted, added, and/or inserted, and
   a heavy chain variable region including an amino acid sequence of SEQ ID NO: 18 or the amino acid sequence in which one or more amino acids are substituted, deleted, added, and/or inserted; and (c) comprising
   a light chain variable region including an amino acid sequence of SEQ ID NO: 22 or the amino acid sequence in which one or more amino acids are substituted, deleted, added, and/or inserted, and
   a heavy chain variable region including an amino acid sequence of SEQ ID NO: 26 or the amino acid sequence in which one or more amino acids are substituted, deleted, added, and/or inserted.

Once the antibody comprising the light chain variable region and the heavy chain variable region is obtained, those skilled in the art can prepare various antibodies capable of binding to a peptide region (epitope) specified on any one of the region at positions 221 to 234 of the human NRG1-α protein shown in SEQ ID NO: 1 and the region at positions 212 to 239 (or positions 232 to 239) of the human NRG1-β1 protein shown in SEQ ID NO: 2 derived from human and recognized by the antibody and also capable of suppressing the signal transduction in which any one of the human NRG1-α protein and the human NRG1-β1 protein is involved. The epitope for the antibody can be determined by well-known methods such as checking, by ELISA or the like, binding to an overlapping synthetic oligopeptide obtained from the amino acid sequence of any one of the human NRG1-α protein and the human NRG1-β1 protein as described later in Examples. Alternatively, a peptide library in phage display can also be used for the epitope mapping. Further, whether two antibodies bind to the same epitope or sterically overlapping epitopes can be determined by a competitive assay method.

The antibody of the present invention includes a mouse antibody, a chimeric antibody, a humanized antibody, a human antibody, and a functional fragment of these antibodies. For administration as a pharmaceutical agent to human, the antibody of the present invention is desirably a chimeric antibody, a humanized antibody, or a human antibody from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Concretely, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. Nos. 4,816,397, 4,816,567, and 5,807,715). Moreover, in the present invention, a "humanized antibody" is an antibody obtained by grafting (CDR grafting) a gene sequence of an antigen-binding site (CDR) of a non-human-derived antibody onto a human antibody gene. The preparation methods are known (see, for example, EP239400, EP125023, WO90/07861, WO96/02576). In the present invention, a "human antibody" is an antibody all regions of which are derived from human. In preparing a human antibody, it is possible to utilize a screening method for a production of an antibody having a higher activity than human B cells, a phage display method, a transgenic animal (for example, a mouse) capable of producing a repertoire of the human antibody by immunization, or other means. Preparation methods for a human antibody are known (for example, Nature, 362: 255-258 (1993), Intern. Rev. Immunol, 13: 65-93 (1995), J. Mol. Biol, 222: 581-597 (1991), Nature Genetics, 15: 146-156 (1997), Proc. Natl. Acad. Sci. USA, 97: 722-727 (2000), Japanese Unexamined Patent Application Publication Nos. Hei 10-146194 and Hei 10-155492, Japanese Patent No. 2938569, Japanese Unexamined Patent Application Publication No. Hei 11-206387, International Application Japanese-Phase Publication Nos. Hei 8-509612 and Hei 11-505107).

In the present invention, a "functional fragment" of an antibody means apart (partial fragment) of an antibody, which binds to any one of the region at positions 221 to 234 of the human NRG1-α protein shown in SEQ ID NO: 1 and the region at positions 212 to 239 (or positions 232 to 239) of the human NRG1-β1 protein shown in SEQ ID NO: 2. Concretely, examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

Here, "Fab" means a monovalent antigen-binding fragment, of an immunoglobulin, composed of a part of one light chain and a part of one heavy chain. Fab can be obtained by papain digestion of an antibody or by a recombinant method. "Fab'" is different from Fab in that a small number of residues are added to the carboxy terminus of a heavy chain CH1 domain including one or more cysteines from an antibody hinge region. "F(ab')2" means a bivalent antigen-binding fragment, of an immunoglobulin, composed of parts of both light chains and parts of both heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (scFv)" includes a heavy chain variable region and a light chain variable region of an antibody, and these regions exist in a single polypeptide chain. A "sc(Fv)2" is a single chain obtained by linking two heavy chain variable regions and two light chain variable regions with a linker or the like. A "diabody" is a small antibody fragment having two antigen-binding sites. This fragment includes a heavy chain variable region linked to a light chain variable region in a single polypeptide chain. Each region forms a pair with a complementary region in another chain. A "polyspecific antibody" is a monoclonal antibody having a binding specificity to at least two different antigens. For example, a polyspecific antibody can be prepared by coexpression of two immunoglobulin heavy chain/light chain pairs in which two heavy chains have different specificities.

The antibody of the present invention includes antibodies whose amino acid sequences are modified without impairing desirable activities (activity of binding to an antigen, activity of suppressing the signal transduction in which any one of the human NRG1-α protein and the human NRG1-β1 protein is involved, and/or other biological properties). An amino acid sequence mutant of the antibody of the present invention can be prepared by introduction of a mutation into a DNA encoding an antibody chain of the present invention or by peptide synthesis. Examples of such a modification include substitution, deletion, addition, and/or insertion of a residue in the amino acid sequence of the antibody of the present invention. A site where the amino acid sequence of the antibody is modified may be a constant region of the heavy chain or the light chain of the antibody or a variable region (framework region and CDR) thereof, as long as the resulting antibody has activities equivalent to those before the modification. It is conceivable that modification on an amino acid other than CDR has a relatively small influence on binding affinity for an antigen. As of now, there are known screening methods for an antibody whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acids or less, 1 amino acid). The modification of amino acids is preferably conservative substitution. In the present invention, the term "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), amino acids containing sulfur (cysteine, methionine), amino acids having an amide group (asparagine, glutamine), an amino acid having an imino group (proline), and amino acids having an aromatic group (phenylalanine, tyrosine, tryptophan).

Meanwhile, "having equivalent activities" or similar phrases mean that the activity of binding to an antigen or the activity of suppressing the signal transduction is equivalent (for example, 70% or more, preferably 80% or more, more preferably 90% or more) to that of a subject antibody (typically, 8a4, 10bM3, or 10b2M3 described later in Examples). The activity of binding to an antigen can be evaluated, for example, by analyzing the reactivity with an antigen by ELISA, or preparing cells expressing an antigen and then analyzing the reactivity with an antibody sample using a flow cytometer, as described later in Examples. Moreover, the activity of suppressing the signal transduction can be evaluated, for example, based on the percentage of an NRG1 protein remaining on the cell surface stimulated with PMA, the degree of the phosphorylation of an ErbB3 protein in a cancer cell stimulated with an NRG1 protein, the tumor volume of a xenograft mouse, or the like, by a method described later in Examples.

Further, the modification of the antibody of the present invention may be a modification on post-translational process of the antibody such as, for example, alternation of the number or position of the glycosylation sites. Thereby, for example, the ADCC activity of the antibody can be improved. Glycosylation of the antibody is typically N-linked or O-linked glycosylation. The glycosylation of the antibody largely depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. Nos. 5,047,335, 5,510,261, and 5,278,299, International Publication No. WO99/54342). Furthermore, in the present invention, for the purpose of increasing the stability of the antibody or other purposes, an amino acid subjected to deamidation or an amino acid next to the amino acid subjected to the deamidation may be substituted with a different amino acid to suppress the deamidation. Alternatively, the stability of the antibody can also be increased by substituting glutamic acid with a different amino acid. The present invention also provides an antibody thus stabilized.

In the case where the antibody of the present invention is a polyclonal antibody, the polyclonal antibody can be obtained as follows. Concretely, an animal is immunized with an antigen (a polypeptide having an amino acid sequence of positions 221 to 234 of the human NRG1-α protein or positions 213 to 239 (or positions 232 to 239) of the human NRG1-β1 protein, a partial peptide of the polypeptide, cells expressing these, or the like). An antiserum from the animal is purified by conventional means (for example, salting-out, centrifugation, dialysis, column chromatography, or the like) to obtain the polyclonal antibody. Meanwhile, a monoclonal antibody can be prepared by a hybridoma method or a recombinant DNA method.

The hybridoma method is typically a method by Kohler and Milstein (Kohler & Milstein, Nature, 256: 495 (1975)). Antibody-producing cells used in the cell fusion process of this method are spleen cells, lymph node cells, peripheral blood leukocytes, or the like of an animal (for example, mouse, rat, hamster, rabbit, monkey, goat, chicken, camel) immunized with the antigen. It is also possible to use antibody-producing cells obtained by causing the antigen to act, in a medium, on the above-described types of cells, lymphocytes, or the like, which are isolated from non-immunized animals in advance. As myeloma cells, various known cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to any one of the human NRG1-α protein and the human NRG1-β1 protein can be obtained. The monoclonal antibody specific to any one of the human NRG1-α protein and the human NRG1-β1 protein can be obtained by culturing the hybridoma, or from the ascites of a mammal to which the hybridoma is administered.

The recombinant DNA method is a method by which the antibody of the present invention is produced as a recombinant antibody as follows. A DNA encoding the antibody of the present invention is cloned from a hybridoma, B cells, or the like. The cloned DNA is incorporated into an appropriate vector, which is then introduced into host cells (for example, a mammalian cell line, Escherichia coli, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding the heavy chain and the light chain may be incorporated into expression vectors, respectively, to transform the host cells. Alternatively, the DNAs encoding the heavy chain and the light chain may be incorporated into a single expression vector to transform the host cells (see International Publication No. WO94/11523). The antibody of the present invention can be obtained in a substantially pure and homogeneous form by culturing the host cells, followed by separation and purification from the host cells or the culture solution. For the separation and purification of the antibody, normal methods used for polypeptide purification can be employed. When a transgenic animal (cattle, goat, sheep, pig, or the like) incorporating the antibody gene is prepared using a transgenic animal preparation technique, a large amount of monoclonal antibodies derived from the antibody gene can also be obtained from milk of the transgenic animal.

Thus, the present invention can also provide: a DNA encoding the antibody of the present invention; and a hybridoma which produces the antibody of the present invention, or comprises the DNA encoding the antibody of the present invention. Moreover, the present invention can also provide a method for preparing the antibody of the present invention described below.

A method for preparing the antibody of the present invention, the method comprising the steps of:
immunizing an animal with any one of
a peptide having the region at positions 221 to 234 of the human NRG1-α protein shown in SEQ ID NO: 1 or positions 213 to 239 of the human NRG1-β1 protein shown in SEQ ID NO: 2,
a partial peptide of the peptide, and
a protein containing the peptide;
purifying antibodies from the immunized animal; and
selecting, among the antibodies purified in the previous step, an antibody capable of binding to any one of the peptides.

In the method for preparing the antibody of the present invention, the "animal" to be immunized is not particularly limited, and examples thereof include non-human animals such as mouse, rat, hamster, rabbit, monkey, goat, chicken, and camel, as described above. Moreover, in "purifying antibodies from the immunized animal," the antibodies may be purified, for example, from an antiserum of the immunized animal by conventional means (for example, salting-out, centrifugation, dialysis, column chromatography, or the like) as described above. Alternatively, such antibodies may be purified by conventional means from a hybridoma obtained by fusing myeloma cells to antibody-producing cells obtained from the immunized animal. The method for "selecting" an antibody capable of binding to any one of the peptides among the antibodies purified as described above is not particularly limited, either. Examples thereof include an analysis of the reactivity with the peptide by ELISA, and a method in which cells expressing the peptide are prepared and then the reactivity with the antibodies is analyzed using a flow cytometer, as described later in Examples.

Moreover, the antibody of the present invention may comprise a compound or molecule such as a drug or prodrug binding to the antibody. Administering such an antibody allows delivering of the compound or molecule to a site (for example, cancer cells) where any one of the human NRG1-α protein and the human NRG1-β1 protein is expressed. Such a drug or prodrug is not particularly limited, but is preferably a substance having an anti-tumor activity from the viewpoint of additionally or synergistically enhancing the anti-tumor effect of the antibody of the present invention. Such a substance having an anti-tumor activity is not particularly limited, and examples thereof include anticancer agents (irinotecan (CPT-11), an irinotecan metabolite SN-38 (10-hydroxy-7-ethylcamptothecin), Adriamycin, Taxol, 5-fluorouracil; alkylating agents such as nimustine and ranimustine; antimetabolites such as gemcitabine and hydroxycarbamide; plant alkaloids such as etoposide and vincristine; anticancer antibiotics such as mitomycins and bleomycin; platinum preparations such as cisplatin; agents for molecularly targeted therapy such as sorafenib and erlotinib; methotrexate, cytosine arabinoside, 6-thioguanine, 6-mercaptopurine, cyclophosphamide, ifosfamide, busulfan, and the like. Additionally, radioisotopes can also be suitably utilized as the substance having an anti-tumor activity which binds to the antibody of the present invention.

Further, it is possible to make the antibody and the compound or molecule bind to each other by methods known in the technical field, and the binding may be any of direct binding and indirect binding. For example, in the direct binding, covalent bonding can be utilized. In the indirect binding, a linker can be utilized in the binding. Those skilled in the art can make the antibody and the compound or molecule bind to each other via such a linker, for example, with reference to the descriptions of: Hermanson, G. T. Bioconjugate Techniques, Academic Press, 1996; Harris, J. M. and Zalipsky, S. eds., Poly(ethylene glycol), Chemistry and Biological Applications, ACS Symposium Series, 1997; Veronese, F. and Harris, J. M. eds., Peptide and protein PEGylation. Advanced Drug Delivery Review 54 (4), 2002. The number of the compounds or molecules binding to one molecule of the antibody of the present invention is not particularly limited in theory, but is normally 1 to 10, preferably 1 to 8, from the viewpoints of the stability of a complex of the antibody with the compound or the like, ease of the production, and so forth.

Further, the antibody of the present invention is capable of suppressing in vivo tumor proliferation and extending the lifetime of a cancer-cell transplanted animal (xenograft mouse) in Examples described later. Accordingly, the antibody of the present invention can be utilized to treat or prevent a cancer. Thus, the present invention also provides: a composition for treating or preventing a cancer, the composition comprising the antibody of the present invention as an active ingredient; and a method for treating or preventing a cancer, the method comprising a step of administering a therapeutically or preventively effective amount of the antibody of the present invention to human. Note that the cancer as a target of the antibody of the present invention is not particularly limited as described above, and various cancers can be targeted.

The composition for treating or preventing a cancer, which comprises the antibody of the present invention as the active ingredient, can be used in the form of a composition comprising the antibody of the present invention and any ingredient, for example, a saline, an aqueous solution of glucose, a phosphate buffer, or the like. The composition for treating or preventing a cancer of the present invention may be formulated in a liquid or lyophilized form as necessary, and may also optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, a phosphate buffer, aluminium hydroxide, and the like for a liquid preparation. However, the examples are not limited thereto.

The method for administering the composition for treating or preventing a cancer of the present invention differs depending on the age, weight, sex, health state of an administration target, and the like. The administration can be carried out by any administration route: oral administration and parenteral administration (for example, intravenous administration, intraarterial administration, local administration). The dose of the composition may vary depending on the age, weight, sex, and health state of a patient, the degree of the progression of the cancer, and ingredients of the composition to be administered. Nevertheless, the dose is generally 0.1 to 1000 mg, preferably 1 to 100 mg, per kg body weight for an adult per day in the case of intravenous administration.

In the method for treating or preventing a cancer of the present invention, the method for administering the antibody of the present invention is not particularly limited as described above, and the administration can be carried by any administration route: oral administration and parenteral administration. Those skilled in the art can achieve the administration of the composition in a form appropriate therefor by selecting the pharmaceutically acceptable carrier or medium, and so forth. Those skilled in the art can determine the therapeutically or preventively "effective amount" of the antibody of the present invention to be administered to human, by taking the age, weight, sex, and health state of a patient, the degree of the progression of the cancer, the administration route, and the like into consideration as described above. Moreover, the "human" as the administration target of the antibody of the present invention is not particularly limited, and may be, for example, a person having a cancer. Alternatively, from the viewpoints of preventing and reducing cancer recurrence, the "human" may be a person from whom a cancer has been removed by a chemotherapy, radiation therapy, surgical therapy, or the like.

The method for treating or preventing a cancer of the present invention may further comprise, in addition to the step of administering the antibody of the present invention, a step of evaluating effectiveness of the antibody of the present invention. To be more specific, the present invention provides a method for treating or preventing a cancer, the method comprising the steps of:

administering a therapeutically or preventively effective amount of the antibody of the present invention to human; and evaluating effectiveness of the antibody of the present invention in the human after the administration.

The "evaluating effectiveness" of the antibody of the present invention is not particularly limited. For example, it can be determined that the antibody of the present invention is effective in a cancer treatment or the like, if the tumor size, the metastatic ability of the cancer, or expressions of various cancer markers after the administration are lower than those before the administration. Moreover, the effectiveness of the antibody of the present invention can also be evaluated based on abnormalities due to a cancer, for example, weight reduction, stomachache, back pain, reduced appetite, nausea, vomiting, systemic malaise, weakness, jaundice, and the like. Further, in a case where a tumor tissue is excised after the treatment with the antibody of the present invention, the tumor tissue may be examined for the degree of signal transduction in which a human NRG1 protein isoform is involved, in order to determine that the antibody of the present invention is effective in the cancer treatment or the like. For example, when it is detected that phosphorylation of ErbB3, which is normally enhanced in a tumor tissue, is inhibited by administering the antibody of the present invention, it can be determined that the antibody of the present invention is effective in the cancer treatment or the like.

As described above, NRG1-protein expression enhancement and the like have been recognized in various cancers. Accordingly, the antibody of the present invention is conceivably applicable not only to the treatment and prevention of a cancer but also to testing for a cancer. Particularly, since any one of the region at positions 221 to 234 of the human NRG1-α protein and the region at positions 213 to 239 of the human NRG1-β1 protein where the epitope for the antibody of the present invention is present is located in an extracellular region of the NRG1 protein, cancer cells expressing any one of the human NRG1-α protein and the human NRG1-β1 protein can be easily and efficiently detected by cell immunostaining, flow cytometry, or the like. The present invention also provides a testing agent for a cancer, the agent comprising the antibody of the present invention as an active ingredient.

When the antibody of the present invention is used in the testing for a cancer or used in the detection of a tumor site in treating the cancer, the antibody of the present invention may be labeled. As the label, it is possible to use, for example, a radioactive substance, a fluorescent dye, a chemiluminescent substance, an enzyme, or a coenzyme. When the antibody of the present invention is to be prepared as a testing agent, it can be obtained in any dosage form by adopting any means suitable for the purpose. For example, a purified antibody is measured for the antibody titer and diluted as appropriate with PBS or the like; thereafter, 0.1% sodium azide or the like can be added as a preservative thereto. Alternatively, for example, the antibody of the present invention adsorbed to latex or the like is measured for the antibody titer and diluted as appropriate, and a preservative is added thereto for use.

Additionally, the present invention has revealed that the antibody capable of binding to any one of the region at positions 221 to 234 of the human NRG1-α protein and the region at positions 213 to 239 (or positions 232 to 239) of the human NRG1-β1 protein has an anticancer activity. Accordingly, the polypeptide having positions 221 to 234 of the human NRG1-α protein or positions 213 to 239 (preferably, positions 232 to 239) of the human NRG1-β1 protein, or the partial peptide of the polypeptide can be administered as a cancer vaccine to a mammal including a human (see, for example, Japanese Unexamined Patent Application Publication Nos. 2007-277251 and 2006-052216). The present invention also provides a cancer vaccine composition for use as such a cancer vaccine, the cancer vaccine composition comprising any one of:

a polypeptide having an amino acid sequence of positions 221 to 234 of a human NRG1-α protein or positions 213 to 239 (preferably, positions 232 to 239) of a human NRG1-β1 protein; and a partial peptide of the polypeptide. When formulated, the cancer vaccine composition may comprise a pharmaceutically acceptable carrier or medium, for example, a stabilizer, a preservative, an isotonic agent, or the like, as in the case of the composition for treating or preventing a cancer of the present invention.

EXAMPLES

Hereinafter, the present invention will be more specifically described based on Examples. However, the present invention is not limited to the following Examples. Note that, herein, an NRG1-α protein, an NRG1-β1 protein, and an NRG1-β2 protein are also referred to as NRG1-a, NRG1-b, and NRG1-b2, respectively.

Example 1

Preparation of Antibody Capable of Binding to Human NRG1 Protein

Antibodies capable of binding to human NRG1 proteins were prepared by the following method.

1. Acquisition of NRG1 (NRG1-a and NRG1-b2) cDNAs
Based on the cDNA sequences of human NRG1-a and NRG1-b (HRG-α: NM_013964, HRG-β1: NM_013956), the following primers were designed for consensus sequences of 5' UTR and 3' UTR.

```
1st PCR
NRG1_5'-1:
                                    (SEQ ID NO: 27)
5'-CTTGGACCAAACTCGCCTGCG-3'

NRG1_3'-1:
                                    (SEQ ID NO: 28)
5'-ATAAAGTTTTACAGGTGAATCTATGTG-3'

2nd PCR
NRG1_5'-2:
                                    (SEQ ID NO: 29)
5'-GTAGAGCGCTCCGTCTCCGG-3'

NRG1_3'-2:
                                    (SEQ ID NO: 30)
5'-GGTTTTATACAGCAATAGGGTCTTG-3'.
```

Using SuperScriptIII cells direct cDNA Synthesis System (manufactured by Invitrogen Corporation: 18080-200), cDNAs were prepared from total RNAs extracted from human pancreatic cancer cells MIAPaCa-2 (ATCC: CRL- 1420) and AsPC-1 (ATCC: CRL-1682). Using the cDNAs as templates, cDNAs comprising the full-length NRG1-protein coding region were amplified by nested PCR using KOD Plus Ver.2 (manufactured by Toyobo Co., Ltd.: KOD-211). The 1st PCR was carried out under a condition of 35 cycles each consisting of [98° C. for 20 seconds, 60° C. for 20 seconds, 68° C. for 130 seconds], and the 2nd PCR was carried out under a condition of 35 cycles each consisting of [98° C. for 15 seconds, 61° C. for 20 seconds, 68° C. for 130 seconds]. The amplified product of the 2nd PCR was cloned in pT7Blue T-Vector (manufactured by Novagen Inc.: 69820), and the base sequence was confirmed. For the confirmation of the base sequence, an automated sequencer (manufactured by Applied Biosystems Inc.) was used. The cDNA cloned from the MIAPaCa-2 derived cDNA matched the human NRG1-α sequence, and was hence designated as NRG1-a-pT7. In comparison with the human NRG1-b sequence, the cDNA cloned from the AsPC-1 derived cDNA was observed to have 24 bases deleted from the 5' side of the transmembrane region, matched the human NRG1-b2 sequence, and was hence designated as NRG1-b2-pT7.

2. Acquisition of NRG1 (NRG1-b) cDNA

Based on the NRG1-b2 cDNA, an NRG1-b cDNA was prepared by PCR. The PCR was carried out using the NRG1-b2-pT7 as a template under a condition of 25 cycles each consisting of [95° C. for 50 seconds, 58° C. for 30 seconds, 72° C. for 10 minutes] using the following primers and Pfu (manufactured by Promega Corporation: M774A).

```
24in F:
                                              (SEQ ID NO: 31)
5'-catcttgggattgaatttatggagGCGGAGGAGCTGTACCAGAAGA
GAGTG-3'

24in R:
                                              (SEQ ID NO: 32)
5'-ctccataaattcaatcccaagatgCTTGTAGAAGCTGGCCATTACG
TAGTTTTGGC-3'
```

Note that parts shown in the small letters correspond to an NRG1-b specific sequence (the sequence is deleted in b2).

The amplified product was digested with DpnI and cloned according to a conventional method. The obtained sequence matched the human NRG1-b sequence, and was hence designated as NRG1-b-pT7.

3. Preparation of Cells Expressing Membrane NRG1

Animal cells stably expressing the full length of human NRG1-a, NRG1-b, or NRG1-b2 were prepared as follows. Note that, in order to confirm the expression of recombinant NRG1 molecules, HA tags were respectively added to N-termini thereof.

An end of a DNA having been amplified by two-stage PCR using the following primers and NRG1-a-pT7, NRG1-b-pT7, or NRG1-b2-pT7 as a template was cleaved with NotI and BamHI, and inserted into a NotI-BamHI site of an animal cell expression vector. As the animal cell expression vector, pQCxmhIPG was used which was controlled by a CMV promoter, and which simultaneously expressed a target gene and a Puromycin-EGFP fusion protein by an IRES sequence. The pQCxmhIPG is a vector modified by the present inventors from pQCXIP Retroviral Vector of "BD Retro-X Q Vectors" (manufactured by Clontech Laboratories, Inc.: 631516). The vectors thus prepared were designated as NRG1-a-pQCxmhIPG, NRG1-b-pQCxmhIPG, and NRG1-b2-pQCxmhIPG.

```
1st PCR
full_+HA-1:
5'-tatgatgtgccggattatgccTCCGAGCGCAAAGAAGGCAGAG-3'
(SEQ ID NO: 33)

full_R_BamHI:
5'-CGGGATCCTACAGCAATAGGGTCTTGGTTAG-3'
(SEQ ID NO: 34, the underline indicates a BamHI
recognition sequence)

2nd PCR
full_+HA-2:
5'-AATAGCGGCCGCACCATGccttatgatgtgccggattatgcc-3'
(SEQ ID NO: 35, the underline indicates a NotI
recognition sequence)

full_R_BamHI:
5'-CGGGATCCTACAGCAATAGGGTCTTGGTTAG-3'
(SEQ ID NO: 34, the underline indicates the BamHI
recognition sequence)
```

Parts shown in the small letters are sequences encoding a HA tag.

The prepared vectors were introduced into 293T cells using Pantropic Retroviral Expression System (manufactured by Clontech Laboratories, Inc.: K1063-1) as follows. GP2-293 (manufactured by Clontech Laboratories, Inc.: K1063-1) in an 80 to 90% confluent state was prepared on a collagen-coated 100-mm dish, into which 11.2 µg of the expression vector (NRG1-a-pQCxmhIPG, NRG1-b-pQCxmhIPG, or NRG1-b2-pQCxmhIPG) constructed above and 11.2 µg of pVSV-G (manufactured by Clontech Laboratories, Inc.: K1063-1) were co-introduced using Lipofectamine 2000 (manufactured by Invitrogen Corporation: 11668-019). After 48 hours, the supernatant containing virus particles was collected, and the virus particles were precipitated by untracentrifugion (18,000 rpm, 1.5 hours, 4° C.). The precipitate was suspended in 30 µL of THE (50 mM Tris-HCl [pH=7.8], 130 mM NaCl, 1 mM EDTA). Thereby, a retrovirus vector concentrate liquid was prepared. Five µL of the retrovirus vector concentrate liquid was diluted with 150 µL of DMEM (manufactured by SIGMA-ALDRICH CO.; D5796)—10% FBS containing 8 µg/mL of Hexadimethrine bromide (manufactured by SIGMA-ALDRICH CO.: H-9268). Thereby, a virus-particle containing medium was prepared. The virus-particle containing medium thus prepared was replaced with a 293T medium having been prepared to an approximately 40% confluent state on a 96-well microplate. These cells were cultured using DMEM (manufactured by SIGMA-ALDRICH CO.: D5796)—10% FBS containing 5 µg/mL of Puromycin (manufactured by SIGMA-ALDRICH CO.: P-8833). Thus, cells expressing a target gene were obtained.

Next, the established cells were subjected to monocloning according to a conventional method, and clones expressing a large amount of the target protein on the cell surfaces were selected. This was done by staining each clone with an anti-HA tag antibody (manufactured by MBL Co., Ltd.: M132-3) and a PE-labeled anti-mouse IgG antibody (manufactured by Beckman Coulter, Inc.: IM0855), and then measuring a mean fluorescence intensity by flow cytometry. Thus, cell lines (NRG1-a/st293T, NRG1-b/st293T, and bNRG1-b2/st293T) were established in which NRG1 having the HA tag added to the N-terminus thereof was stably expressed at a high level.

4. Preparation of Cells Secreting and Expressing Partial-Length NRG1

Animal cells expressing an EGF domain (aa181-aa222) of NRG1, or the EGF domain and a cleavage region (aa181-aa242 for NRG1-a, aa181-aa247 for NRG1-b), were prepared as follows.

An end of a DNA of partial-length NRG1 having been amplified by PCR using the following primers and NRG1-a-pT7 or NRG1-b-pT7 as a template was cleaved with NotI and BamHI, and inserted into a NotI-BamHI site of an animal cell secretory expression vector. This vector is a vector in which a sequence (5'-ATGGAGACAGACACACTCCTGCTATGGGTACTGCTGCTCTGGGTTCCAGG TTCCACTGGT-3', SEQ ID NO: 36) encoding an Igκ secretion signal peptide is incorporated upstream of a cloning site of pQCxmhIPG described above, and which is for forcibly secreting and expressing a target protein. The vectors thus prepared were designated as ag4a-pQCsxmhIPG, ag4b-pQCsxmhIPG, and ag5a-pQCsxmhIPG.

ag4a
EGF_F_NotI:
5'-AATAGCGGCCGCAAAATGTGCGGAGAAGGAGAAAAC-3'
(SEQ ID NO: 37, the underline indicates the NotI recognition sequence)

EGF-a_R_BamHI:
5'-CGGGATCCAGTACATCTTGCTCCAGTG-3'
(SEQ ID NO: 38, the underline indicates the BamHI recognition sequence)

ag4b
EGF_F_NotI:
5'-AATAGCGGCCGCAAAATGTGCGGAGAAGGAGAAAAC-3'
(SEQ ID NO: 39, the underline indicates the NotI recognition sequence)

EGF-b_R_BamHI:
5'-CGGGATCCTTGGCAGCGATCACCAGTAAACTCAT-3'
(SEQ ID NO: 40, the underline indicates the BamHI recognition sequence)

ag5a
EGF_F_NotI:
5'-AATAGCGGCCGCAAAATGTGCGGAGAAGGAGAAAAC-3'
(SEQ ID NO: 37, the underline indicates the NotI recognition sequence)

preTM_R_BamHI:
5'-CGGGTACCCACTCTCTTCTGGTACAGCTC-3'
(SEQ ID NO: 41, the underline indicates a BamHI recognition sequence).

The prepared vectors were introduced into 293T cells using Pantropic Retroviral Expression System (manufactured by Clontech Laboratories, Inc.: K1063-1) as described above. The cells were cultured using DMEM (manufactured by SIGMA-ALDRICH CO.: D5796)—10% FBS containing 5 μg/mL of Puromycin (manufactured by SIGMA-ALDRICH CO.: P-8833). Thus, cell lines (ag4a/st293T, ag4b/st293T, and ag5a/st293T) stably expressing a target gene were established.

5. Partial-Length NRG1 Purified Proteins (Preparation of Animal Cell-Derived Recombinant Proteins)

The expression cell lines (ag4a/st293T, ag4b/st293T, and ag5a/st293T) established as described above were each cultured using 1 L of CD293 (manufactured by Invitrogen Corporation). The culture supernatant was collected, and recombinant proteins were purified therefrom using TALON Purification Kit (manufactured by Clontech Laboratories, Inc.: K1253-1). The purified proteins (ag4a, ag4b, and ag5a) were confirmed by SDS-PAGE and western blot. Further, the protein concentrations were determined using Protein Assay Kit II (manufactured by Bio-Rad Laboratories, Inc.: 500-0002JA).

6. Preparation of *Escherichia coli* Expressing Partial-Length NRG1

*Escherichia coli* expressing the full-length extracellular region of NRG1 (aa1-aa242 for NRG1-a, aa1-aa247 for NRG1-b), the EGF domain and the cleavage region (aa181-aa242 for NRG1-a, aa181-aa247 for NRG1-b), a region from the N-terminus of the EGF domain to an α or type specific sequence of the cleavage region (aa181-aa234 for NRG1-a, aa181-aa239 for NRG1-b), the EGF domain and the α or β type specific sequence of the cleavage region (aa213-aa234 for NRG1-a, aa213-aa239 for NRG1-b), or a region from an α or β type specific sequence of the EGF domain to the cleavage region (aa213-aa242 for NRG1-a, aa213-aa247 for NRG1-b), was prepared as follows.

For the amplification, PCR was carried out using the following primers and NRG1-a-pT7 or NRG1-b-pT7 as a template.

ag8a, ag8b
EC_petF_BamHI:
5'-CGGGATCCATGTCCGAGCGCAAAGAAGG-3'
(SEQ ID NO: 42, the underline indicates the BamHI recognition sequence)

EGF_petR_SalI:
5'-ACGCGTCGACCACTCTCTTCTGGTACAGCTC-3'
(SEQ ID NO: 43, the underline indicates a SalI recognition sequence)

ag10a, ag10b
EGF_petF_BamHI:
5'-CGGGATCCACCACTGGGACAAGCC-3'
(SEQ ID NO: 44, the underline indicates the BamHI recognition sequence)

EGF_petR_SalI:
5'-ACGCGTCGACCACTCTCTTCTGGTACAGCTC-3'
(SEQ ID NO: 43, the underline indicates the SalI recognition sequence)

ag11a
EGF_petF_BamHI:
5'-CGGGATCCACCACTGGGACAAGCC-3'
(SEQ ID NO: 44, the underline indicates the BamHI recognition sequence)

a-specific_pet_R_SalI:
5'-ACGCGTCGACCGCCTTTTCTTGGTTTTGG-3'
(SEQ ID NO: 45, the underline indicates the SalI recognition sequence)

ag11b
EGF_petF_BamHI:
5'-CGGGATCCACCACTGGGACAAGCC-3'
(SEQ ID NO: 44, the underline indicates the BamHI recognition sequence)

b-specific_pet_R_SalI:
5'-ACGCGTCGACCGCCTCCATAAATTCAATCC-3'
(SEQ ID NO: 46, the underline indicates the SalI recognition sequence)

ag12a
a-specific_pGEX_F_BamHI:
5'-CGGGATCCTGCCAACCTGGATTCACTGG-3'
(SEQ ID NO: 47, the underline indicates the BamHI recognition sequence)

a-specific_pGEX_R_XhoI:
5'-CCGCTCGAGctaCGCCTTTTCTTGGTTTTGG-3'
(SEQ ID NO: 48, the underline indicates an XhoI recognition sequence, the small letters correspond to the stop codon)

-continued

```
ag12b
b-specific_pGEX_F_BamHI:
5'-CGGGATCCTGCCCAAATGAGTTTACTGGTG-3'
(SEQ ID NO: 49, the underline indicates the BamHI
recognition sequence)

b-specific_pGEX_R_XhoI:
5'-CCGCTCGAGctaCGCCTCCATAAATTCAATCC-3'
(SEQ ID NO: 50, the underline indicates the XhoI
recognition sequence, the small letters correspond
to the stop codon)

ag13a
a-specific_pGEX_F_BamHI:
5'-CGGGATCCTGCCAACCTGGATTCACTGG-3'
(SEQ ID NO: 47, the underline indicates the BamHI
recognition sequence)

preTM_pGEX_R_XhoI:
5'-CCGCTCGAGctaCACTCTCTTCTGGTACAGCTC-3'
(SEQ ID NO: 51, the underline indicates the XhoI
recognition sequence, the small letters correspond
to the stop codon)

ag13b
b-specific_pGEX_F_BamHI:
5'-CGGGATCCTGCCCAAATGAGTTTACTGGTG-3'
(SEQ ID NO: 49, the underline indicates the BamHI
recognition sequence)

preTM_pGEX_R_XhoI:
5'-CCGCTCGAGctaCACTCTCTTCTGGTACAGCTC-3'
(SEQ ID NO: 51, the underline indicates the XhoI
recognition sequence, the small letters correspond
to the stop codon).
```

Regarding ag8a, ag8b, ag10a, ag10b, ag11a, and ag11b, an end of an amplified DNA of partial-length NRG1 was cleaved with BamHI and SaiI, and inserted into a BamHI-XhoI site of pET28a (manufactured by Novagen Inc.: 69864-3). These were used to transform BL21, and the resultants were designated as ag8a/BL21, ag8b/BL21, ag10a/BL21, ag10b/BL21, ag11a/BL21, and ag11b/BL21.

Moreover, regarding ag12a, ag12b, ag13a, and ag13b, an end of an amplified DNA of partial-length NRG1 was cleaved with BamHI and XhoI, and inserted into a BamHI-XhoI site of pGEX4T-1 (manufactured by Amersham plc: 28-9545-49). These were used to transform BL21, and the resultants were designated as ag12a/BL21, ag12b/BL21, ag13a/BL21, and ag13b/BL21.

7. Preparation of Partial-Length NRG1 Purified Proteins (*Escherichia coli*-Derived Recombinant Proteins)

Among the *Escherichia coli* lines established as described above, each of ag8a/BL21, ag8b/BL21, ag10a/BL21, ag10b/BL21, ag11a/BL21, and ag11b/BL21 was cultured using 0.5 L of an LB medium supplemented with kanamycin, and the expression was induced using 1 mM of IPTG. Pellets thus collected were disrupted in PBS, and insoluble fractions of the pellets were solubilized using 6 M urea/PBS. After that, recombinant proteins were purified using TALON Purification Kit (manufactured by Clontech Laboratories, Inc.; K1253-1).

Moreover, each of ag12a/BL21, ag12b/BL21, ag13a/BL21, and ag13b/BL21 was cultured using 0.5 L of an LB medium supplemented with ampicillin, and the expression was induced using 1 mM of IPTG. Pellets thus collected were disrupted in 1 mM DTT/PBS (KCl free), and recombinant proteins were purified from insoluble fractions thereof using Glutathione Sepharose 4B (manufactured by GE Healthcare: 17-0756-05).

The purified proteins (ag8a, ag8b, ag10a, ag10b, ag11a, ag11b, ag12a, ag12b, ag13a, and ag13b) were confirmed by SDS-PAGE and western blot. Moreover, the protein concentrations were determined using Protein Assay Kit II (manufactured by Bio-Rad Laboratories, Inc.: 500-0002JA).

8. Preparation of Partial-Length NRG1 Purified Proteins (Synthetic Peptides)

Peptides (CTENVPMKVQNQEKAEELYQKRVL (SEQ ID NO: 52) and CQNYVMASFYKHLGIEFMEAEELYQKRVL (SEQ ID NO: 53)) containing the cleavage region of NRG1 (aa223-aa242 for NRG1-a, aa223-aa247 for NRG1-b) were synthesized according to the Fmoc method under a contract service (by MBL Co., Ltd.). Each of the peptides was made to bind to KLH according to a conventional method. Thus, agPa and agPb were obtained.

9. Immunization with Antigen

An emulsion was formed by mixing ag5a, ag7a, ag7b, ag8a, ag8b, ag10a, ag10b, ag13a, ag13b, agPa, or agPb with the same amount of a complete adjuvant (manufactured by SIGMA-ALDRICH CO.: F5881), and 4 to 5-week old BALB/c mice (manufactured by Japan SLC, Inc.) and so forth were immunized with 5 to 20 μg of the emulsion per animal 6 times at intervals of 3 to 7 days. Three days after the final immunization, lymphoid cells were extracted from the mice and fused to mouse myeloma cells P3U1 (P3-X63Ag8U1).

10. Cell Fusion

The cell fusion was carried out based on the following general method. FBS in all media used was inactivated by an incubation treatment at 56° C. for 30 minutes. P3U1 was cultured and thus prepared using RPMI 1640-10% FBS (containing Penicillin-Streptomycin). The extracted mouse lymphoid cells were mixed with P3U1 at a ratio of 10:1 to 2:1 and centrifuged. To the precipitated cells, 50% polyethylene glycol 4000 (manufactured by Merck KGaA: 1.09727.0100) was gradually added and gently mixed together. Then, the mixture was centrifuged. The precipitated fusion cells were diluted as appropriate with a 15% FBS-containing HAT medium (RPMI 1640, HAT-supplement (manufactured by Invitrogen Corporation: 11067-030), Penicillin-Streptomycin), and seeded into a 96-well microplate in an amount of 200 μL/well. The fusion cells were cultured in a $CO_2$ incubator (5% $CO_2$, 37° C.). When colonies were formed, the culture supernatant was sampled and screened as described below.

11. Selection of Cells Producing Anti-NRG1 Monoclonal Antibodies

Hybridomas producing anti-NRG1 antibodies were selected by the enzyme-linked immunosorbent assay (ELISA). The assay used the recombinant human NRG1 proteins as immunogens, which had been dispensed in a 96-well ELISA plate (manufactured by nunc A/S) in an amount of 0.5 μg/mL, that is, 50 μL/well, and left to stand at room temperature for 2 hours or 4° C. overnight for adsorption. After the solution was removed, 1% BSA (manufactured by Nacalai Tesque, Inc.: 01863-35)—5% Sucrose (manufactured by WAKO PURE CHEMICAL INDUSTRIES, LTD.)—PBS was added in an amount of 150 μL/well, and left to stand at room temperature for 2 hours to block the remaining active groups. After the resultant was left to stand, the solution was removed, and the hybridoma culture supernatant was dispensed as a primary antibody in an amount of 50 μL/well and left to stand for 1 hour. After the plate was washed with 0.05% Tween 20-PBS, an HRP-labeled anti-mouse IgG antibody (manufactured by MBL Co., Ltd.: 330) having been diluted 10000 times was added as a secondary antibody in an amount of 50 μL/well and left to stand at room temperature for 1 hour. After the plate was washed with 0.05% Tween 20-PBS, a color developing solution (5 mM sodium citrate, 0.8 mM 3.3'.5.5'-tetramethylbenzidine-2HCl, 10% N,N-dimethylformamide, 0.625% polyethylene glycol 4000, 5 mM citric acid monohydrate, 5 mM H2O2) was added thereto in an amount of 50 µL/well and left to stand at room temperature for 20 minutes to develop a color. The color development was terminated by adding 1 M phosphoric acid in an amount of 50 µL/well. Then, the absorbance at 450 nm was measured using a plate reader (manufactured by Thermo Fisher Scientific Inc.).

It was confirmed by the same ELISA that the hybridoma culture supernatants thus selected did not further react with other purified recombinant proteins having the same tag sequence as the recombinant proteins used as the immunogens. This confirmed that the produced antibodies recognized not the tag portion or the linker portion but NRG1.

Then, the hybridomas thus selected were cultured to expand using a 15% FBS-containing HT medium (RPMI 1640, HT-supplement (manufactured by Invitrogen Corporation: 21060-017), Penicillin-Streptomycin) and subjected to monocloning by the limiting dilution method.

12. Acquisition of Anti-NRG1 Monoclonal Antibodies

Each of the hybridomas having been subjected to the monocloning was cultured using a serum-free medium (manufactured by GIBCO Corp.: 12300-067). From the culture supernatant, antibodies were purified by a general affinity purification method using Protein A-Sepharose. The reactivities of these antibodies with human NRG1 were confirmed as described above by the enzyme-linked immunosorbent assay (ELISA) using the purified proteins having been used as the immunogens. The anti-NRG1 antibody serially diluted with PBS with a maximum concentration of 5 µg/mL was used as a primary antibody. The result confirmed that all the antibodies reacted with human NRG1 in a concentration dependent manner.

In this manner, a total of 80 hybridomas producing anti-NRG1 antibodies were obtained (39 clones used ag8a as an immunogen, 16 clones used ag8b as an immunogen, 16 clones used ag10a as an immunogen, 2 clones used ag10b as an immunogen, 4 clones used ag13a as an immunogen, 3 clones used agPa as an immunogen).

Example 2

Reactivities of Obtained Antibodies with Cell Surface NRG1

Figure 2:
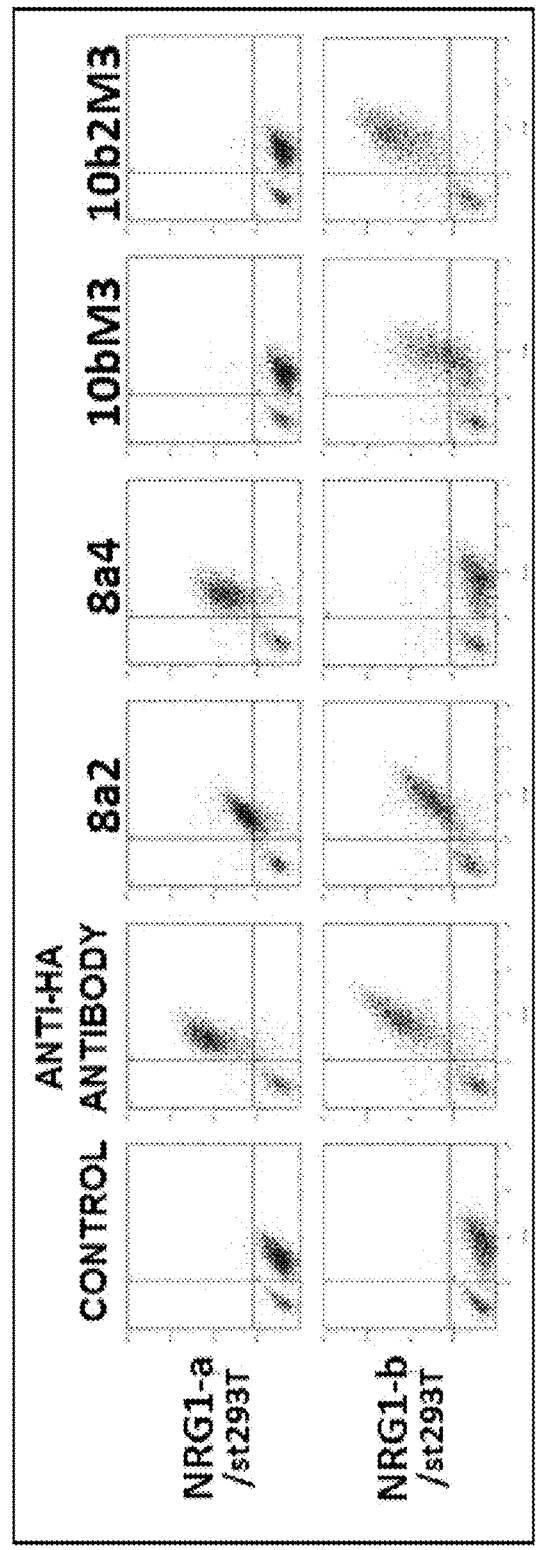
FIG. 2 shows dot plot diagrams for illustrating the result of analyzing by flow cytometry the degree of the binding between obtained antibodies (8a2, 8a4, 10bM3, and 10b2M3) against the human NRG1 proteins and a cell line (NRG1-a/st293T or NRG1-b/st293T) stably expressing a high level of any one of the human NRG1-α protein and the human NRG1-β1 protein having a HA tag added to the N-terminus thereof.

Among the obtained anti-NRG1 antibodies, ones strongly reacted with cell surface NRG1 were selected by a general method using flow cytometry. Each antibody was analyzed for mean fluorescence intensity in the flow cytometry under the same conditions (the same number of NRG1-a/st293T or NRG1-b/st293T ($5 \times 10^4$), 293T ($1 \times 10^4$), each purified antibody at the same concentration (5 µg/mL), and a secondary antibody (manufactured by Beckman Coulter, Inc.: IM0855) at the same concentration (diluted to 1/100). An anti-HA tag antibody (manufactured by MBL Co., Ltd.: M132-3) was used as a positive control to confirm the expression of NRG1 on the cell surface. Moreover, data on the mean fluorescence intensity dependent on the concentration of the antibodies were also obtained, and relative affinities were evaluated by analyzing the detection ability at low concentration. FIG. 2 shows the obtained result.

As shown in FIG. 2, it was revealed that four antibodies of 8a2, 8a4, 10bM3, and 10b2M3 among the obtained antibodies strongly reacted with NRG1 on the cell surface. Further, it was revealed that 8a2 reacted with both of NRG1-a and NRG1-b, that 8a4 specifically reacted with NRG1-a, and that 10bM3 and 10b2M3 specifically reacted with NRG1-b.

Example 3

Epitope Analysis for Obtained Antibodies

The sequences recognized by 8a2, 8a4, 10bM3, and 10b2M3 were analyzed by evaluating the reactivity with the recombinant NRG1 proteins. To be more specific, the analysis was performed using multiple partial-length NRG1 proteins, and the reactivity of each antibody with these was detected by the same enzyme-linked immunosorbent assay (ELISA) as above. FIGS. 3 to 6 show the obtained result in graphs. The vertical axis represents the absorbance. Moreover, FIG. 1 shows correspondences of NRG1-a and NRG1-b to each partial-length NRG1 protein.

Figure 7:
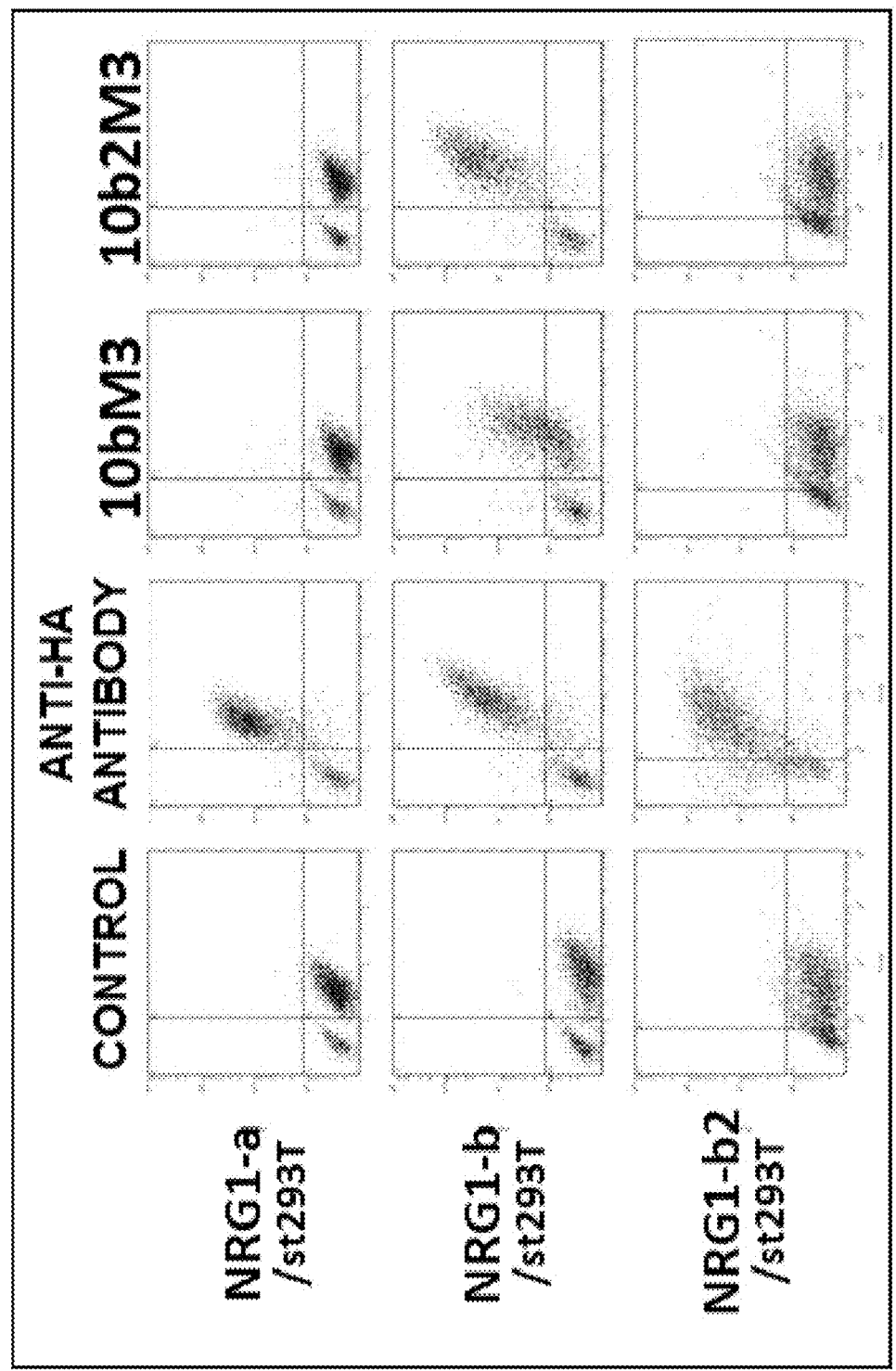
FIG. 7 shows dot plot diagrams for illustrating the result of analyzing by flow cytometry the degree of the binding of 10bM3 and 10b2M3 to a cell line (NRG1-a/st293T, NRG1-b/st293T, or NRG1-b2/st293T) stably expressing a high level of any one of the human NRG1-α protein, the human NRG1-β1 protein, and a human NRG1-β2 protein having the HA tag added to the N-terminus thereof.

Further, as to the sequence recognized by 10bM3 and 10b2M3, the reaction with NRG1-b2 on the cell surface was analyzed by the flow cytometry, too. The reactivity with NRG1-b/st293T was compared with the reactivity with NRG1-b2/st293T by the same method as above. FIG. 7 shows the obtained result.

Figure 4:
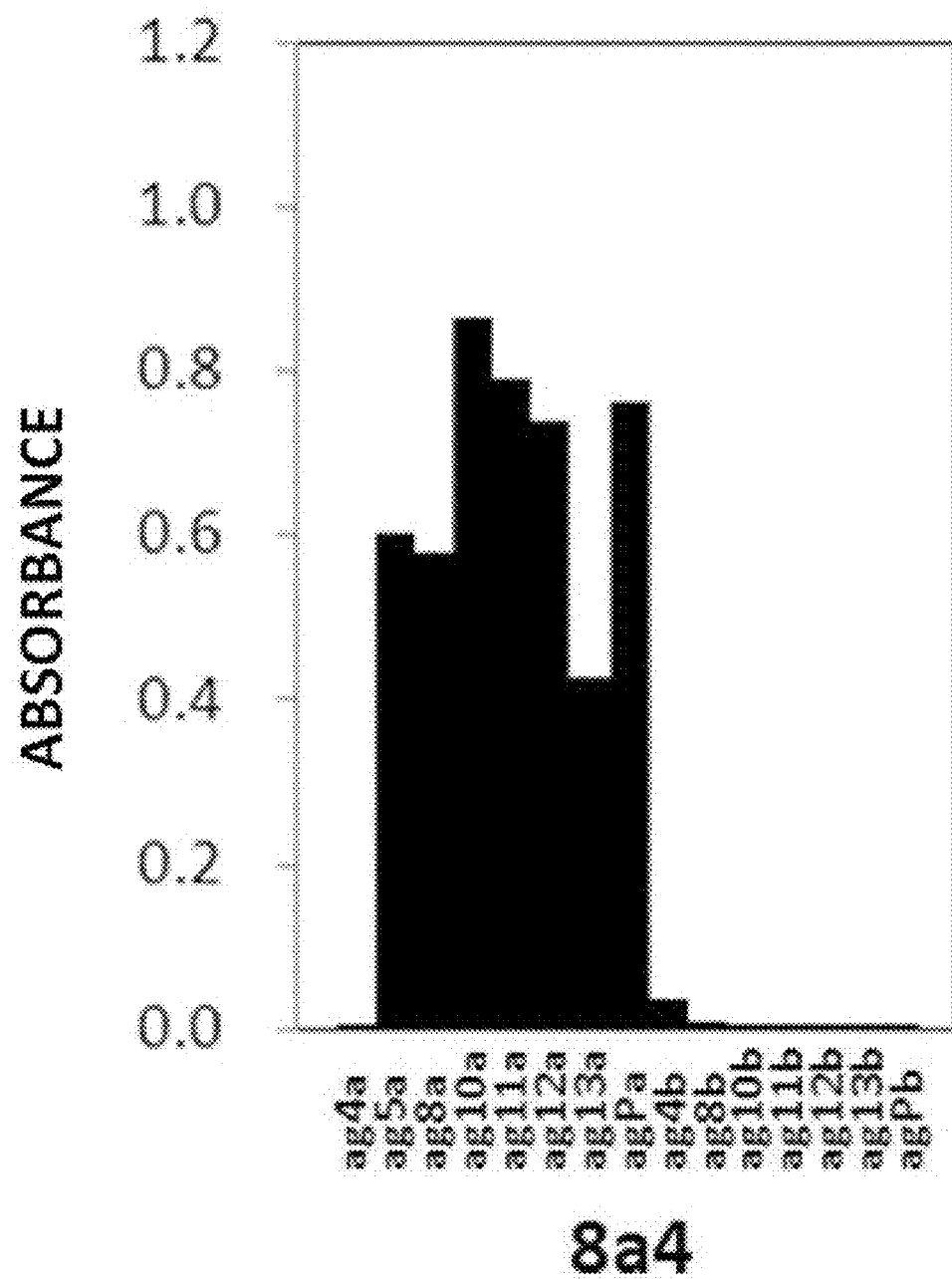
FIG. 4 is a graph for illustrating the result of analyzing by ELISA the degree of the binding of 8a4 to the partial-length human NRG1-α proteins and the partial-length human NRG1-β1 proteins.
Figure 5:
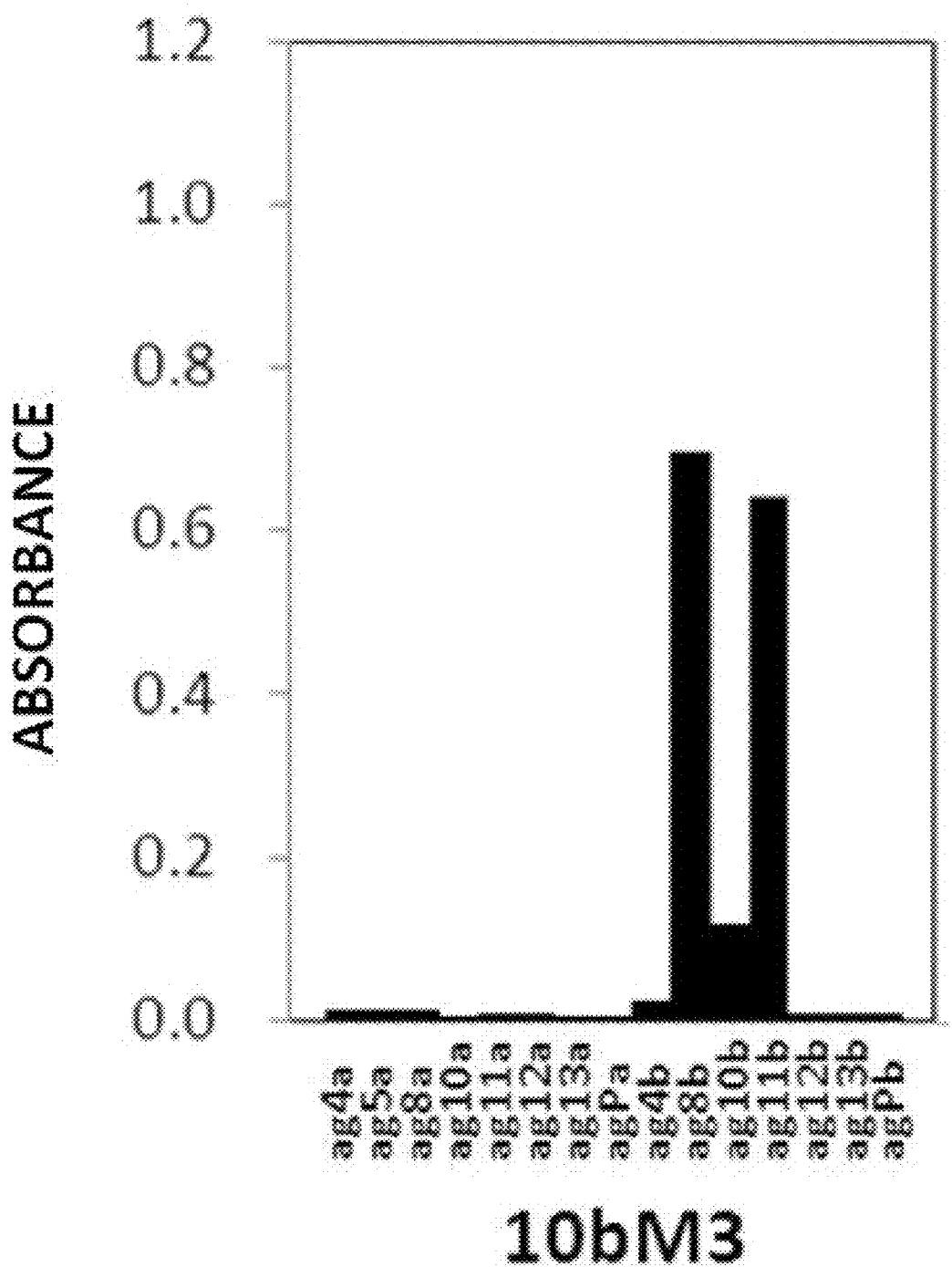
FIG. 5 is a graph for illustrating the result of analyzing by ELISA the degree of the binding of 10bM3 to the partial-length human NRG1-α proteins and the partial-length human NRG1-β1 proteins.
Figure 6:
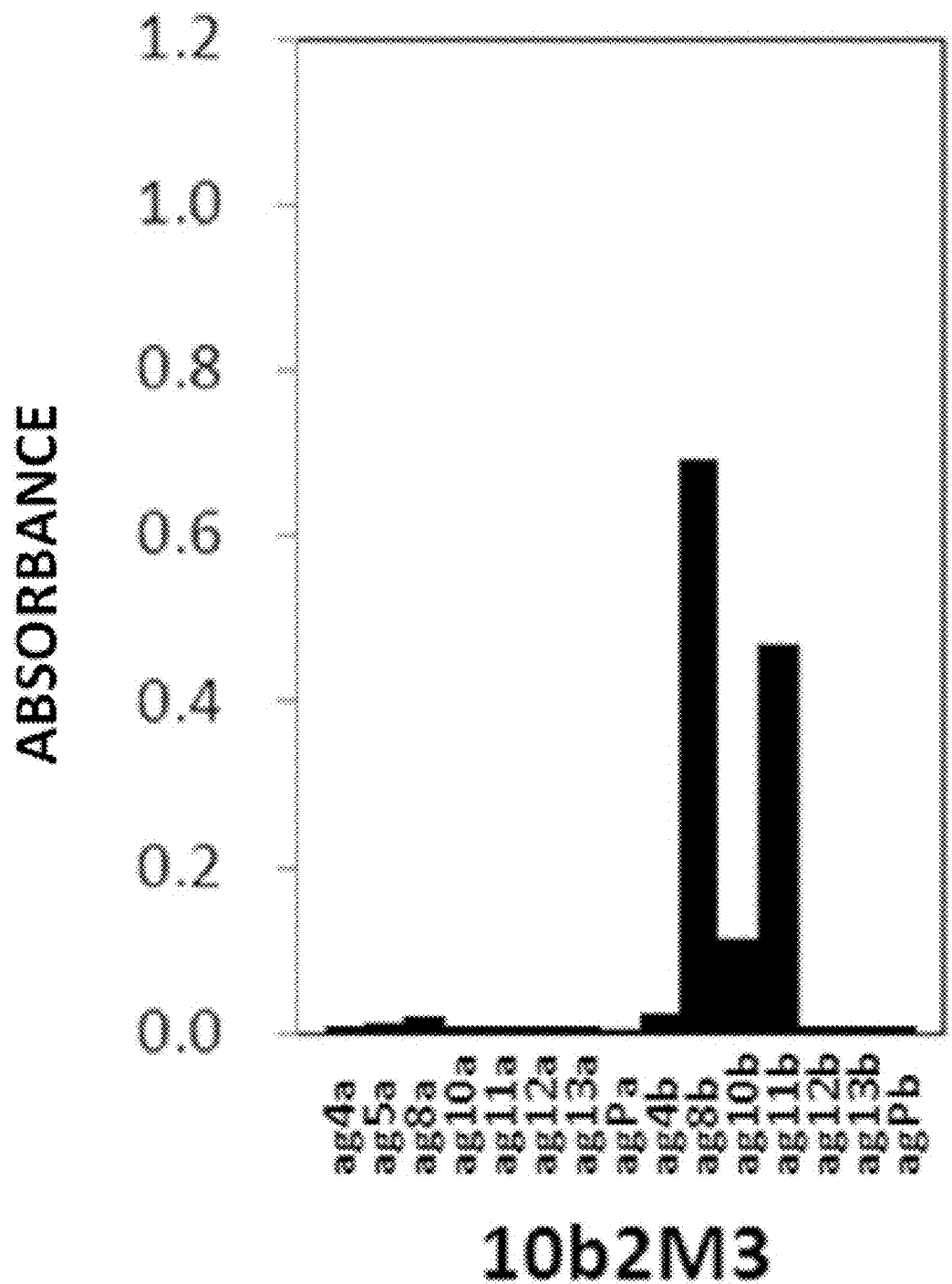
FIG. 6 is a graph for illustrating the result of analyzing by ELISA the degree of the binding of 10b2M3 to the partial-length human NRG1-α proteins and the partial-length human NRG1-β1 proteins.

As shown in FIG. 4, it was revealed that 8a4 reacted with agPa (positions 221 to 244 of the human NRG1-α protein) and ag12a (positions 212 to 235 of the human NRG1-α protein). Further, 8a4 did not react with the human NRG1-β1 protein as shown in FIG. 2. This revealed that 8a4 recognized the α type NRG1 protein isoform specific sequence, that is, the region at positions 221 to 234 of the human NRG1-α protein.

Moreover, as shown in FIGS. 5 to 7, 10bM3 and 10b2M3 did not react with the human NRG1-α proteins like the result described in Example 2. This revealed that these antibodies recognized the β type NRG1 protein isoform specific sequence, that is, the region at positions 213 to 239 of the human NRG1-β1 protein.

Further, since NRG1 proteins expressed in cells are used for the evaluation in the flow cytometry analysis, it is conceivable that this analysis is more likely to maintain correct conformation and so forth of the NRG1 proteins subjected to the reactions with the antibodies than the ELISA. Thus, when the importance is given to the analysis result by the flow cytometry (the result shown in FIG. 7), since 10bM3 and 10b2M3 do not react with the human NRG1-β2 protein, there may also be a possibility that these antibodies recognize a sequence specific to the NRG1 protein and β1 protein, that is, the region at positions 232 to 239 of the human NRG1-β1 protein.

Figure 3:
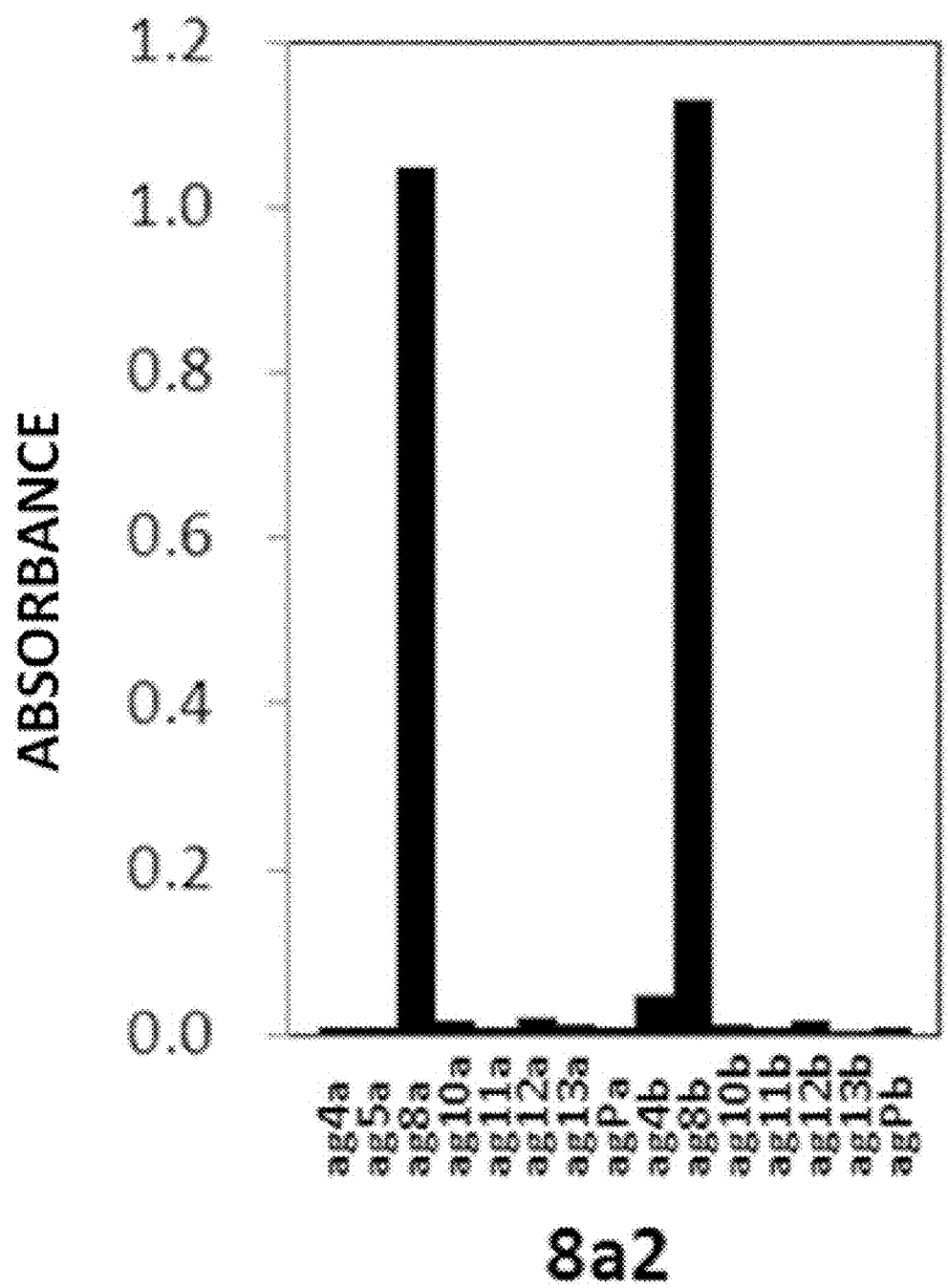
FIG. 3 is a graph for illustrating the result of analyzing by ELISA the degree of the binding of 8a2 to partial-length human NRG1-α proteins (ag4a to ag13a, and agPa) and partial-length human NRG1-β1 proteins (ag4b to ag13b, and agPb).

Note that, as shown in FIG. 3, 8a2 reacted with ag8a (positions 1 to 243 of the human NRG1-α protein) and ag8b (positions 1 to 248 of the human NRG1-β1 protein) but did not react with ag10a (positions 173 to 243 of the human NRG1-α protein) and ag10b (positions 173 to 248 of the human NRG1-β1 protein). This revealed that 8a2 recognized a common region on the N-terminal side of the EGF domain.

Example 4

Reactivities with Other Factors of EGF Family

An NRG1 protein is a protein belonging to the EGF family, but is not similar at all to the other proteins of the EGF family in regions other than the EGF domain. Additionally, regarding the EGF domain, in the first to the sixth cysteines of the EGF domain, the NRG1 protein has a homology of 45% with HB-EGF (heparin-binding EGF-like growth factor), a homology of 35% with AREG (amphiregulin), a homology of 32% with TGF-α (transforming growth factor α), and a homology of 27% with EGF (see Holmes et al., Science, 1992, vol. 256, pp. 1205 to 1210).

Figure 8:
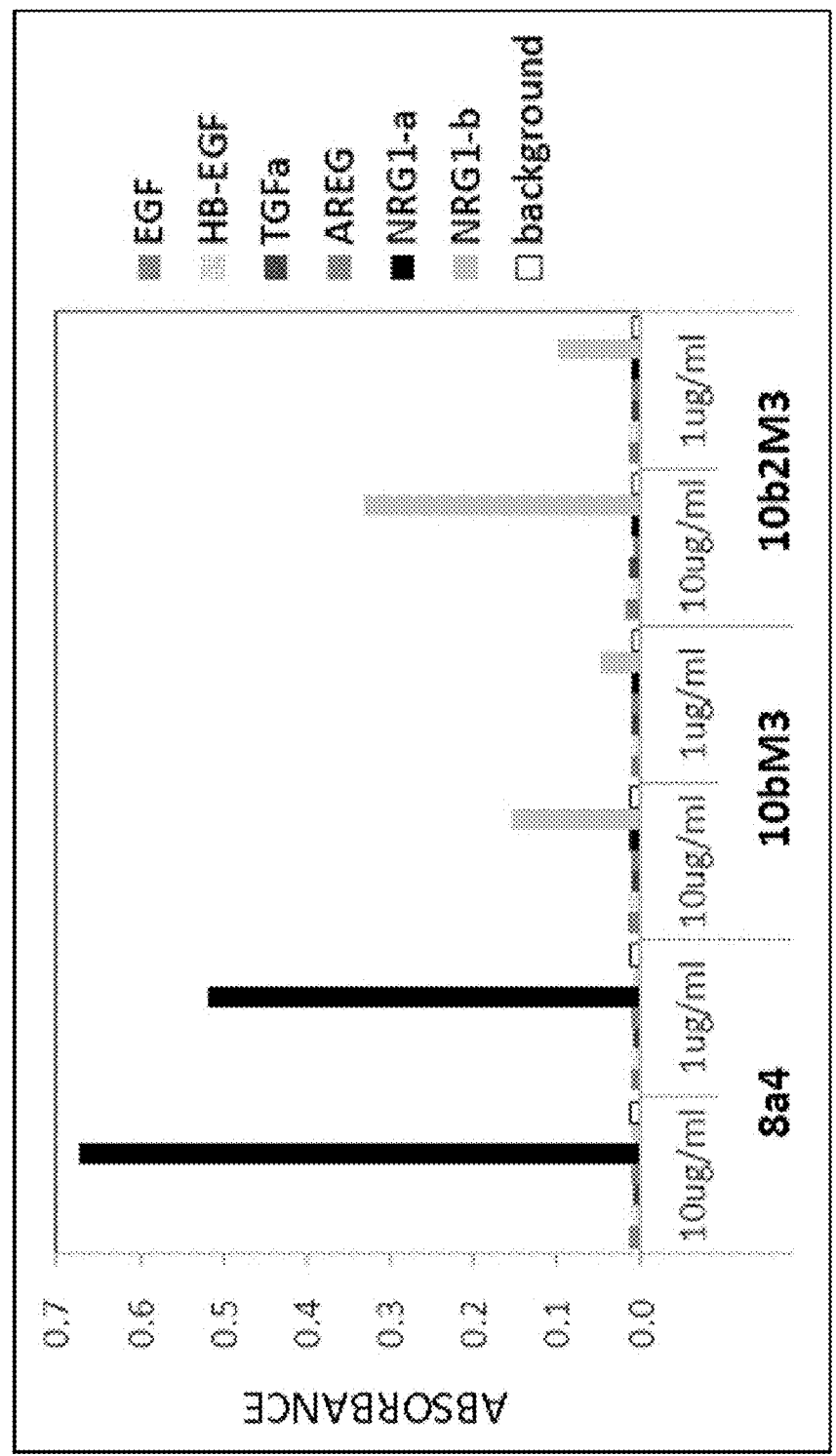
FIG. 8 is a graph for illustrating the result of analyzing by ELISA the degree of the binding between the antibodies of the present invention (8a4, 10bM3, and 10b2M3) and factors belonging to the EGF family (EGF, HB-EGF, TGFa (TGFα), AREG, NRG1-a (NRG1-α), and NRG1-b (NRG1-β1)).

As described above, any homology with the NRG1 protein is low in the EGF domain. Nonetheless, 8a4, 10bM3, and 10b2M3 capable of recognizing the vicinity of the EGF domain were analyzed for the reactivity with the other factors of the EGF family by the same ELISA as above. To be more specific, each of EGF (manufactured by R&D Systems, Inc.: 236-EG-200), HB-EGF (manufactured by R&D Systems, Inc.: 259-HE-050/CF), TGF-alpha (manufactured by R&D Systems, Inc.: 239-A-100), AREG (manufactured by R&D Systems, Inc.: 262-AR-100/CF), NRG1-α (manufactured by R&D Systems, Inc.: 296-HR-050/CF), or NRG1-b (manufactured by R&D Systems, Inc.: 296-HB-050/CF) was dispensed in a 96-well ELISA plate in an amount of 0.5 μg/mL, that is, 50 μL/well, and immobilized thereto, for detection of the reaction with each antibody in amounts of 10 μg/mL and 1 μg/mL. As a result, none of 8a4, 10bM3, and 10b2M3 reacted with the other factors of the EGF family as shown in FIG. 8.

Example 5

Evaluation 1 of NRG1-Cleavage Inhibitory Activities of Obtained Antibodies

Whether or not the obtained antibodies were capable of specifically suppressing signal transduction in which any one of the human NRG1-α protein and the human NRG1-β1 protein was involved was evaluated. In other words, whether or not the obtained antibodies were capable of specifically suppressing cleavage of these proteins that would otherwise trigger the signal transduction was evaluated by the following method.

The HA-NRG1-a/st293T, HA-NRG1-b/st293T, or HA-NRG1-b2/st293T was seeded into a 96-well microplate in an amount of 20000 cells per well, and cultured at 37° C. for 6 hours. After it was confirmed that the cells adhered to the bottom surface of the plate, the medium was replaced with a DMEM medium containing no serum, and the resultant was further cultured for 15 hours.

Next, the medium was replaced with a medium to which 8a2, 8a4, 10bM3, 10b2M3, or a control antibody (manufactured by MBL Co., Ltd.: M075-3) had been added, and incubated at 37° C. for 60 minutes. In this event, the antibody concentration was set to five levels of 80, 20, 5, 1, and 0 μg/mL, and the amount of the medium per well was 60 μL. Subsequently, a medium supplemented with PMA having been adjusted to 600 nM was added in an amount of 30 μL per well and mixed together, so that PMA was added at a final concentration of 200 nM. After cultured at 37° C. for 30 minutes, the cells were collected by pipetting. Note that all the samples of each antibody were prepared in 3 wells. Additionally, it has been revealed that PMA (phorbol-12-myristate-13-acetate) activates protein kinase C (PKC), thereby inducing NRG1 shedding.

Figure 9:
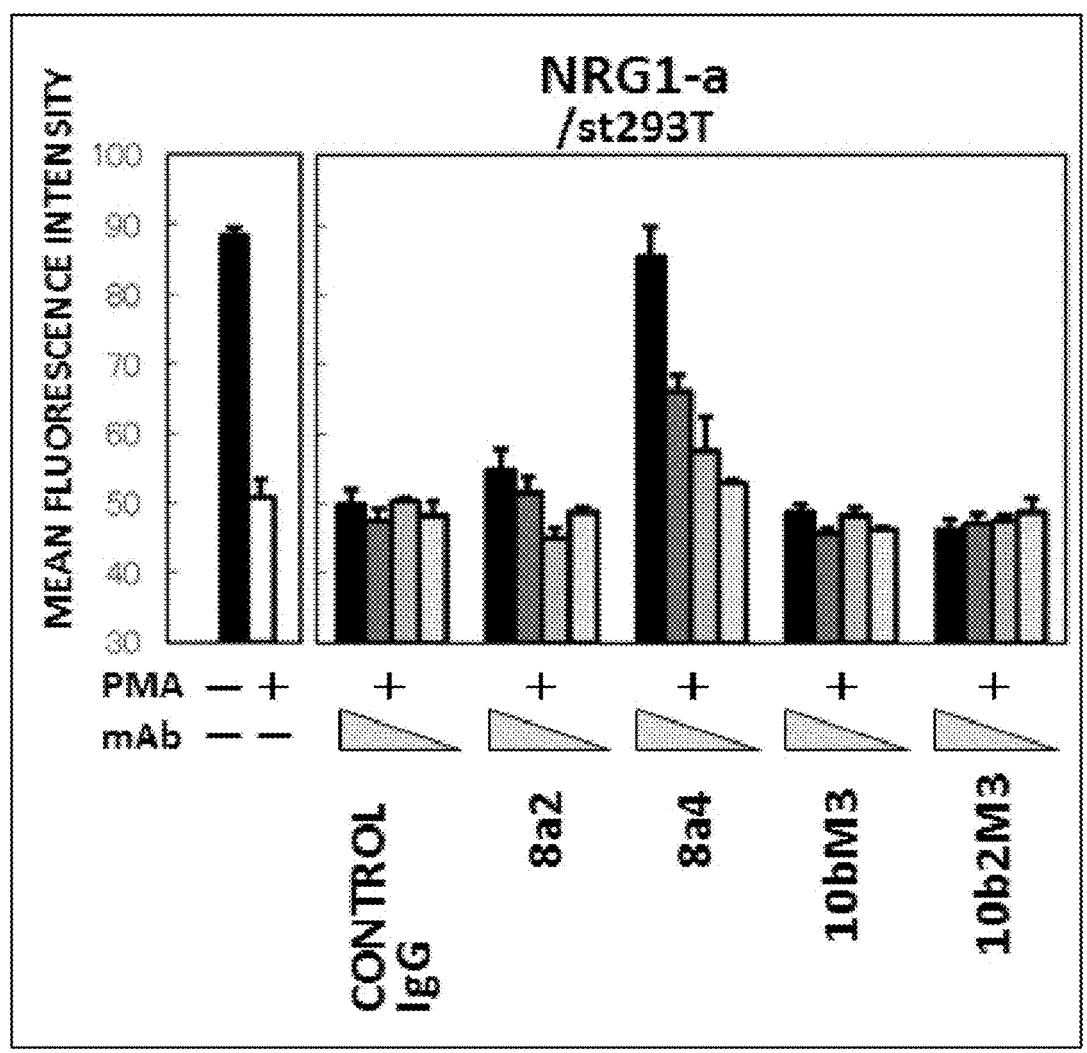
FIG. 9 is a graph for illustrating the result of analyzing by flow cytometry 8a2 and the antibodies of the present invention (8a4, 10bM3, and 10b2M3) for the activity of suppressing the human NRG1-α protein cleavage that would otherwise occur by PMA. The vertical axis represents the amount of the human NRG1-α protein (mean fluorescence intensity) remaining on the surfaces of the cells (NRG1-a/st293T) after PMA was added. Moreover, four bars in each group show the results when each antibody was added at a concentration of 80, 20, 5, and 1 μg/mL in this order from the left (regarding the graph shown, the same shall apply to FIGS. 10, 11, 19, 21, and 22).
Figure 10:
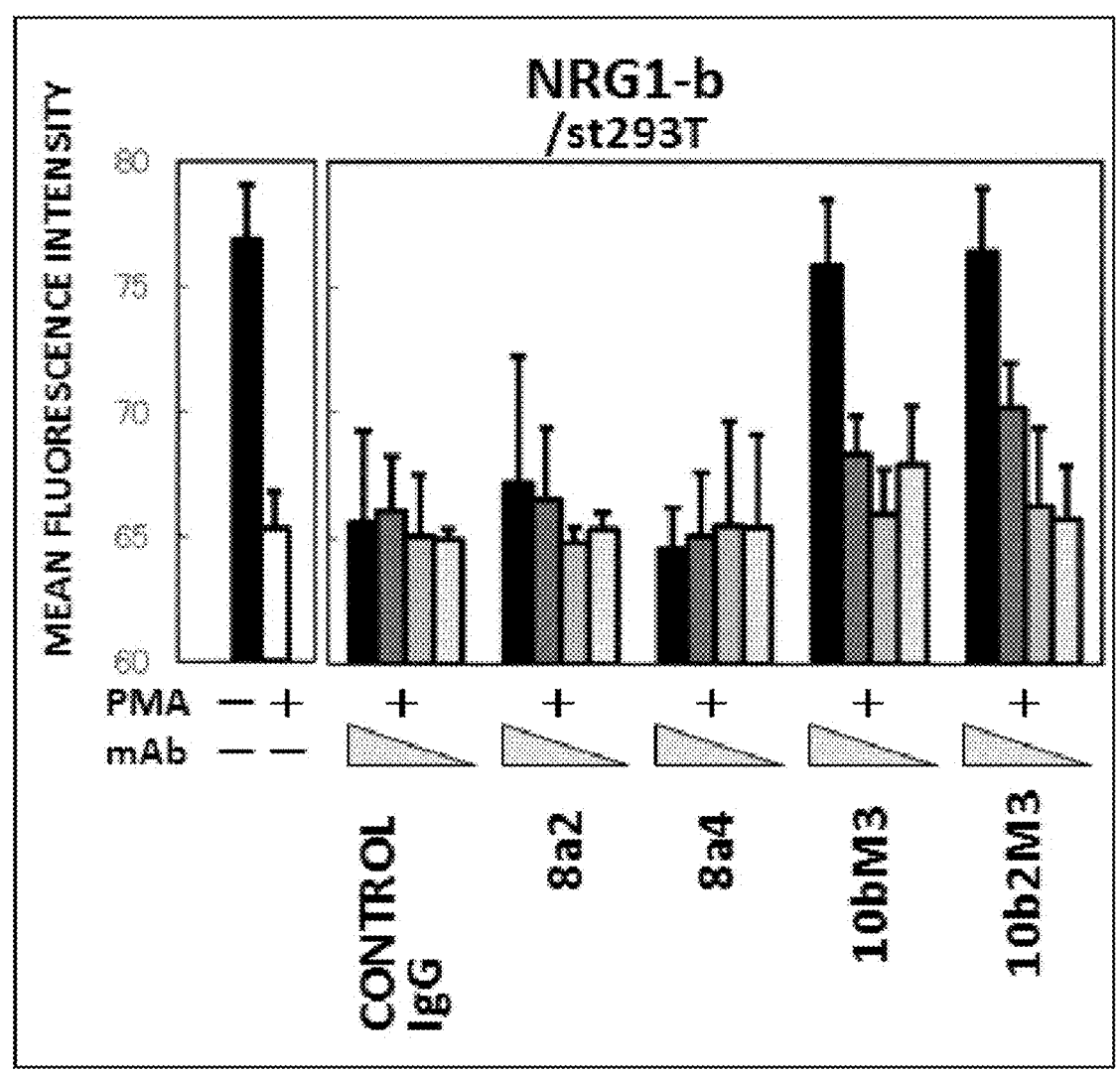
FIG. 10 is a graph for illustrating the result of analyzing by flow cytometry 8a2 and the antibodies of the present invention (8a4, 10bM3, and 10b2M3) for the activity of suppressing the human NRG1-β1 protein cleavage that would otherwise occur by PMA.
Figure 11:
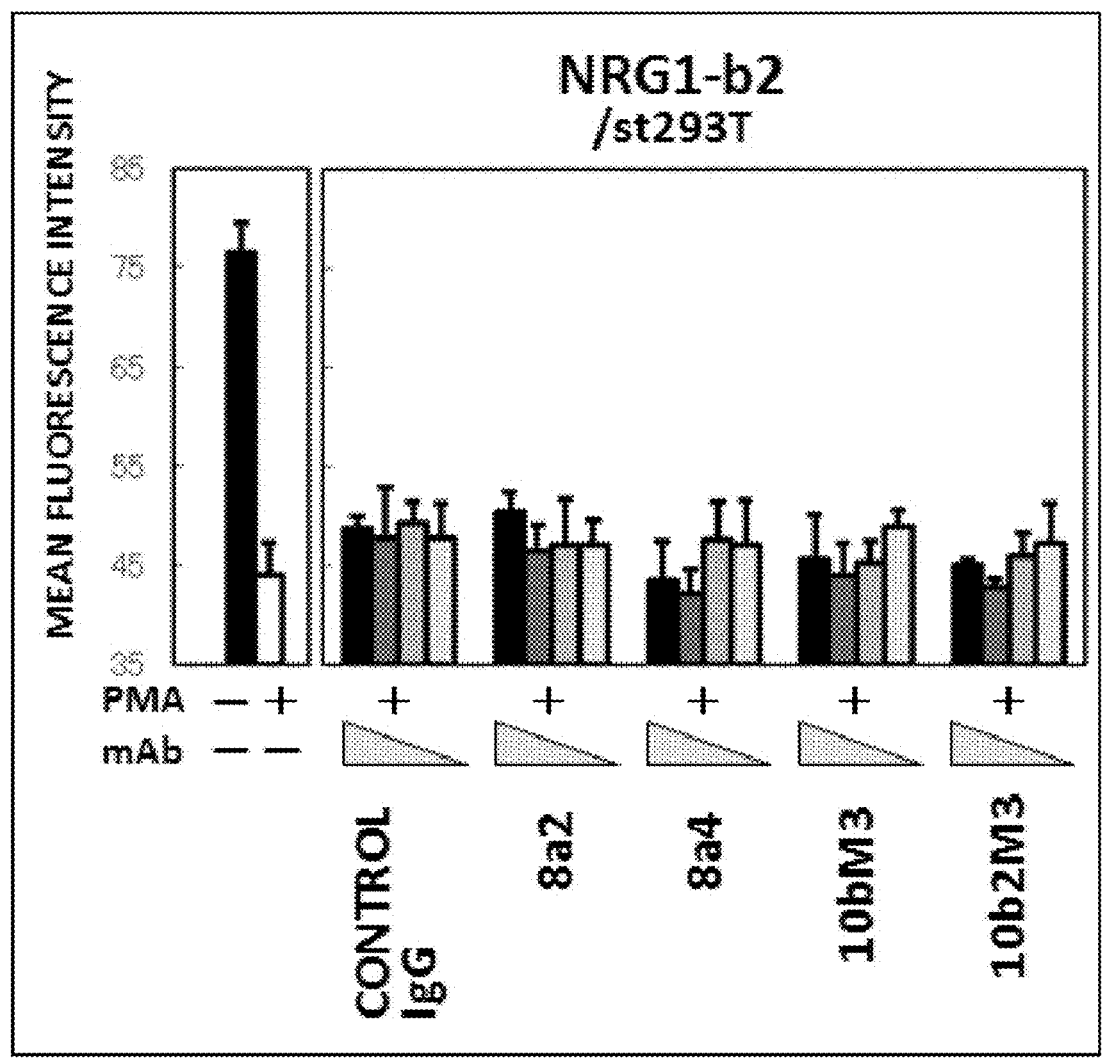
FIG. 11 is a graph for illustrating the result of analyzing by flow cytometry 8a2 and the antibodies of the present invention (8a4, 10bM3, and 10b2M3) for the activity of suppressing the human NRG1-β2 protein cleavage that would otherwise occur by PMA.

After the series of treatments, NRG1 molecules remaining on the surfaces of these cells were analyzed by the flow cytometry to detect the HA tag added to the N-terminus of NRG1. The flow cytometry was performed according to a conventional method using a biotinylated anti-HA tag antibody (manufactured by MBL Co., Ltd.: M132-3) having been diluted to 2 μg/mL as a primary antibody, and PE-labeled streptavidin (manufactured by Invitrogen Corporation: 5866) having been diluted to 1/100 as a secondary antibody. FIGS. 9 to 11 show the obtained result. The vertical axis represents the mean fluorescence intensity in the flow cytometry. Moreover, the value of each sample is an average of the result of measuring 3 wells.

As shown in FIGS. 9 to 11, it was demonstrated that 8a4 inhibited the cleavage of HA-NRG1-a/st293T in a concentration dependent manner, and that 10bM3 and 10b2M3 inhibited the cleavage of HA-NRG1-b/st293T in a concentration dependent manner. In other words, it was revealed that 8a4, 10bM3, and 10b2M3 capable of recognizing an isoform specific region (the region at positions 221 to 234 of the human NRG1-α protein or the region at positions 213 to 239 (or positions 232 to 239) of the human NRG1-β1 protein) had a cleavage inhibitory activity.

<Evaluation 2 of NRG1-Cleavage Inhibitory Activities of Obtained Antibodies>

The anti-NRG1 antibodies obtained in Example 1 (8a2, 8a5, 8a17, 8a18, 8a7, 8a6, 13a3, 8a4, and 10bM3) were used to analyze a correlation between the epitopes for these antibodies and the NRG1-cleavage inhibitory activities.

8a2, 8a5, 8a17, 8a18, and 8a7 are antibodies capable of binding to NRG1-α and NRG1-β1. The epitopes for 8a2, 8a5, 8a17, and 8a18 are all located in a region on the N-terminal side of the EGF domain. The epitope for 8a7 is located in a common region of NRG1-α and NRG1-β1 in the EGF domain.

8a6, 13a3, and 8a4 are antibodies capable of specifically binding to NRG1-α. Both of the epitopes for 8a6 and 13a3 are located in a region on the C-terminal side of the EGF domain (the region has a low homology with NRG1-α and NRG1-β1). The epitope for 8a4 is located in the region at positions 221 to 234 of the human NRG1-α protein as described above.

As described above, 10bM3 is an antibody capable of specifically binding to NRG1-β1, and its epitope is located in the region at positions 213 to 239 (or positions 232 to 239) of the human NRG1-β1 protein.

Note that these anti-NRG1 antibodies were identified by the methods described in Examples 2 and 3. Moreover, the NRG1-cleavage inhibitory activities of these anti-NRG1 antibodies were evaluated using the same method as described above. To be more specific, the HA-NRG1-a/st293T or HA-NRG1-b/st293T was seeded into a 48-well microplate in an amount of 200000 cells per well, and cultured at 37° C. for 6 hours. After it was confirmed that the cells adhered to the bottom surface of the plate, the medium was replaced with a DMEM medium containing no serum, and the resultant was further cultured for 15 hours.

Next, the medium was replaced with a medium to which one of the anti-NRG1 antibodies or a control antibody (MBL Co., Ltd.: M075-3) had been added, and incubated at 37° C. for 120 minutes. In this event, the antibody concentration was set to two levels of 100 and 10 μg/mL, and the amount of the medium per well was 250 μL. Subsequently, a medium supplemented with PMA having been adjusted to 200 nM was added in an amount of 250 μL per well and mixed together, so that PMA was added at a final concentration of 100 nM. After cultured at 37° C. for 30 minutes, the cells were collected by pipetting.

Figure 12:
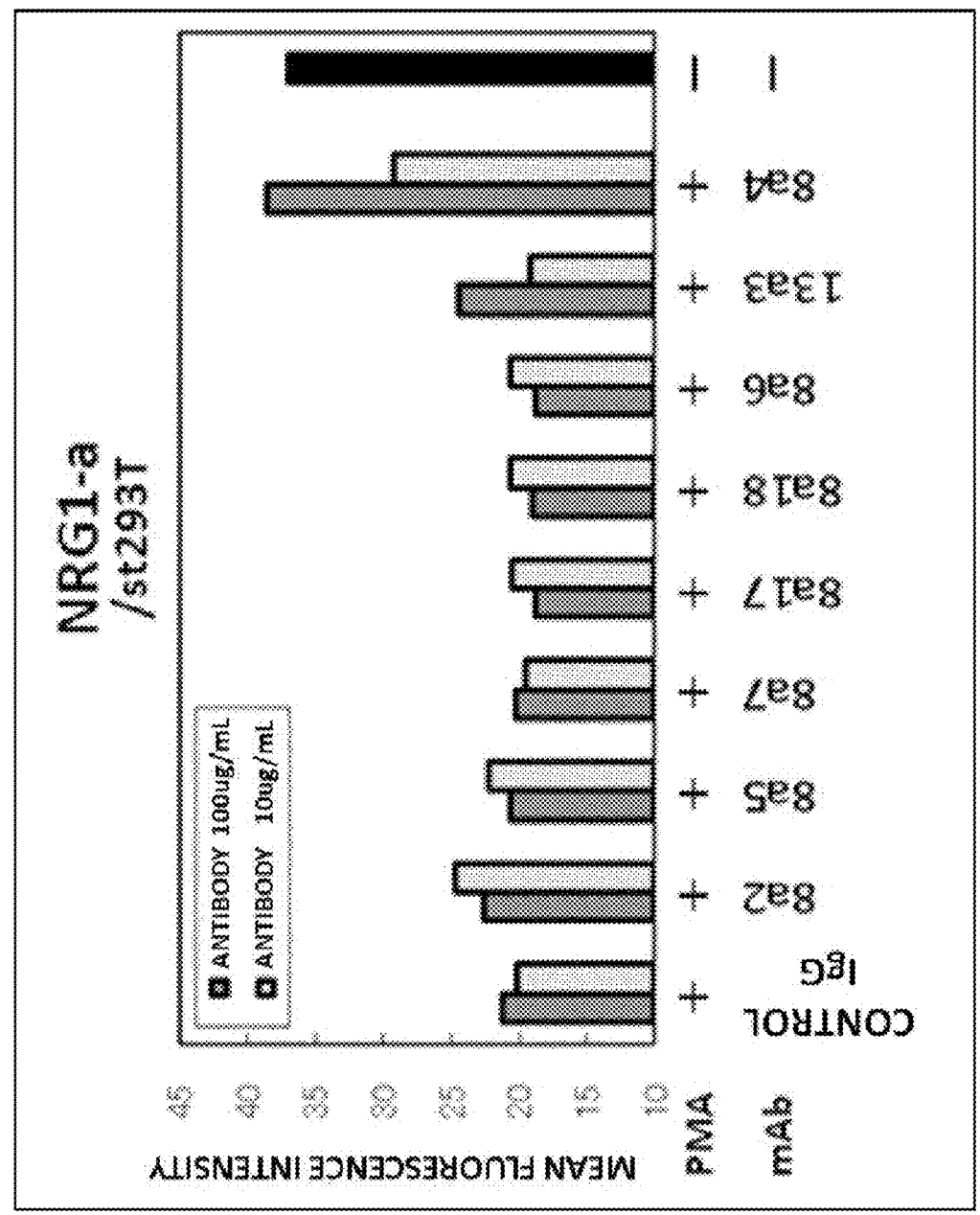
FIG. 12 is a graph for illustrating the result of analyzing by flow cytometry 8a2, 8a5, 8a7, 8a17, 8a18, 8a6, 13a3, and the antibody of the present invention (8a4) for the activity of suppressing the human NRG1-α protein cleavage that would otherwise occur by PMA.
Figure 13:
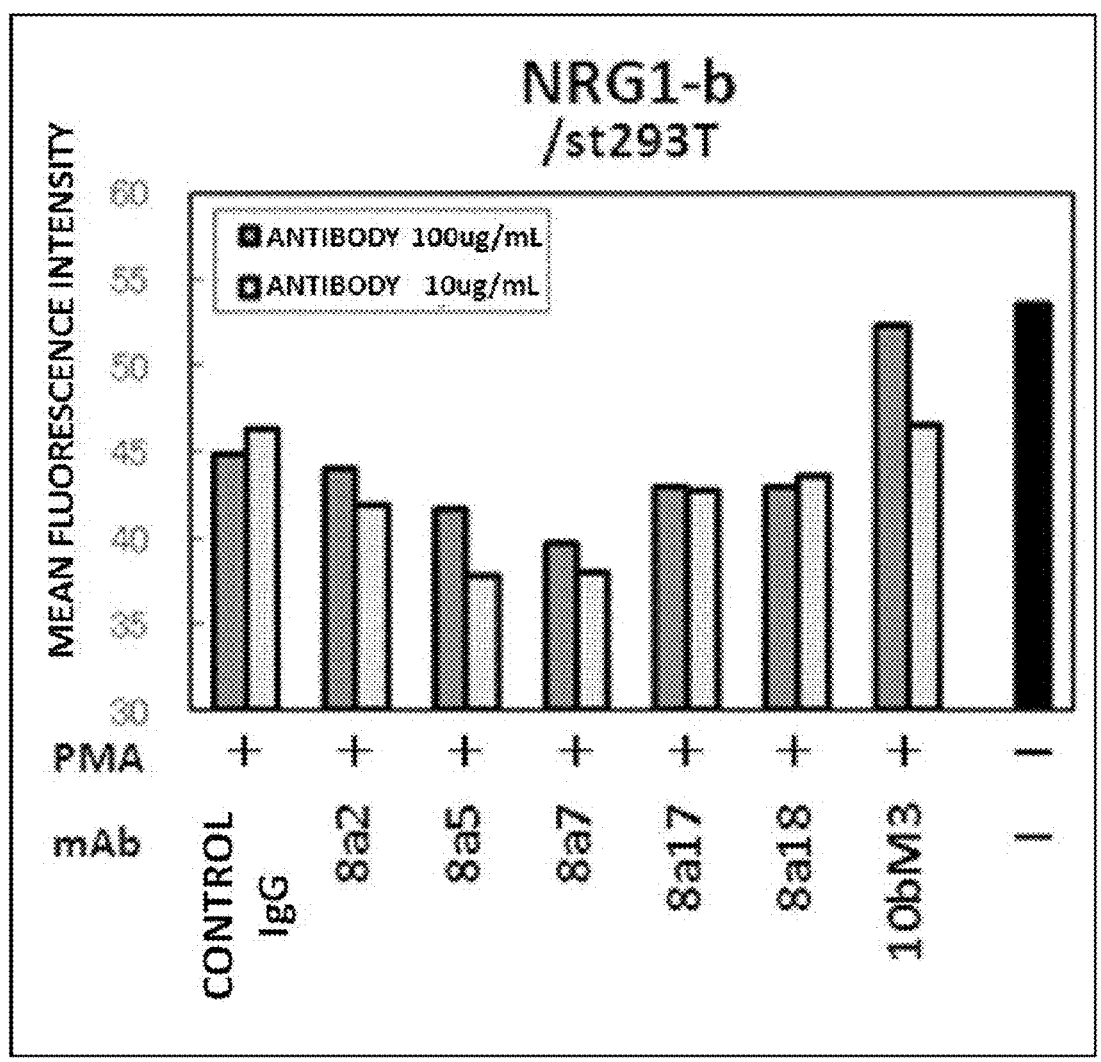
FIG. 13 is a graph for illustrating the result of analyzing by flow cytometry 8a2, 8a5, 8a7, 8a17, 8a18, and the antibody of the present invention (10bM3) for the activity of suppressing the human NRG1-β1 protein cleavage that would otherwise occur by PMA.

After the series of treatments, NRG1 molecules remaining on the surfaces of these cells were analyzed by the flow cytometry to detect the HA tag added to the N-terminus of NRG1. The flow cytometry was performed according to a conventional method using a biotinylated anti-HA tag antibody (manufactured by MBL Co., Ltd.: M132-3) having been diluted to 2 μg/mL as a primary antibody, and PE-labeled streptavidin (manufactured by Invitrogen Corporation: 5866) having been diluted to 1/100 as a secondary antibody. FIGS. 12 and 13 show the obtained result. The vertical axis represents the mean fluorescence intensity in the flow cytometry.

As shown in FIGS. 12 and 13, it was demonstrated that 8a4 inhibited the cleavage of the human NRG1-α protein in a concentration dependent manner, and that 10bM3 inhibited the cleavage of the human NRG1-β1 in a concentration dependent manner, like the result described above. On the other hand, none of the antibodies (8a2, 8a5, 8a17, 8a18, 8a7, 8a6, and 13a3) capable of recognizing regions other than the region at positions 221 to 234 of the human NRG1-α protein and the region at positions 213 to 239 of the human NRG1-β1 protein were observed to have a cleavage inhibitory activity against the NRG1 proteins. Particularly, such an activity was not confirmed even from 8a6 and 13a3 whose epitopes were located in a region very close to the region at positions 221 to 234 of the human NRG1-α protein. Thus, it was confirmed that the region at positions 221 to 234 of the human NRG1-α protein and the region at positions 213 to 239 of the human NRG1-β1 protein were important recognition sites for an antibody to inhibit NRG1 protein cleavage.

Example 6

Evaluation of NRG1 Neutralizing Activities of Obtained Antibodies

Whether or not the obtained antibodies were capable of specifically suppressing signal transduction in which any one of the human NRG1-α protein and the human NRG1-β1 protein was involved was evaluated. In other words, whether or not the obtained antibodies were capable of suppressing phosphorylation of an ErbB3 protein in a cancer cell that would otherwise occur specifically in response to a stimulus of these proteins was evaluated by the following method.

Whether the obtained anti-NRG1 antibodies were capable of inhibiting phosphorylation of ErbB3 induced when stimulated with NRG1, in other words, whether or not the anti-NRG1 antibodies had an activity of neutralizing NRG1, was analyzed by the western blot method using a human breast cancer culture cell line MCF7 (manufactured by ATCC: HTB-22). MCF7 cultured using DMEM-10% FBS (containing Penicillin-Streptomycin), was seeded into a 6-well plate in an amount of 250000 cells per well, and cultured at 37° C. for 6 hours. After it was confirmed that the cells adhered to the bottom surface of the plate, the medium was replaced with a DMEM medium containing no serum, and the resultant was further cultured for 24 hours.

Then, to this, NRG1-a and NRG1-b recombinant proteins (manufactured by R&D Systems, Inc.: 296-HR/CF and 396-HB/CF) and the anti-NRG1 antibody having been incubated at 37° C. for 60 minutes were added in an amount of 500 μL per well. In this event, the recombinant protein concentration was 100 ng/mL (NRG1-α) or 5 ng/mL (NRG1-b), and the antibody concentration was set to four levels of 50, 10, 5, and 0 μg/mL.

After the resultant was cultured at 37° C. for 30 minutes, the cells were collected using SDS sample buffer (62.5 mM Tris-HCL [pH=6.8], 5% Glycerol, 2% SDS, 0.003% BPB, 5% 2-mercaptoethanol) in an amount of 200 μL per well.

Figure 14:
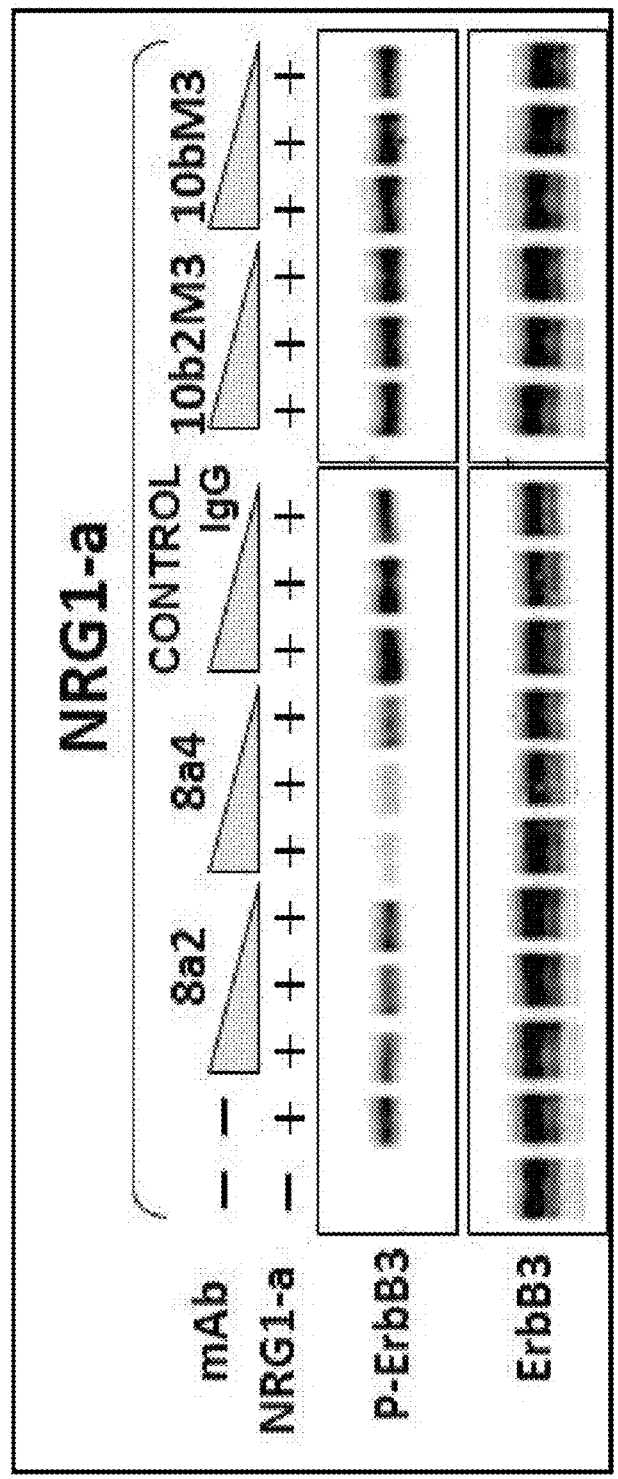
FIG. 14 shows photographs for illustrating the result of analyzing by western blot 8a2 and the antibodies of the present invention (8a4, 10bM3, and 10b2M3) for the activity of suppressing ErbB3 phosphorylation that would otherwise be induced by the human NRG1-α protein. In the figure, "ErbB3" shows the amount of the ErbB3 protein in each cell, while "P-ErbB3" shows the amount of the ErbB3 protein phosphorylated in each cell. Moreover, in each group, "mAb" shows that the concentration of each antibody added was 50, 10, and 5 μg/mL in this order from the left (regarding the representation in the figure, the same shall apply to FIG. 15).
Figure 15:
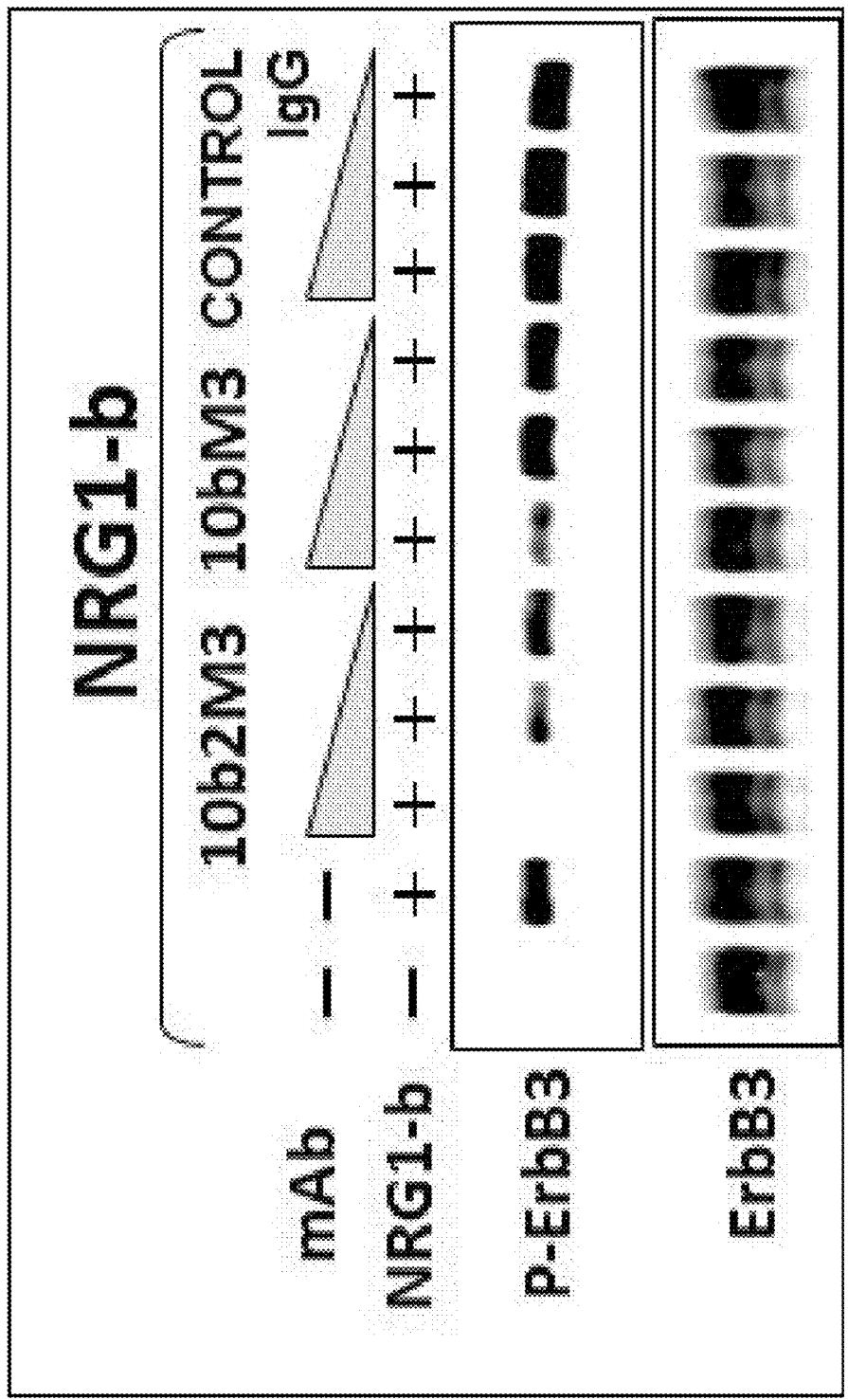
FIG. 15 shows photographs for illustrating the result of analyzing by western blot the antibodies of the present invention (10bM3 and 10b2M3) for the activity of suppressing ErbB3 phosphorylation that would otherwise be induced by the human NRG1-β1 protein.

The collected cell sample was heat treated, and then subjected to SDS-PAGE in an amount of 15 μL at a time, followed by the western blot using an anti-phosphorylated ErbB3 rabbit antibody (manufactured by Cell Signaling Technology, Inc.: #4791S) or an anti-ErbB rabbit antibody (manufactured by Cell Signaling Technology, Inc.: #4754) having been diluted to 1/1000, and an HRP-labeled anti-rabbit IgG antibody (manufactured by MBL Co., Ltd.: 458) having been diluted to 1/5000. FIGS. 14 and 15 show the obtained result.

As shown in FIGS. 14 and 15, 8a4 inhibited the ErbB3 phosphorylation attributable to NRG1-a, while 10bM3 and 10b2M3 inhibited the ErbB3 phosphorylation attributable to NRG1-b, in concentration dependent manners. In other words, it was revealed that 8a4, 10bM3, and 10b2M3 had an NRG1 neutralizing activity.

Example 7

Isolation of Heavy Chain and Light Chain Variable Region Genes of 8a4, 10bM3, and 10b2M3 Antibodies, and Identification of CDRs The heavy chain and light chain variable region genes of the antibodies of the present invention (8a4, 10bM3, and 10b2M3) were isolated by the following method. Further, the CDRs in these variable regions were identified.

The hybridoma was cultured, and the total RNA was extracted by a general method. Next, the cDNA was obtained by a 5'-RACE method using GeneRacer Kit (manufactured by Invitrogen Corporation: L1502-01). Using this cDNA as a template, PCR was carried out (35 cycles each consisting of [94° C. for 30 seconds, 57° C. for 30 seconds, 72° C. for 50 seconds]) with Platinum Taq DNA Polymerase High Fidelity (manufactured by Invitrogen Corporation: 11304-029) using GeneRacer 5' Primer (5'-CGACTGGAG-CACGAGGACACTGA-3' (SEQ ID NO: 54)) and CH1 (mouse IgG1 constant region 1) 3' Primer (5'-AATTTTCT-TGTCCACCTGG-3' (SEQ ID NO: 55)), so that the gene (cDNA) of the antibody heavy chain variable region was amplified. On the other hand, as to the antibody light chain also, PCR was carried out in the same manner using GeneRacer 5' Primer and Ck (κ constant region) 3' Primer (5'-CTAACACTCATTCCTGTTGAAGCTCT-3' (SEQ ID NO: 56)), so that the gene (cDNA) was amplified. Each of the amplified gene fragments was cloned in pT7Blue T-Vector (manufactured by Novagen Inc.: 69820), and analyzed for the sequence using an automated sequencer (manufactured by Applied Biosystems Inc.). Then, amino acids encoded by the obtained base sequences and the sequence of each CDR were determined. The results are as follows.

```
<8a4 heavy chain variable region>
                                       (SEQ ID NO: 10)
EVQLQQSGADLVRPGASVKLSCTASGFNIKDDYIHWVKQRPEQGLEWIG

WIDPENGDTEYASQFQGKATITADTSSNTAYLQLRSLTSEDTAVYYCTT

SDHRAWFAFWGLGTLVTVSS

<CDR1 of 8a4 heavy chain variable region>
                                        (SEQ ID NO: 7)
DDYIH <CDR2 of 8a4 heavy chain variable region>
                                        (SEQ ID NO: 8)
WIDPENGDTEYASQFQG <CDR3 of 8a4 heavy chain variable region>
                                        (SEQ ID NO: 9)
SDHRAWFAF
```

-continued
<8a4 light chain variable region>
(SEQ ID NO: 6)
DVLMTQTPLSLPVSLGDQASISCRSSQTIVHRNGNTYLEWYLQKPGQSP

KLLIYRVSNRFSGVPDRFSGSGSGTDFTLKISRVEAEDLGVYYCFQGSH

VPLTFGAGTKL

<CDR1 of 8a4 light chain variable region>
(SEQ ID NO: 3)
RSSQTIVHRNGNTYLE

<CDR2 of 8a4 light chain variable region>
(SEQ ID NO: 4)
RVSNRFS

<CDR3 of 8a4 light chain variable region>
(SEQ ID NO: 5)
FQGSHVPLT

<10bM3 heavy chain variable region>
(SEQ ID NO: 18)
EVQLVESGGGLVKPGGSRKLSCAASGFTFSDYGIHWVRQAPEKGLEWLA

YISSGSSTIYYADTVKGRFTISRDNAKNTLFLQMTSLRSEDTAMYYCAR

GSNYVGYYAMDYWGQGTSVTVSS

<CDR1 of 10bM3 heavy chain variable region>
(SEQ ID NO: 15)
DYGIH

<CDR2 of 10bM3 heavy chain variable region>
(SEQ ID NO: 16)
YISSGSSTIYYADTVKG

<CDR3 of 10bM3 heavy chain variable region>
(SEQ ID NO: 17)
GSNYVGYYAMDY

<10bM3 light chain variable region>
(SEQ ID NO: 14)
DIVMTQSPSSLAVTAGEKVTMRCKSSQSLLWSVNQKNYLSWYQQKEGQS

PKLLIYGASIRESWVPDRFTGSGSGTDFTLTISNVHAEDLAVYYCQHNH

GRFLPLTFGGGTKL

<CDR1 of 10bM3 light chain variable region>
(SEQ ID NO: 11)
KSSQSLLWSVNQKNYLS

<CDR2 of 10bM3 light chain variable region>
(SEQ ID NO: 12)
GASIRES

<CDR3 of 10bM3 light chain variable region>
(SEQ ID NO: 13)
QHNHGRFLPLT

<10b2M3 heavy chain variable region>
(SEQ ID NO: 26)
QVQLQQSGPELVKPGASVKISCKASGYAFSSSWMNWVKQRPGKGLEWIG

RIYPGDGDIYYNGKFKGKATLTADKSSSTAYMQLNSLTSEDSAVYFCAR

TFNYPFFAYWGQGTLVTVSS

<CDR1 of 10b2M3 heavy chain variable region>
(SEQ ID NO: 23)
SSWMN

<CDR2 of 10b2M3 heavy chain variable region>
(SEQ ID NO: 24)
RIYPGDGDIYYNGKFKG

<CDR3 of 10b2M3 heavy chain variable region>
(SEQ ID NO: 25)
TFNYPFFAY

-continued
<10b2M3 light chain variable region>
(SEQ ID NO: 22)
DILMTQSPSSLTVSTGEKVTMSCKSSQSLLASANQNNYLAWHQQKPGRS

PKMLIIWASTRVSGVPDRFIGSGSGTDFTLTINSVQAEDLAVYYCQQSY

SAPTTFGAGTKL

<CDR1 of 10b2M3 light chain variable region>
(SEQ ID NO: 19)
KSSQSLLASANQNNYLA

<CDR2 of 10b2M3 light chain variable region>
(SEQ ID NO: 20)
WASTRVS

<CDR3 of 10b2M3 light chain variable region>
(SEQ ID NO: 21)
QQSYSAPTT

Example 8

Preparation of 8a4 Chimeric Antibody, 10bM3 Chimeric Antibody, and 10b2M3 Chimeric Antibody Chimeric antibodies in which the constant regions of the mouse monoclonal antibodies of the present invention (8a4, 10bM3, and 10b2M3) were substituted with one derived from human IgG1 were prepared by the following method.

The following PCR amplification primers were designed based on the gene sequences determined in Example 7, and the antibody variable regions were amplified by PCR. In this event, the secretion signal sequence was converted into a sequence recommended by Lonza Group, and restriction enzyme recognition sequences were added to ends of the amplified fragments (a HindIII recognition sequence and an XhoI recognition sequence were added for the heavy chain variable regions, HindIII and BsiWI recognition sequences were added for the light chain variable regions).

<8a4 heavy chain>
8a4_VH_F_signal_HindIII:
5'-ATATA<u>AAGCTT</u>ACCATGGAATGGAGCTGGGTGTTCCTGTTCTTTC

TGTCCGTGACCACAGGCGTGCATTCTGAGGTTCAGCTGCAGCAGTCTG

GG-3'
(SEQ ID NO: 57, the underline indicates the HindIII recognition sequence)

8a4_VH_R_XhoI:
5'-ATATA<u>CTCGAG</u>ACAGTGACCAGAGTCCCTAGGCC-3'
(SEQ ID NO: 58, the underline indicates the XhoI recognition sequence)

<8a4 light chain>
8a4_VK_F_signal_HindIII:
5'-ATATA<u>AAGCTT</u>ACCATGTCTGTGCCTACCCAGGTGCTGGGACTGC

TGCTGCTGTGGCTGACAGACGCCCGCTGTGATGTTTTGATGACCCAAA

CTCCACTCTCC-3'
(SEQ ID NO: 59, the underline indicates the HindIII recognition sequence)

8a4/10b2M3_VK_R_BsiWI:
5'-ATATA<u>CGTACG</u>TTTTATTTCCAGCTTGGTCCCAGCACCGAAC-3'
(SEQ ID NO: 60, the underline indicates the BsiWI recognition sequence)

-continued

<10bM3 heavy chain>
10bM3_VH_F_signal_HindIII:
5'-ATATAAAGCTTACCATGGAATGGAGCTGGGTGTTCCTGTTCTTTC

TGTCCGTGACCACAGGCGTGCATTCTGAGGTGCAGCTGGTGGAGTCTG

GG-3'
(SEQ ID NO: 61, the underline indicates the
HindIII recognition sequence)

10bM3_VH_R_XhoI:
5'-ATATACTCGAGACGGTGACTGAGGTTCCTTGACC-3'
(SEQ ID NO: 62, the underline indicates the XhoI
recognition sequence)

<10bM3 light chain>
10bM3_VK_F_signal_HindIII:
5'-ATATAAAGCTTACCATGTCTGTGCCTACCCAGGTGCTGGGACTGC

TGCTGCTGTGGCTGACAGACGCCCGCTGTGACATTGTGATGACCCAGT

CTCC-3'
(SEQ ID NO: 63, the underline indicates the
HindIII recognition sequence)

10bM3_VK_R_BsiWI:
5'-ATATACGTACGTTTTAGCTCCAACTTGGTCCCACCACC-3'
(SEQ ID NO: 64, the underline indicates the BsiWI
recognition sequence)

<10b2M3 heavy chain>
10b2M3_VH_F_signal_HindIII:
5'-ATATAAAGCTTACCATGGAATGGAGCTGGGTGTTCCTGTTCTTTC

TGTCCGTGACCACAGGCGTGCATTCTCAGGTTCAGCTGCAGCAGTCTG

G-3'
(SEQ ID NO: 65, the underline indicates the
HindIII recognition sequence)

10b2M3_VH_XhoI:
5'-TAGCGCTCGAGACAGTGACCAGAGT-3'
(SEQ ID NO: 66, the underline indicates the XhoI
recognition sequence)

<10b2M3 light chain>
10b2M3_VK_F_signal_HindIII:
5'-ATATAAAGCTTACCATGTCTGTGCCTACCCAGGTGCTGGGACTGCT

GCTGCTGTGGCTGACAGACGCCCGCTGTGACATTTTGATGACTCAGTCT

CC-3'
(SEQ ID NO: 67, the underline indicates the
HindIII recognition sequence)

8a4/10b2M3_VK_R_BsiWI:
5'-ATATACGTACGTTTTATTTCCAGCTTGGTCCCAGCACCGAAC-3'
(SEQ ID NO: 60, the underline indicates the BsiWI
recognition sequence).

The obtained PCR products were cleaved with the above restriction enzyme, and inserted by a conventional method into human IgG1 antibody producing vectors of Lonza Group incorporating the human IgG1 constant region. These vectors were used to establish chimeric antibody-producing cell lines based on a protocol recommended by Lonza Group. From the culture supernatants, chimeric antibodies (an 8a4 chimeric antibody, a 10bM3 chimeric antibody, and a 10b2M3 chimeric antibody) were purified using Protein A. Regarding the chimeric antibodies obtained in this manner, the 8a4 chimeric antibody, the 10bM3 chimeric antibody, and the 10b2M3 chimeric antibody are also referred to as ch-8a4, ch-10bM3, and ch-10b2M3, respectively, hereinbelow.

Example 9

Figure 16:
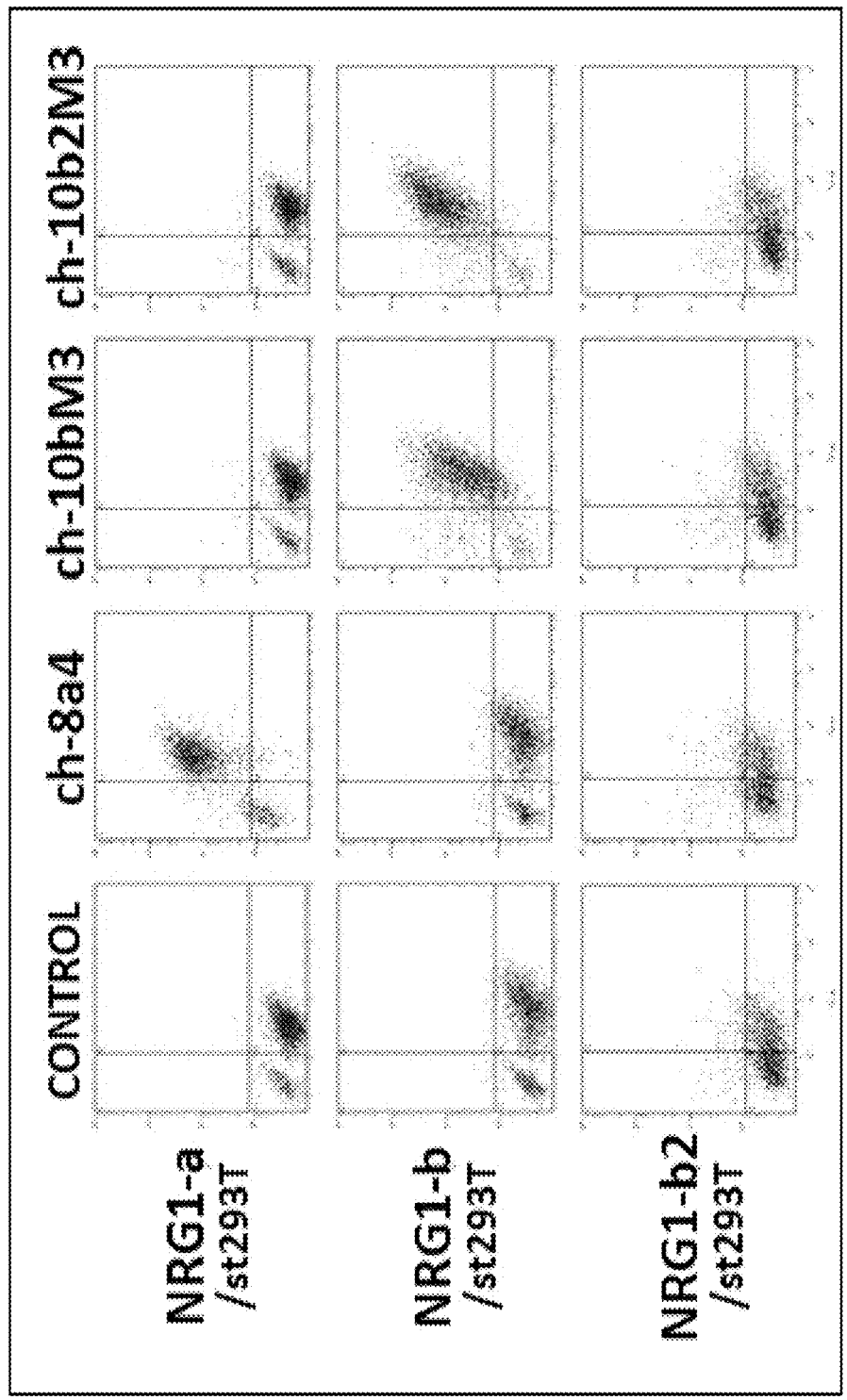
FIG. 16 shows dot plot diagrams for illustrating the result of analyzing by flow cytometry the degree of the binding between chimeric antibodies of the present invention (ch-8a4, ch-10bM3, and ch-10b2M3) and NRG1-a/st293T, NRG1-b/st293T, or NRG1-b2/st293T.

Reactivities of 8a4 Chimeric Antibody, 10bM3 Chimeric Antibody, and 10b2M3 Chimeric Antibody The reactivities of the obtained chimeric antibodies with NRG1 were confirmed by the flow cytometry and the enzyme-linked immunosorbent assay (ELISA). The flow cytometry was performed by the same method as above. Note that, in the flow cytometry, each of the chimeric antibodies or a control antibody having been diluted to 5 μg/mL was used as a primary antibody, and a PE-labeled anti-human IgG antibody (manufactured by Beckman Coulter, Inc.: IM0550) having been diluted to 1/100 was used as a secondary antibody. FIG. 16 shows the obtained result.

Figure 17:
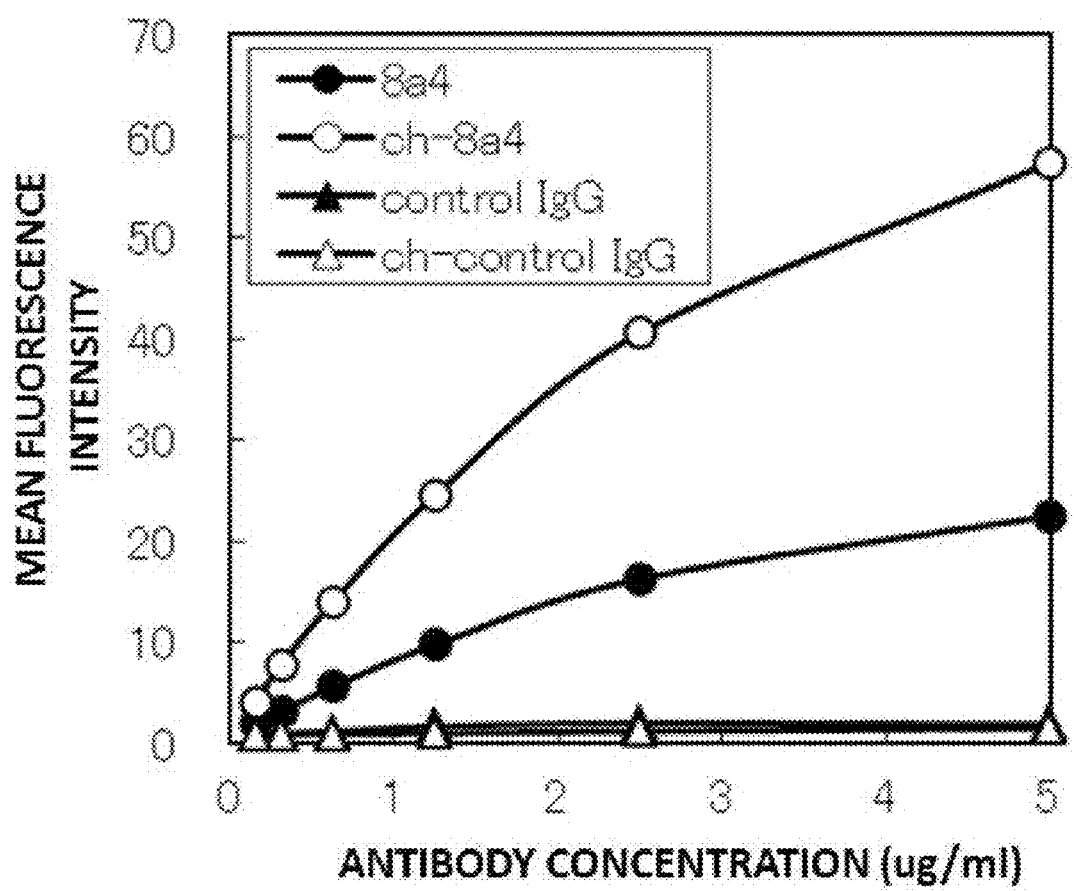
FIG. 17 is a graph for illustrating the result of analyzing by flow cytometry the degree of the binding of 8a4 and ch-8a4 to the human NRG1-α protein.

As apparent from the result shown in FIG. 16, it was demonstrated that ch-8a4 reacted with NRG1-a, while ch-10bM3 and ch-10b2M3 reacted with NRG1-b, so that the activities were maintained. Moreover, it was observed that the reactivity of ch-8a4 was improved in comparison with that before the chimerization (8a4). For this reason, data on the mean fluorescence intensity was further obtained under low antibody concentration condition. To be more specific, each of 8a4, ch-8a4, and a control antibody was serially diluted with PBS with a maximum concentration of 5 μg/mL, and the mean fluorescence intensity at each concentration was analyzed in the flow cytometry. The result revealed as shown in FIG. 17 that 8a4 unexpectedly had the reactivity improved by the chimerization.

Figure 18:
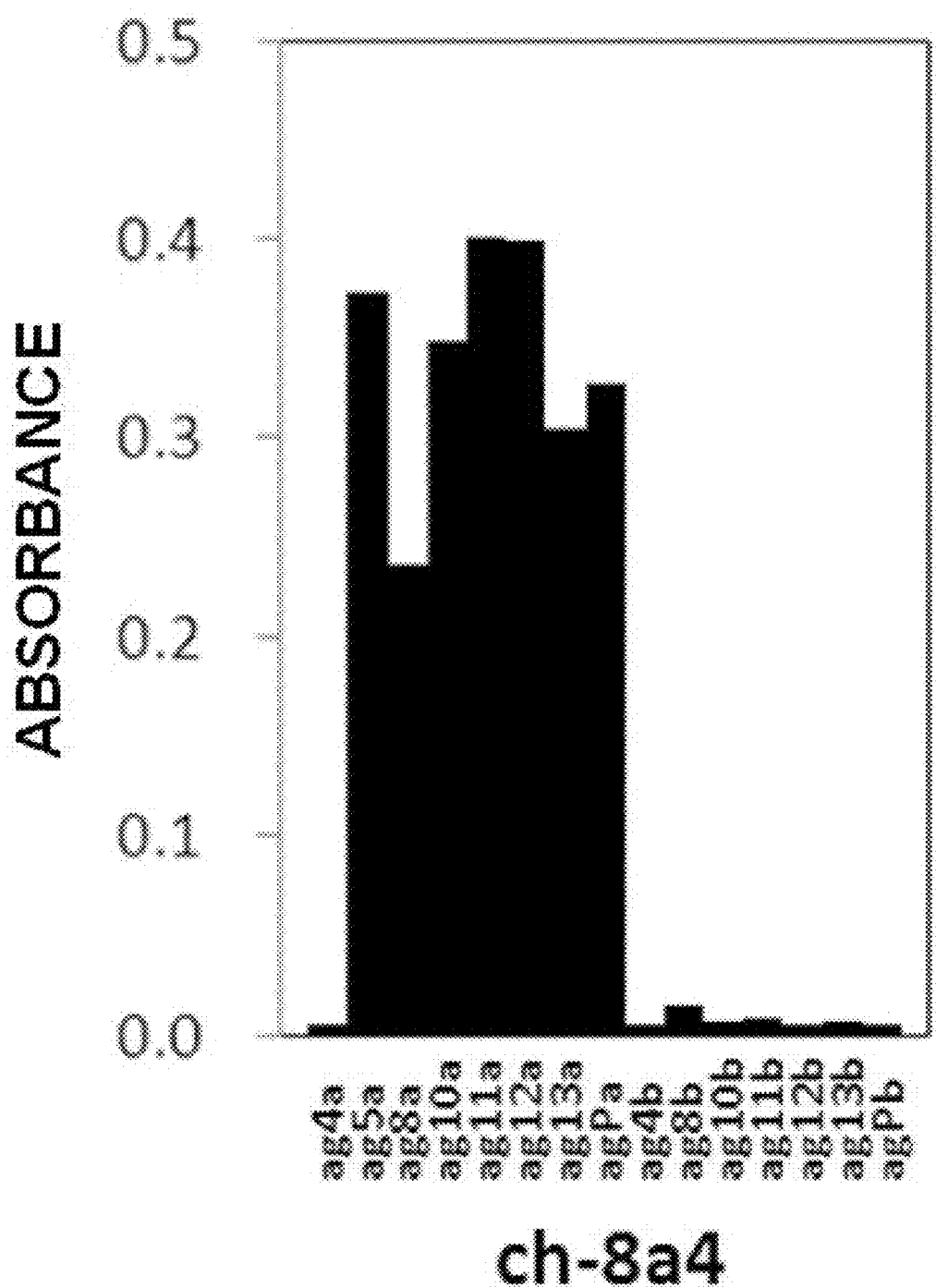
FIG. 18 is a graph for illustrating the result of analyzing by ELISA the degree of the binding of ch-8a4 to the partial-length human NRG1-α proteins (ag4a to ag13a, and agPa) and the partial-length human NRG1-β1 proteins (ag4b to ag13b, and agPb).
Figure 19:
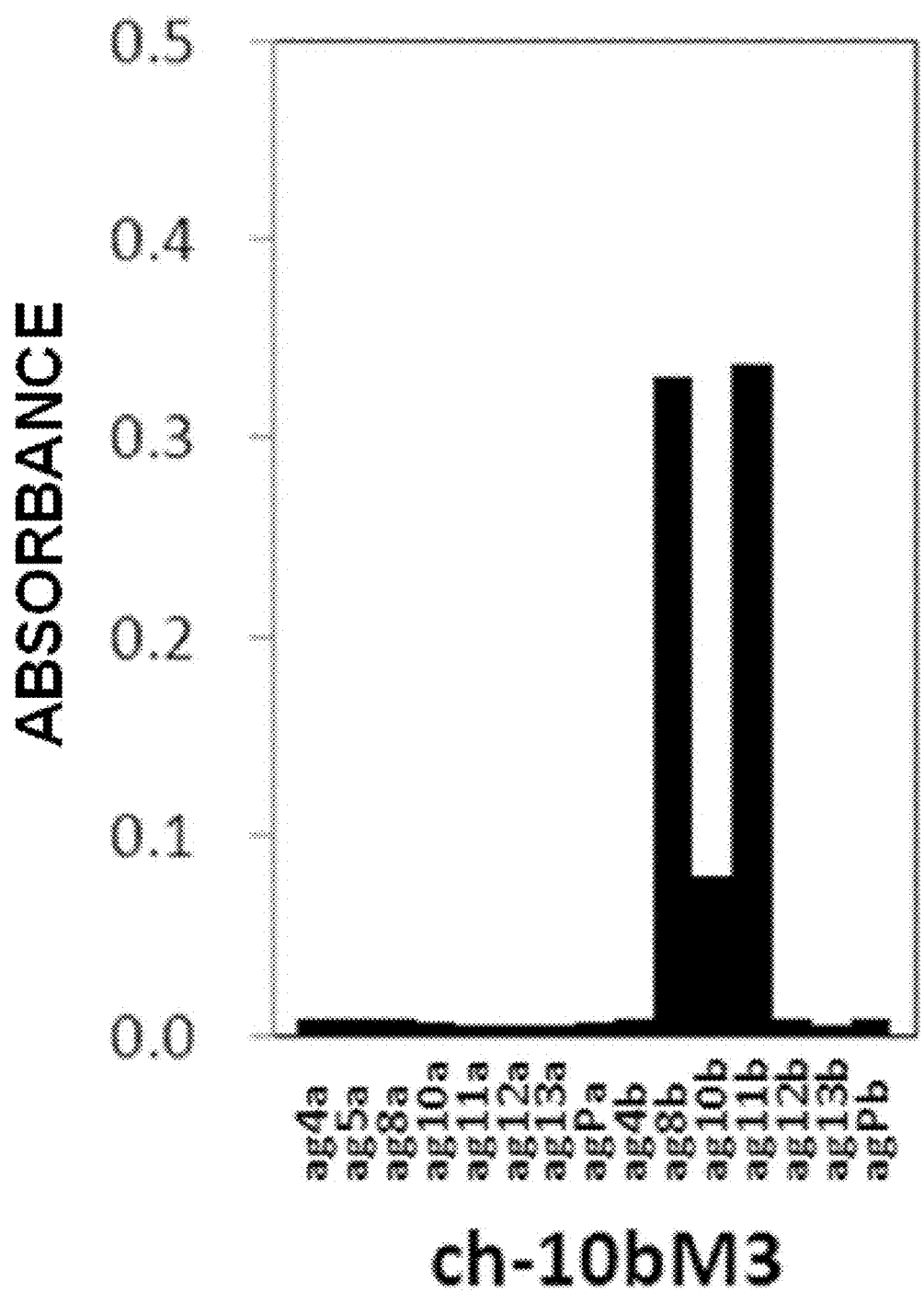
FIG. 19 is a graph for illustrating the result of analyzing by ELISA the degree of the binding of ch-10bM3 to the partial-length human NRG1-α proteins and the partial-length human NRG1-β1 proteins.
Figure 20:
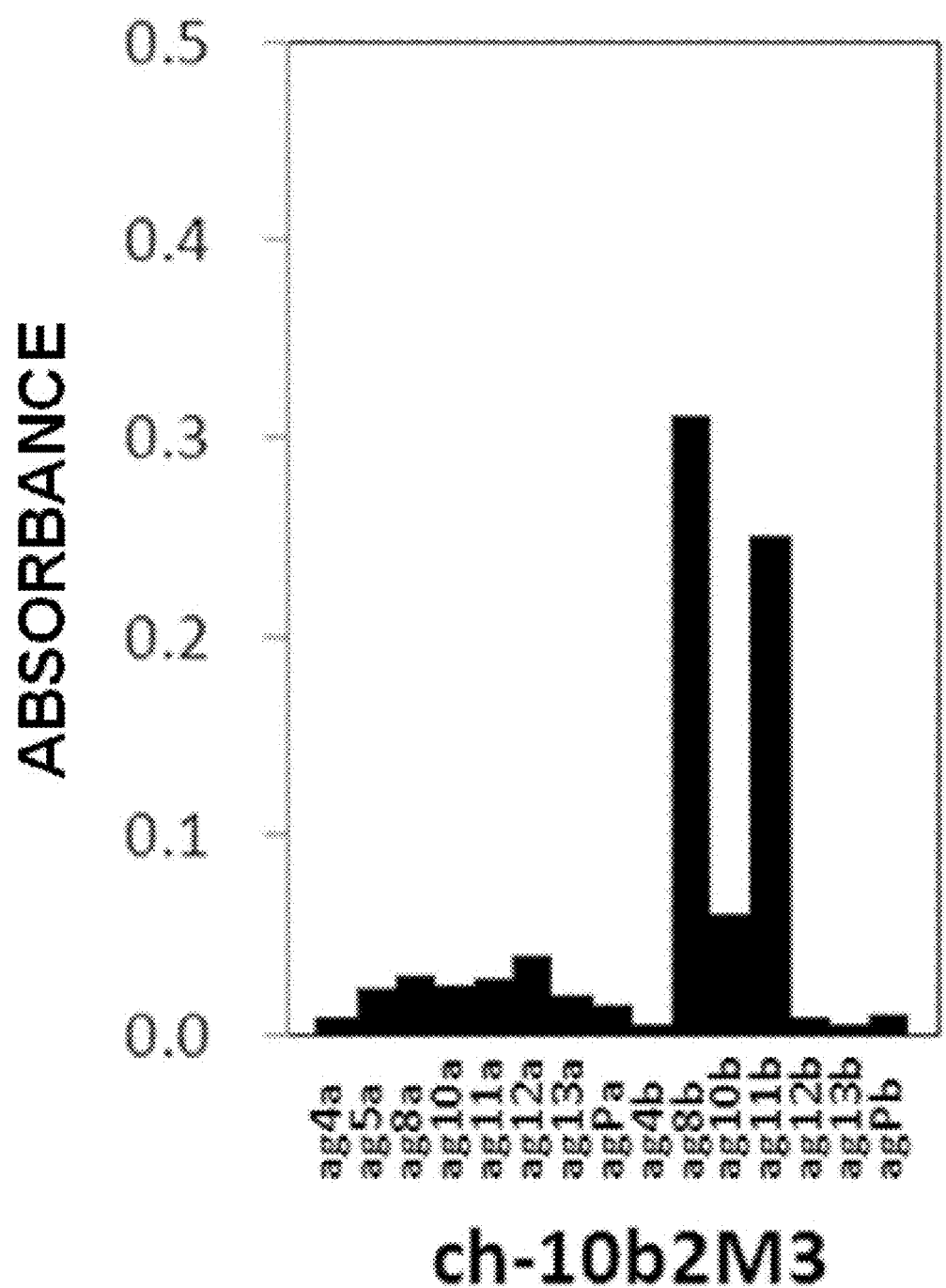
FIG. 20 is a graph for illustrating the result of analyzing by ELISA the degree of the binding of ch-10b2M3 to the partial-length human NRG1-α proteins and the partial-length human NRG1-β1 proteins.

Moreover, the enzyme-linked immunosorbent assay (ELISA) was performed by the same method as above using each chimeric antibody having been diluted to 5 μg/mL as a primary antibody, and an HRP-labeled anti-human IgG antibody (manufactured by MBL Co., Ltd.: 206) having been diluted to 1/5000 as a secondary antibody. The result revealed as shown in FIGS. 18 to 20 that each chimeric antibody had a reaction specificity equivalent to the original mouse antibody.

Example 10

Figure 21:
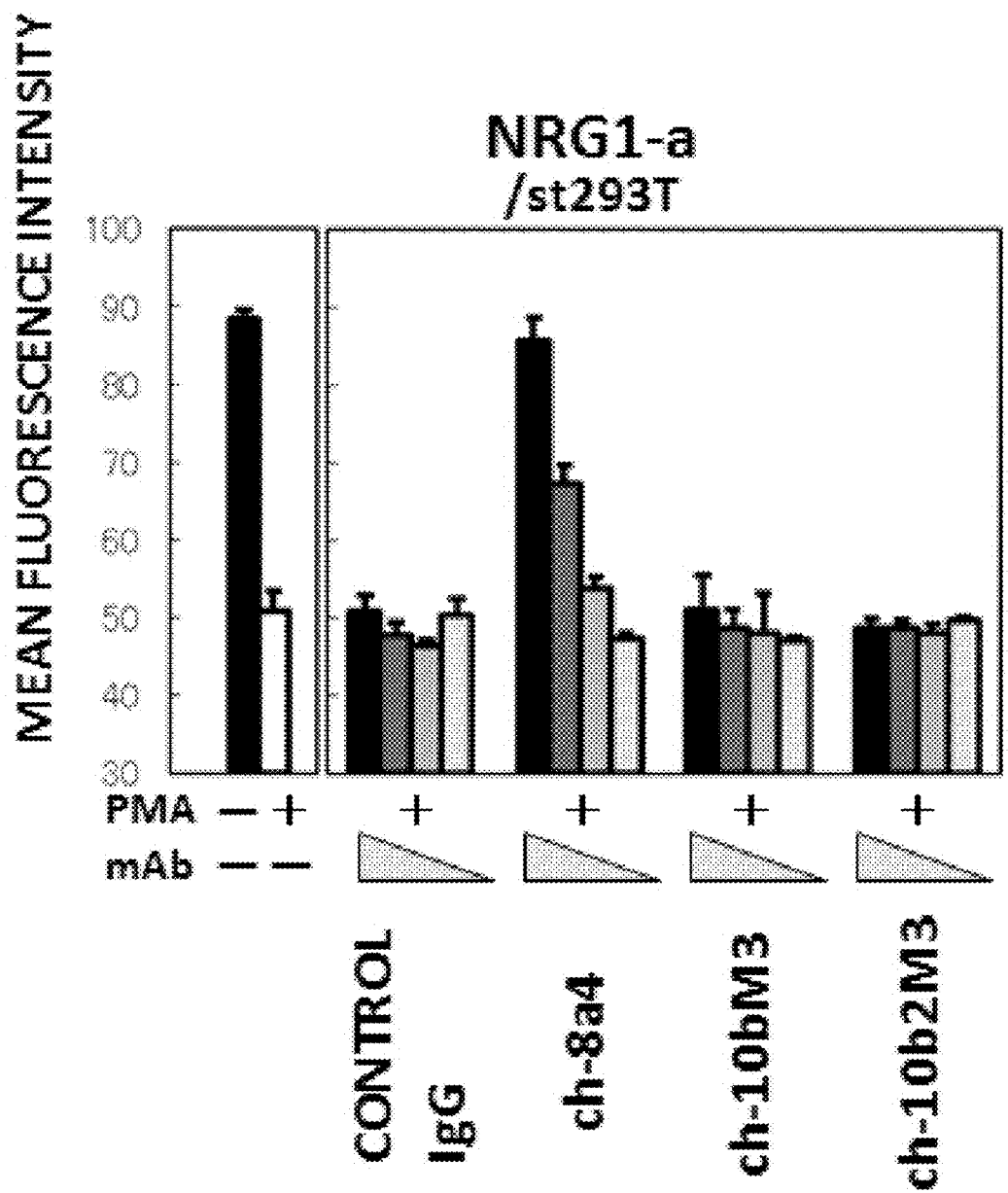
FIG. 21 is a graph for illustrating the result of analyzing by flow cytometry the chimeric antibodies of the present invention (ch-8a4, ch-10bM3, and ch-10b2M3) for the activity of suppressing the human NRG1-α protein cleavage that would otherwise occur by PMA.
Figure 22:
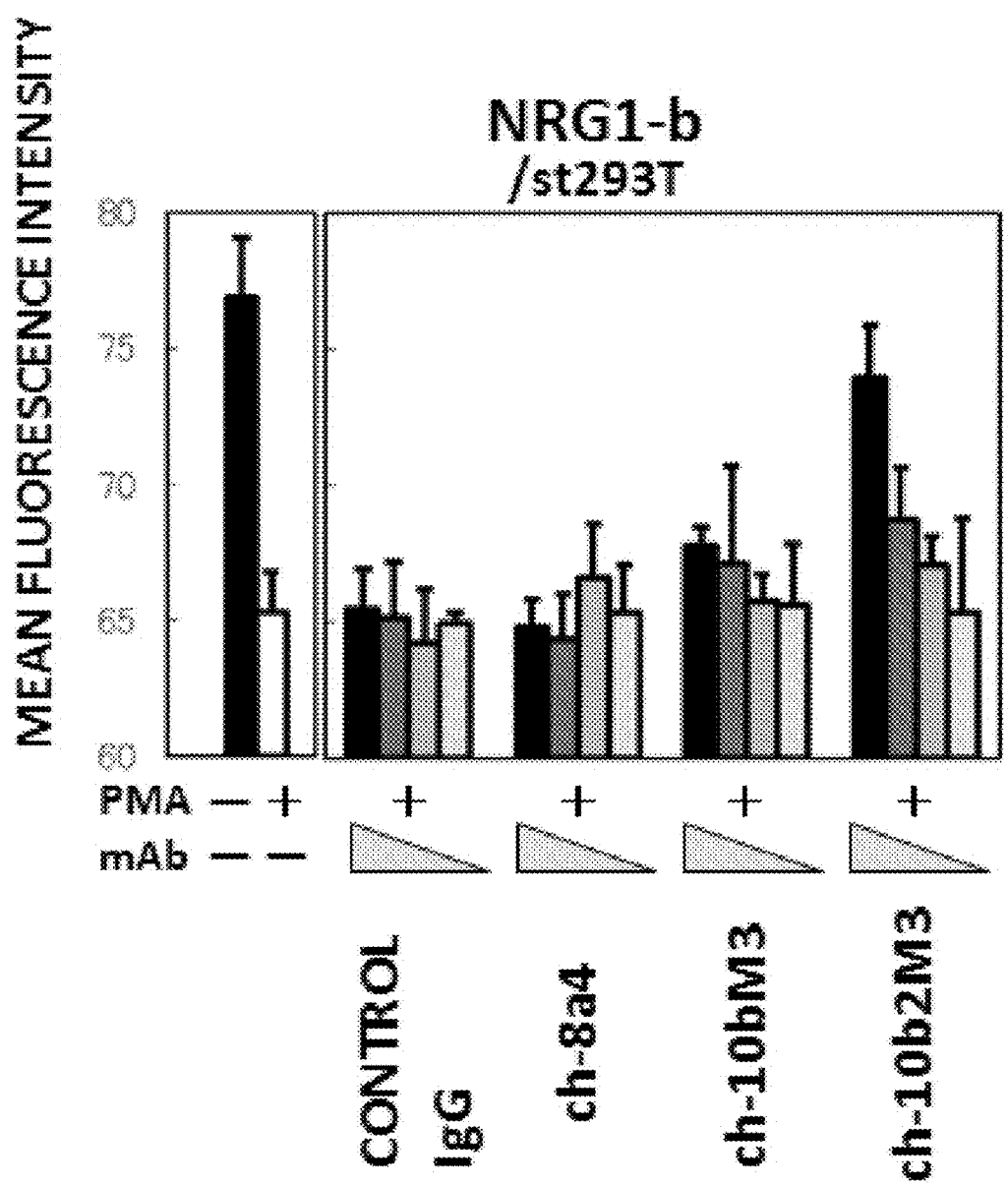
FIG. 22 is a graph for illustrating the result of analyzing by flow cytometry the chimeric antibodies of the present invention (ch-8a4, ch-10bM3, and ch-10b2M3) for the activity of suppressing the human NRG1-β1 protein cleavage that would otherwise occur by PMA.

NRG1-Cleavage Inhibitory Activities of 8a4 Chimeric Antibody, 10bM3 Chimeric Antibody, and 10b2M3 Chimeric Antibody The cleavage inhibitory activities of the chimeric antibodies prepared in Example 8 were also analyzed by the same method as above. As a result, as shown in FIGS. 21 and 22 that in terms of the fluorescence intensity in the flow cytometry in inducing the cleavage of NRG1 on the cell membrane, the chimeric antibodies exhibited the same behavior as in the above-described case of analyzing the cleavage inhibitory activities of the mouse antibodies.

Thus, it was revealed that each chimeric antibody had the same cleavage inhibitory activity as the original mouse antibody.

Example 11

Anti-Tumor Activity Evaluation Using Xenograft Mice (Early Stage Cancer Model)
To determine the anti-tumor activities of the obtained anti-NRG1 antibodies, the evaluation was performed using xenograft mice. A human lung cancer cell line ACC-LC-176

Figure 24:
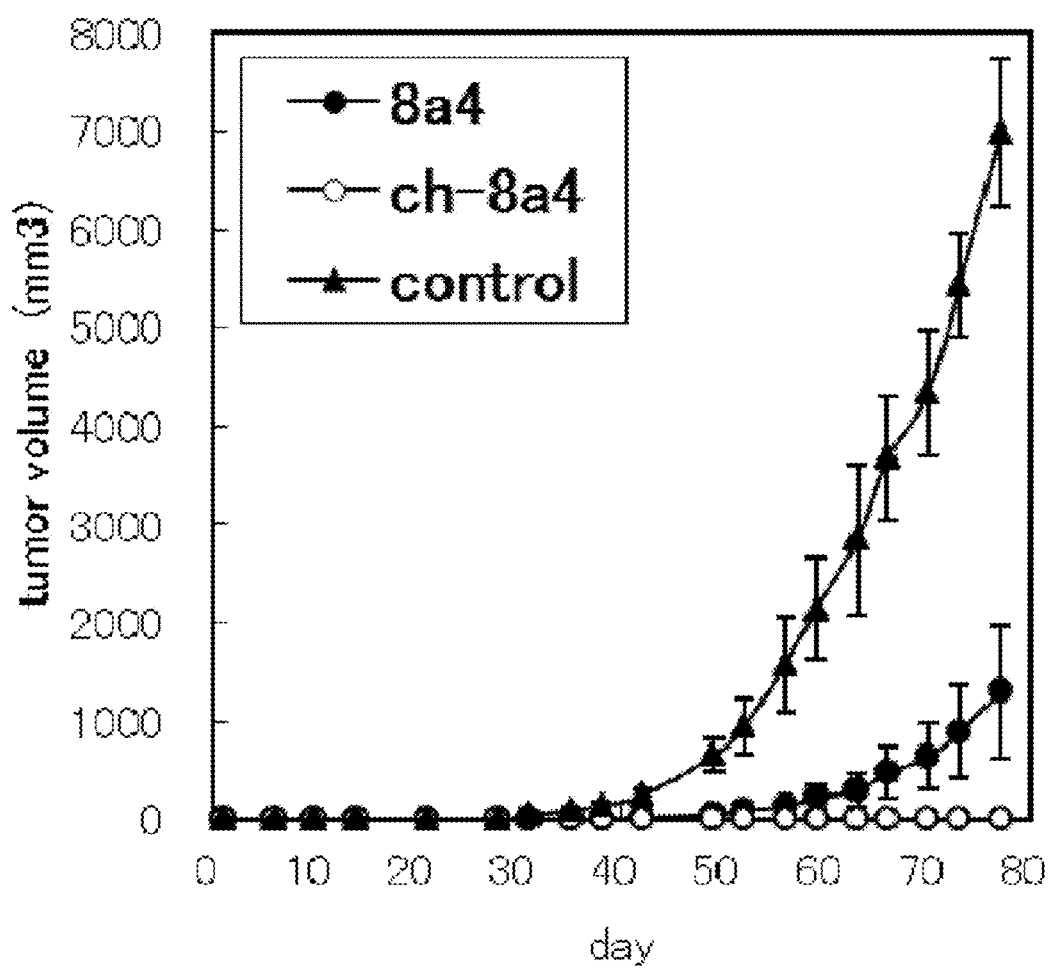
FIG. 24 is a graph for illustrating a change over time in the tumor volume in xenograft mice to which the antibody of the present invention (8a4 or ch-8a4) was administered.
Figure 25:
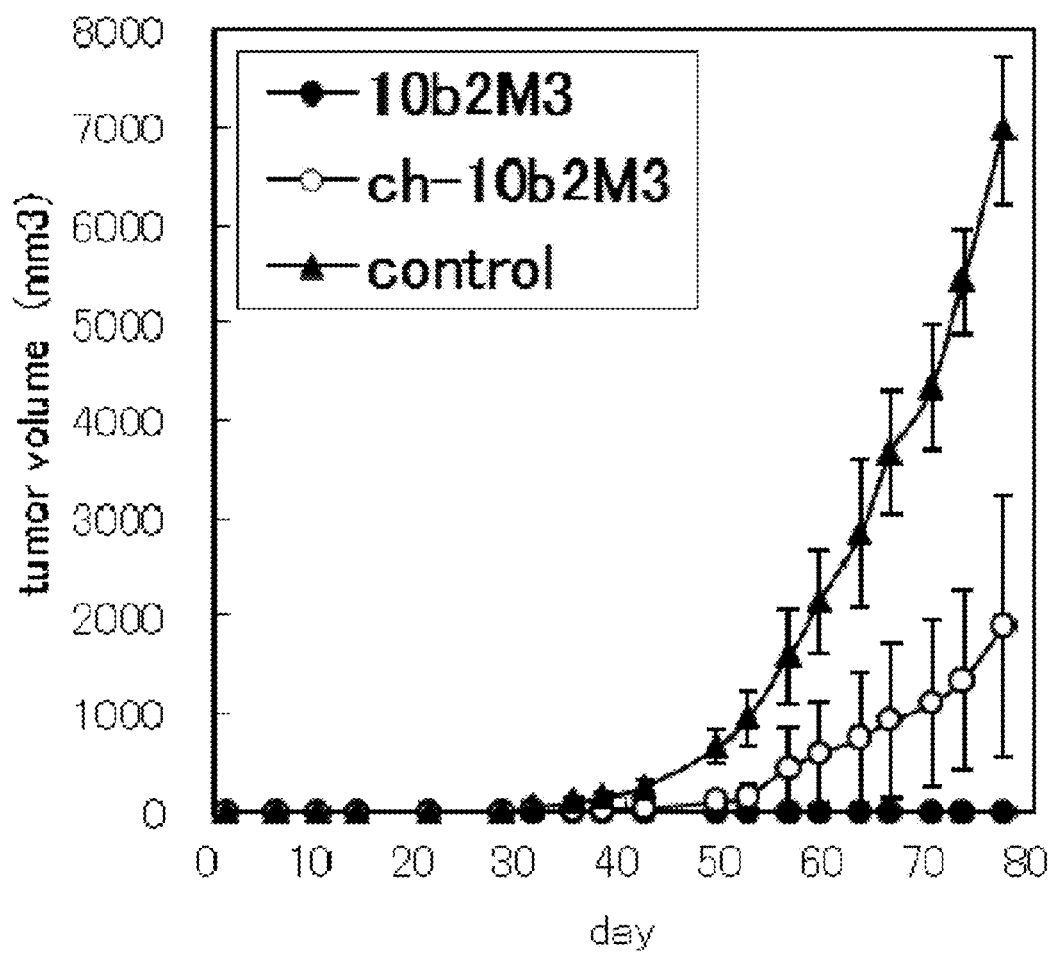
FIG. 25 is a graph for illustrating a change over time in the tumor volume in xenograft mice to which the antibody of the present invention (10b2M3 or ch-10b2M3) was administered.

(established by Takashi Takahashi et al. at Nagoya University, and received from the same university) was cultured using RPMI-10% FBS (containing Penicillin-Streptomycin), and exfoliated with a Cell Dissociation Buffer enzyme free PBS-based (manufactured by Invitrogen Corporation: 13151-014) solution to which collagenase Type I (manufactured by GIBCO Corp.: 17100-017) had been added in an amount of 2 mg/mL. After washing, the resultant was suspended in an RPMI 1640 medium to a cell count of $1 \times 10^7$/mL. An equal amount of Matrigel (manufactured by BD: 354230) was added thereto, and the mixture was suspended. Then, 200 µL of the suspension was subcutaneously transplanted into the right ventral part of each 6-week old female SCID mouse (manufactured by CLEA Japan, Inc.: C.B17/Icr-scid Jcl). From the same day, 300 µL of PBS or an antibody solution having been diluted with PBS to a concentration of 1 mg/mL was locally administered to the tumor. Five antibodies were used: 8a2, 8a4, the 8a4 chimeric antibody, 10b2M3, and the 10b2M3 chimeric antibodies. Each was administered to six mice. The administration was carried out on the day of the transplantation, Day 6, Day 10, Day 14, Day 21, and Day 28, six times in total. When the tumor was observed, the tumor diameter was measuring with a vernier caliper. The tumor volume was calculated from the following equation. Tumor volume (mm$^3$)=major axis×minor axis$^2$×0.5 FIGS. 23 to 25 show the obtained result.

Figure 26:
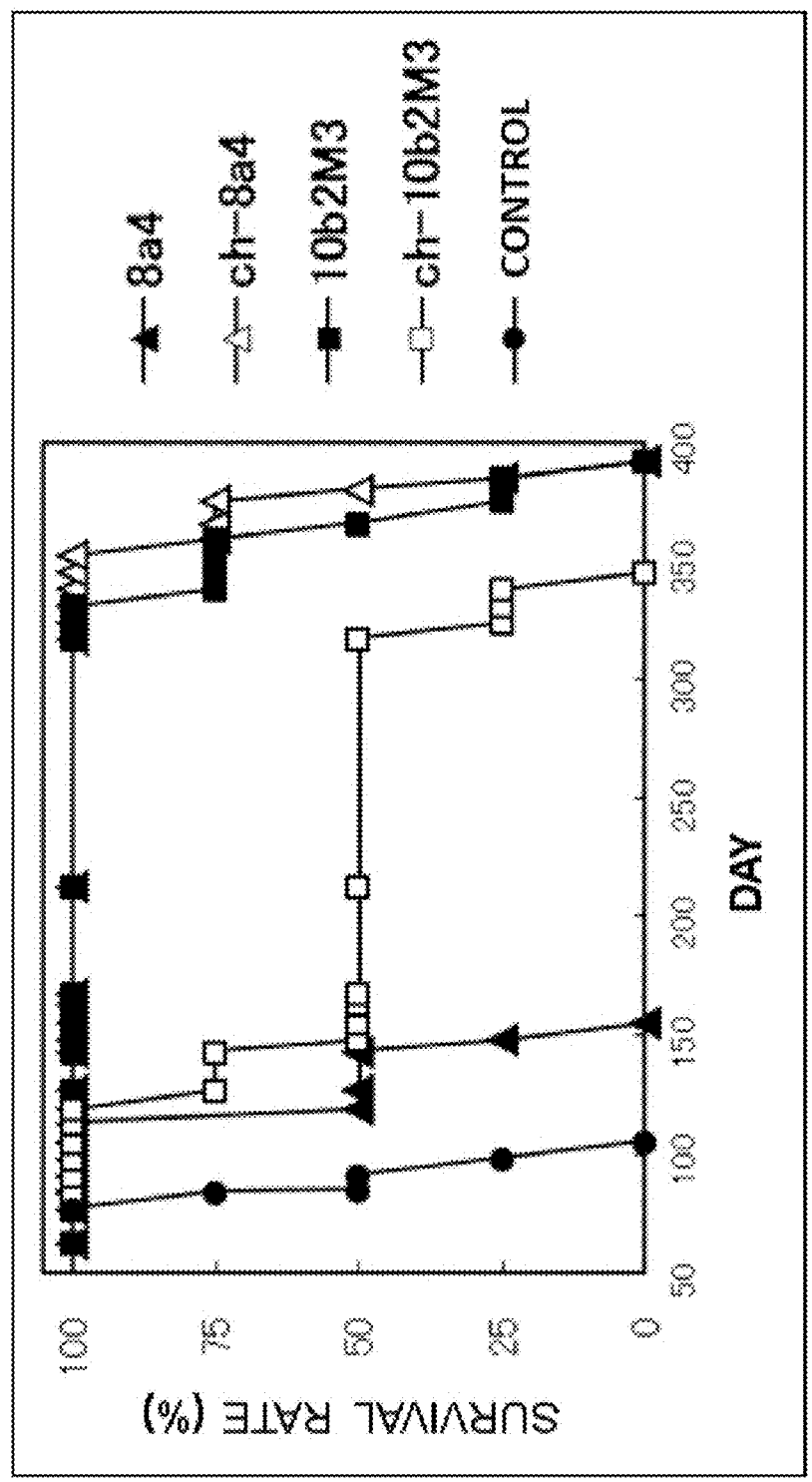
FIG. 26 is a graph for illustrating a change over time in the survival rate of the xenograft mice to which the antibody of the present invention (8a4, ch-8a4, 10b2M3, or ch-10b2M3) was administered.

Moreover, the survival rates of the xenograft mice after the antibody administration were also analyzed. FIG. 26 shows the obtained result.

Figure 23:
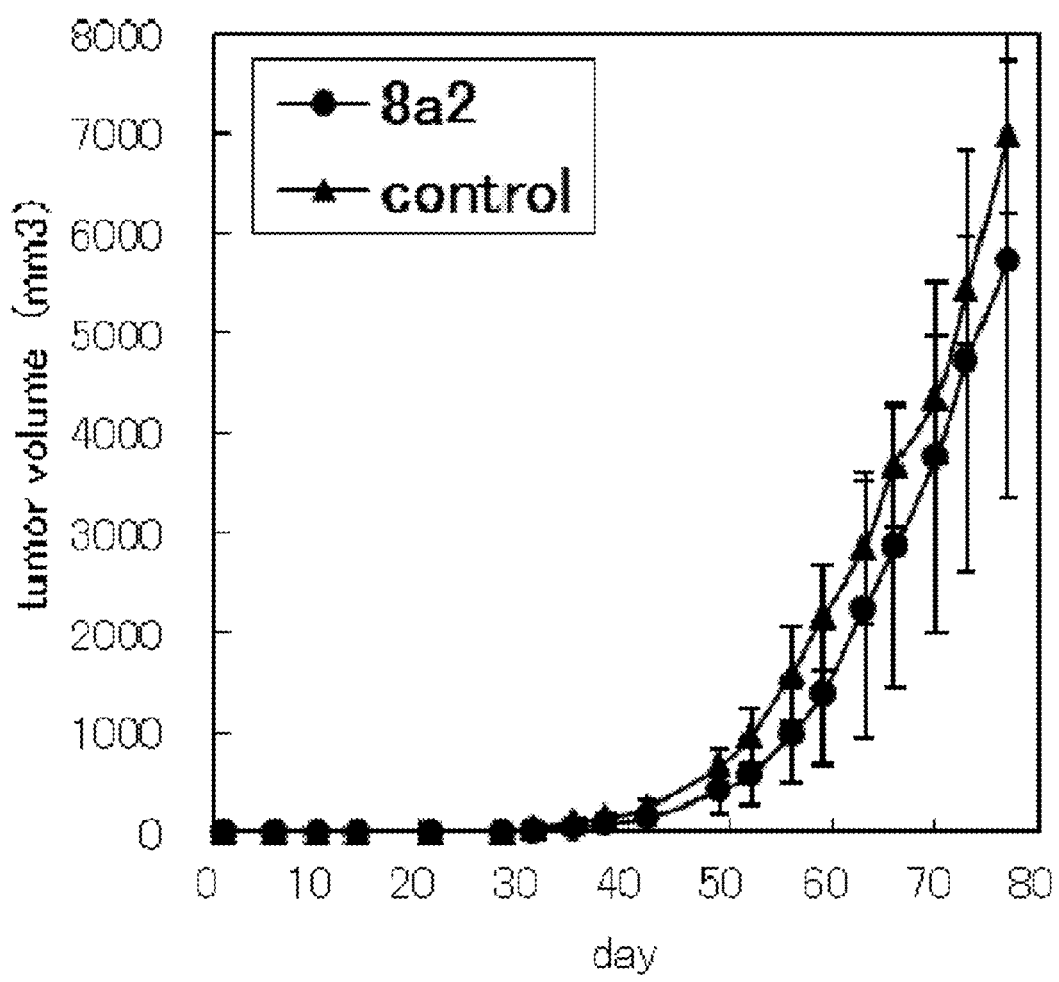
FIG. 23 is a graph for illustrating a change over time in the tumor volume in xenograft mice to which 8a2 was administered. The horizontal axis represents days elapsed after the antibody was administered, provided that the day when the administration was initiated is Day 0 (regarding the horizontal axis, the same shall apply to FIGS. 24 to 26).

As apparent from the result shown in FIG. 23, no significant difference was observed in the anti-tumor activity between the 8a2 antibody and the control antibody. On the other hand, as apparent from the results shown in FIGS. 24 and 25, the tumor volumes of the 8a4 antibody-administered group, the 10b2M3 antibody-administered group, the ch-8a4 antibody-administered group, and the ch-10b2M3 antibody-administered group were respectively 7.7%, 0%, 0%, and 16.2% of that of the control group 38 days after the transplantation; 8.3%, 0%, 0%, and 15.4% at Day 49; 19.2%, 0%, 0%, and 26.7% at Day 80 when the last observation was made. Thus, it was revealed that the anti-NRG1 antibodies of the present invention were capable of significantly inhibiting tumor increase (P<0.05).

Moreover, regarding the survival rate, as apparent from the result shown in FIG. 26, all the individuals in the control group were dead after approximately 100 days. In contrast, all the individuals in the 8a4 antibody-administered group, the 10b2M3 antibody-administered group, the ch-8a4 antibody-administered group, and the ch-10b2M3 antibody-administered group were alive even after approximately 100 days elapsed, indicating that the antibodies of the present invention exhibited a life extending effect. Particularly, 50% or more of the individuals in the ch-10b2M3 antibody-administered group, the 10b2M3 antibody-administered group, and the 8a4 antibody-administered group were alive even after 300 days elapsed. Thus, it was revealed that 8a4, 10b2M3, ch-8a4, and ch-10b2M3 had an anti-tumor effect.

INDUSTRIAL APPLICABILITY

As has been described above, the present invention makes it possible to provide an antibody capable of specifically recognizing a human NRG1 protein isoform, and suppressing signal transduction in which the isoform is involved. Moreover, the antibody of the present invention is excellent also in the activity of suppressing tumor proliferation. Therefore, the antibody of the present invention is useful also in the treatment or prevention for cancers.

SEQUENCE LISTING FREE TEXT

SEQ ID NO: 3
<223> CDR1 of Light Chain (8a4)
SEQ ID NO: 4
<223> CDR2 of Light Chain (8a4)
SEQ ID NO: 5
<223> CDR3 of Light Chain (8a4)
SEQ ID NO: 6
<223> Variable Region of Light Chain (8a4)
SEQ ID NO: 7
<223> CDR1 of Heavy Chain (8a4)
SEQ ID NO: 8
<223> CDR2 of Heavy Chain (8a4)
SEQ ID NO: 9
<223> CDR3 of Heavy Chain (8a4)
SEQ ID NO: 10
<223> Variable Region of Heavy Chain (8a4)
SEQ ID NO: 11
<223> CDR1 of Light Chain (10bM3)
SEQ ID NO: 12
<223> CDR2 of Light Chain (10bM3)
SEQ ID NO: 13
<223> CDR3 of Light Chain (10bM3)
SEQ ID NO: 14
<223> Variable Region of Light Chain (10bM3)
SEQ ID NO: 15
<223> CDR1 of Heavy Chain (10bM3)
SEQ ID NO: 16
<223> CDR2 of Heavy Chain (10bM3)
SEQ ID NO: 17
<223> CDR3 of Heavy Chain (10bM3)
SEQ ID NO: 18
<223> Variable Region of Heavy Chain (10bM3)
SEQ ID NO: 19
<223> CDR1 of Light Chain (10b2M3)
SEQ ID NO: 20
<223> CDR2 of Light Chain (10b2M3)
SEQ ID NO: 21
<223> CDR3 of Light Chain (10b2M3)
SEQ ID NO: 22
<223> Variable Region of Light Chain (10b2M3)
SEQ ID NO: 23
<223> CDR1 of Heavy Chain (10b2M3)
SEQ ID NO: 24
<223> CDR2 of Heavy Chain (10b2M3)
SEQ ID NO: 25
<223> CDR3 of Heavy Chain (10b2M3)
SEQ ID NO: 26
<223> Variable Region of Heavy Chain (10b2M3)
SEQ ID NO: 27 to 35, 37 to 51, and 54 to 67
<223> Artificially synthesized primer sequence
SEQ ID NO: 36
<223> Artificially synthesized oligonucleotide sequence

The invention claimed is:

1. An antibody capable of binding to a region between positions 221 to 234 of SEQ ID NO: 1, wherein the antibody comprises a light chain variable region containing the amino acid sequences of SEQ ID NOs: 3 to 5, and wherein the antibody further comprises a heavy chain variable region containing the amino acid sequences of SEQ ID NOs: 7 to 9.

2. An antibody capable of binding to a region between positions 221 to 234 of SEQ ID NO: 1, wherein the antibody comprises a light chain variable region which comprises the amino acid sequence of SEQ ID NO: 6, and
   wherein the antibody further comprises a heavy chain variable region which comprises the amino acid sequence of SEQ ID NO: 10.

* * * * *

SEQUENCE LISTING

<160> NUMBER OF SEQ ID NOS: 67

<210> SEQ ID NO 1
<211> LENGTH: 640
<212> TYPE: PRT
<213> ORGANISM: Homo sapiens

<400> SEQUENCE: 1

```
Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Gln Pro Gly Phe Thr Gly Ala Arg Cys Thr Glu Asn
    210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
            260                 265                 270

Lys Leu His Asp Arg Leu Arg Gln Ser Leu Arg Ser Glu Arg Asn Asn
        275                 280                 285

Met Met Asn Ile Ala Asn Gly Pro His His Pro Asn Pro Pro Pro Glu
    290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
            340                 345                 350

His Ser Trp Ser Asn Gly His Thr Glu Ser Ile Leu Ser Glu Ser His
        355                 360                 365
```

```
Ser Val Ile Val Met Ser Ser Val Glu Asn Ser Arg His Ser Ser Pro
    370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415

Asp Ser Pro His Ser Glu Arg Tyr Val Ser Ala Met Thr Thr Pro Ala
            420                 425                 430

Arg Met Ser Pro Val Asp Phe His Thr Pro Ser Ser Pro Lys Ser Pro
        435                 440                 445

Pro Ser Glu Met Ser Pro Pro Val Ser Ser Met Thr Val Ser Met Pro
450                 455                 460

Ser Met Ala Val Ser Pro Phe Met Glu Glu Arg Pro Leu Leu Leu
465                 470                 475                 480

Val Thr Pro Pro Arg Leu Arg Glu Lys Lys Phe Asp His His Pro Gln
                485                 490                 495

Gln Phe Ser Ser Phe His His Asn Pro Ala His Asp Ser Asn Ser Leu
                500                 505                 510

Pro Ala Ser Pro Leu Arg Ile Val Glu Asp Glu Glu Tyr Glu Thr Thr
            515                 520                 525

Gln Glu Tyr Glu Pro Ala Gln Glu Pro Val Lys Lys Leu Ala Asn Ser
530                 535                 540

Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
            580                 585                 590

Asn Pro Leu Ala Ala Ser Leu Glu Ala Thr Pro Ala Phe Arg Leu Ala
        595                 600                 605

Asp Ser Arg Thr Asn Pro Ala Gly Arg Phe Ser Thr Gln Glu Glu Ile
    610                 615                 620

Gln Ala Arg Leu Ser Ser Val Ile Ala Asn Gln Asp Pro Ile Ala Val
625                 630                 635                 640

<210> SEQ ID NO 2
<211> LENGTH: 645
<212> TYPE: PRT
<213> ORGANISM: Homo sapiens

<400> SEQUENCE: 2

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110
```

```
Lys Val Ile Ser Lys Leu Gly Asn Asp Ser Ala Ser Ala Asn Ile Thr
            115                 120                 125
Ile Val Glu Ser Asn Glu Ile Ile Thr Gly Met Pro Ala Ser Thr Glu
        130                 135                 140
Gly Ala Tyr Val Ser Ser Glu Ser Pro Ile Arg Ile Ser Val Ser Thr
145                 150                 155                 160
Glu Gly Ala Asn Thr Ser Ser Thr Ser Thr Ser Thr Thr Gly Thr
                165                 170                 175
Ser His Leu Val Lys Cys Ala Glu Lys Glu Lys Thr Phe Cys Val Asn
            180                 185                 190
Gly Gly Glu Cys Phe Met Val Lys Asp Leu Ser Asn Pro Ser Arg Tyr
        195                 200                 205
Leu Cys Lys Cys Pro Asn Glu Phe Thr Gly Asp Arg Cys Gln Asn Tyr
    210                 215                 220
Val Met Ala Ser Phe Tyr Lys His Leu Gly Ile Glu Phe Met Glu Ala
225                 230                 235                 240
Glu Glu Leu Tyr Gln Lys Arg Val Leu Thr Ile Thr Gly Ile Cys Ile
                245                 250                 255
Ala Leu Leu Val Val Gly Ile Met Cys Val Val Ala Tyr Cys Lys Thr
            260                 265                 270
Lys Lys Gln Arg Lys Lys Leu His Asp Arg Leu Arg Gln Ser Leu Arg
        275                 280                 285
Ser Glu Arg Asn Asn Met Met Asn Ile Ala Asn Gly Pro His His Pro
    290                 295                 300
Asn Pro Pro Pro Glu Asn Val Gln Leu Val Asn Gln Tyr Val Ser Lys
305                 310                 315                 320
Asn Val Ile Ser Ser Glu His Ile Val Glu Arg Glu Ala Glu Thr Ser
                325                 330                 335
Phe Ser Thr Ser His Tyr Thr Ser Thr Ala His His Ser Thr Thr Val
            340                 345                 350
Thr Gln Thr Pro Ser His Ser Trp Ser Asn Gly His Thr Glu Ser Ile
        355                 360                 365
Leu Ser Glu Ser His Ser Val Ile Val Met Ser Ser Val Glu Asn Ser
    370                 375                 380
Arg His Ser Ser Pro Thr Gly Gly Pro Arg Gly Arg Leu Asn Gly Thr
385                 390                 395                 400
Gly Gly Pro Arg Glu Cys Asn Ser Phe Leu Arg His Ala Arg Glu Thr
                405                 410                 415
Pro Asp Ser Tyr Arg Asp Ser Pro His Ser Glu Arg Tyr Val Ser Ala
            420                 425                 430
Met Thr Thr Pro Ala Arg Met Ser Pro Val Asp Phe His Thr Pro Ser
        435                 440                 445
Ser Pro Lys Ser Pro Pro Ser Glu Met Ser Pro Val Ser Ser Met
    450                 455                 460
Thr Val Ser Met Pro Ser Met Ala Val Ser Pro Phe Met Glu Glu Glu
465                 470                 475                 480
Arg Pro Leu Leu Leu Val Thr Pro Pro Arg Leu Arg Glu Lys Lys Phe
                485                 490                 495
Asp His His Pro Gln Gln Phe Ser Ser Phe His His Asn Pro Ala His
            500                 505                 510
Asp Ser Asn Ser Leu Pro Ala Ser Pro Leu Arg Ile Val Glu Asp Glu
        515                 520                 525
```

```
Glu Tyr Glu Thr Thr Gln Glu Tyr Glu Pro Ala Gln Glu Pro Val Lys
            530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
            595                 600                 605

Ala Phe Arg Leu Ala Asp Ser Arg Thr Asn Pro Ala Gly Arg Phe Ser
            610                 615                 620

Thr Gln Glu Glu Ile Gln Ala Arg Leu Ser Ser Val Ile Ala Asn Gln
625                 630                 635                 640

Asp Pro Ile Ala Val
                645
```

<210> SEQ ID NO 3
<211> LENGTH: 16
<212> TYPE: PRT
<213> ORGANISM: Mus musculus
<220> FEATURE:
<221> NAME/KEY: SITE
<222> LOCATION: (1)..(16)
<223> OTHER INFORMATION: CDR1 of Light Chain(8a4)

<400> SEQUENCE: 3

```
Arg Ser Ser Gln Thr Ile Val His Arg Asn Gly Asn Thr Tyr Leu Glu
1               5                   10                  15
```

<210> SEQ ID NO 4
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain(8a4)

<400> SEQUENCE: 4

```
Arg Val Ser Asn Arg Phe Ser
1               5
```

<210> SEQ ID NO 5
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Light Chain(8a4)

<400> SEQUENCE: 5

```
Phe Gln Gly Ser His Val Pro Leu Thr
1               5
```

<210> SEQ ID NO 6
<211> LENGTH: 109
<212> TYPE: PRT
<213> ORGANISM: Mus musculus
<220> FEATURE:
<221> NAME/KEY: SITE
<222> LOCATION: (1)..(109)
<223> OTHER INFORMATION: Variable Region of Light Chain(8a4)

-continued

```
<400> SEQUENCE: 6

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu
            100                 105

<210> SEQ ID NO 7
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain(8a4)

<400> SEQUENCE: 7

Asp Asp Tyr Ile His
1               5

<210> SEQ ID NO 8
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain(8a4)

<400> SEQUENCE: 8

Trp Ile Asp Pro Glu Asn Gly Asp Thr Glu Tyr Ala Ser Gln Phe Gln
1               5                   10                  15

Gly

<210> SEQ ID NO 9
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Heavy Chain(8a4)

<400> SEQUENCE: 9

Ser Asp His Arg Ala Trp Phe Ala Phe
1               5

<210> SEQ ID NO 10
<211> LENGTH: 118
<212> TYPE: PRT
<213> ORGANISM: Mus musculus
<220> FEATURE:
<221> NAME/KEY: SITE
<222> LOCATION: (1)..(118)
<223> OTHER INFORMATION: Variable Region of Heavy Chain(8a4)
```

```
<400> SEQUENCE: 10

Glu Val Gln Leu Gln Gln Ser Gly Ala Asp Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Thr Tyr Ala Ser Gln Phe
    50                  55                  60

Gln Gly Lys Ala Thr Ile Thr Ala Asp Thr Ser Ser Asn Thr Ala Tyr
65                  70                  75                  80

Leu Gln Leu Arg Ser Leu Thr Ser Glu Asp Thr Ala Val Tyr Tyr Cys
                85                  90                  95

Thr Thr Ser Asp His Arg Ala Trp Phe Ala Phe Trp Gly Leu Gly Thr
                100                 105                 110

Leu Val Thr Val Ser Ser
            115

<210> SEQ ID NO 11
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR1 of Light Chain(10bM3)

<400> SEQUENCE: 11

Lys Ser Ser Gln Ser Leu Leu Trp Ser Val Asn Gln Lys Asn Tyr Leu
1               5                   10                  15

Ser

<210> SEQ ID NO 12
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain(10bM3)

<400> SEQUENCE: 12

Gly Ala Ser Ile Arg Glu Ser
1               5

<210> SEQ ID NO 13
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: CDR3 of Light Chain(10bM3)

<400> SEQUENCE: 13

Gln His Asn His Gly Arg Phe Leu Pro Leu Thr
1               5                   10

<210> SEQ ID NO 14
<211> LENGTH: 112
<212> TYPE: PRT
<213> ORGANISM: Mus musculus
```

```
<220> FEATURE:
<221> NAME/KEY: SITE
<222> LOCATION: (1)..(112)
<223> OTHER INFORMATION: Variable Region of Light Chain(10bM3)

<400> SEQUENCE: 14

Asp Ile Val Met Thr Gln Ser Pro Ser Ser Leu Ala Val Thr Ala Gly
1               5                   10                  15

Glu Lys Val Thr Met Arg Cys Lys Ser Ser Gln Ser Leu Leu Trp Ser
            20                  25                  30

Val Asn Gln Lys Asn Tyr Leu Ser Trp Tyr Gln Gln Lys Glu Gly Gln
        35                  40                  45

Ser Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Ser Asn Val His Ala Glu Asp Leu Ala Val Tyr Tyr Cys Gln His
                85                  90                  95

Asn His Gly Arg Phe Leu Pro Leu Thr Phe Gly Gly Gly Thr Lys Leu
            100                 105                 110

<210> SEQ ID NO 15
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain(10bM3)

<400> SEQUENCE: 15

Asp Tyr Gly Ile His
1               5

<210> SEQ ID NO 16
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain(10bM3)

<400> SEQUENCE: 16

Tyr Ile Ser Ser Gly Ser Ser Thr Ile Tyr Tyr Ala Asp Thr Val Lys
1               5                   10                  15

Gly

<210> SEQ ID NO 17
<211> LENGTH: 12
<212> TYPE: PRT
<213> ORGANISM: Mus musculus
<220> FEATURE:
<221> NAME/KEY: SITE
<222> LOCATION: (1)..(12)
<223> OTHER INFORMATION: CDR3 of Heavy Chain(10bM3)

<400> SEQUENCE: 17

Gly Ser Asn Tyr Val Gly Tyr Tyr Ala Met Asp Tyr
1               5                   10
```

-continued

```
<210> SEQ ID NO 18
<211> LENGTH: 121
<212> TYPE: PRT
<213> ORGANISM: Mus musculus
<220> FEATURE:
<221> NAME/KEY: SITE
<222> LOCATION: (1)..(121)
<223> OTHER INFORMATION: Variable Region of Heavy Chain(10bM3)

<400> SEQUENCE: 18

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asp Tyr
            20                  25                  30

Gly Ile His Trp Val Arg Gln Ala Pro Glu Lys Gly Leu Glu Trp Leu
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Ser Asn Tyr Val Gly Tyr Tyr Ala Met Asp Tyr Trp Gly
            100                 105                 110

Gln Gly Thr Ser Val Thr Val Ser Ser
        115                 120

<210> SEQ ID NO 19
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR1 of Light Chain(10b2M3)

<400> SEQUENCE: 19

Lys Ser Ser Gln Ser Leu Leu Ala Ser Ala Asn Gln Asn Asn Tyr Leu
1               5                   10                  15

Ala

<210> SEQ ID NO 20
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: CDR2 of Light Chain(10b2M3)

<400> SEQUENCE: 20

Trp Ala Ser Thr Arg Val Ser
1               5

<210> SEQ ID NO 21
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Light Chain(10b2M3)
```

<400> SEQUENCE: 21

Gln Gln Ser Tyr Ser Ala Pro Thr Thr
1               5

<210> SEQ ID NO 22
<211> LENGTH: 110
<212> TYPE: PRT
<213> ORGANISM: Mus musculus
<220> FEATURE:
<221> NAME/KEY: SITE
<222> LOCATION: (1)..(110)
<223> OTHER INFORMATION: Variable Region of Light Chain(10b2M3)

<400> SEQUENCE: 22

Asp Ile Leu Met Thr Gln Ser Pro Ser Ser Leu Thr Val Ser Thr Gly
1               5                   10                  15

Glu Lys Val Thr Met Ser Cys Lys Ser Ser Gln Ser Leu Leu Ala Ser
            20                  25                  30

Ala Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Thr Thr Phe Gly Ala Gly Thr Lys Leu
            100                 105                 110

<210> SEQ ID NO 23
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: CDR1 of Heavy Chain(10b2M3)

<400> SEQUENCE: 23

Ser Ser Trp Met Asn
1               5

<210> SEQ ID NO 24
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: CDR2 of Heavy Chain(10b2M3)

<400> SEQUENCE: 24

Arg Ile Tyr Pro Gly Asp Gly Asp Ile Tyr Tyr Asn Gly Lys Phe Lys
1               5                   10                  15

Gly

<210> SEQ ID NO 25
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: CDR3 of Heavy Chain(10b2M3)

<400> SEQUENCE: 25

Thr Phe Asn Tyr Pro Phe Phe Ala Tyr
1               5

<210> SEQ ID NO 26
<211> LENGTH: 118
<212> TYPE: PRT
<213> ORGANISM: Mus musculus
<220> FEATURE:
<221> NAME/KEY: SITE
<222> LOCATION: (1)..(118)
<223> OTHER INFORMATION: Variable Region of Heavy Chain(10b2M3)

<400> SEQUENCE: 26

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Ile Tyr Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Thr Phe Asn Tyr Pro Phe Phe Ala Tyr Trp Gly Gln Gly Thr
            100                 105                 110

Leu Val Thr Val Ser Ser
        115

<210> SEQ ID NO 27
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 27
cttggaccaa actcgcctgc g                                           21

<210> SEQ ID NO 28
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 28
ataaagtttt acaggtgaat ctatgtg                                     27

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 29
gtagagcgct ccgtctccgg                                             20

```
<210> SEQ ID NO 30
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 30
ggttttatac agcaataggg tcttg                                          25

<210> SEQ ID NO 31
<211> LENGTH: 51
<212> TYPE: DNA
<213> ORGANISM: Artificial Sequence
<220> FEATURE:
<223> OTHER INFORMATION: Artificially synthesized primer sequence

<400> SEQUENCE: 31
catcttggga ttgaatttat ggaggcggag gagctgtacc agaagagagt g              51

<210> SEQ ID NO 32
<211> LENGTH: 56
<212> TYPE: DNA
<213> ORGANISM: Artificial Sequence
<220> FEATURE:
<223> OTHER INFORMATION: Artificially synthesized primer sequence

<400> SEQUENCE: 32
ctccataaat tcaatcccaa gatgcttgta gaagctggcc attacgtagt tttggc         56

<210> SEQ ID NO 33
<211> LENGTH: 43
<212> TYPE: DNA
<213> ORGANISM: Artificial Sequence
<220> FEATURE:
<223> OTHER INFORMATION: Artificially synthesized primer sequence

<400> SEQUENCE: 33
tatgatgtgc cggattatgc ctccgagcgc aaagaaggca gag                       43

<210> SEQ ID NO 34
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 34
cgggatccta cagcaatagg gtcttggtta g                                    31

<210> SEQ ID NO 35
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 35
aatagcggcc gcaccatgcc ttatgatgtg ccggattatg cc                        42

<210> SEQ ID NO 36
<211> LENGTH: 60
<212> TYPE: DNA
<213> ORGANISM: Artificial Sequence
<220> FEATURE:
<223> OTHER INFORMATION: Artificially synthesized oligonucleotide
      sequence
```

```
<400> SEQUENCE: 36
atggagacag acacactcct gctatgggta ctgctgctct gggttccagg ttccactggt    60

<210> SEQ ID NO 37
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 37
aatagcggcc gcaaaatgtg cggagaagga gaaaac                              36

<210> SEQ ID NO 38
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 38
cgggatccag tacatcttgc tccagtg                                        27

<210> SEQ ID NO 39
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 39
aatagcggcc gcaaaatgtg cggagaagga gaaaac                              36

<210> SEQ ID NO 40
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 40
cgggatcctt ggcagcgatc accagtaaac tcat                                34

<210> SEQ ID NO 41
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 41
cgggtaccca ctctcttctg gtacagctc                                      29

<210> SEQ ID NO 42
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 42
cgggatccat gtccgagcgc aaagaagg                                       28
```

```
<210> SEQ ID NO 43
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 43
acgcgtcgac cactctcttc tggtacagct c                              31

<210> SEQ ID NO 44
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 44
cgggatccac cactgggaca agcc                                      24

<210> SEQ ID NO 45
<211> LENGTH: 29
<212> TYPE: DNA
<213> ORGANISM: Artificial
<220> FEATURE:
<223> OTHER INFORMATION: Artificially synthesized primer sequence

<400> SEQUENCE: 45
acgcgtcgac cgcctttcct tggttttgg                                 29

<210> SEQ ID NO 46
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 46
acgcgtcgac cgcctccata aattcaatcc                                30

<210> SEQ ID NO 47
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 47
cgggatcctg ccaacctgga ttcactgg                                  28

<210> SEQ ID NO 48
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 48
ccgctcgagc tacgcctttt cttggttttg g                              31

<210> SEQ ID NO 49
<211> LENGTH: 30
<212> TYPE: DNA
<213> ORGANISM: Artificial Sequence
<220> FEATURE:
<223> OTHER INFORMATION: Artificially synthesized primer sequence
```

```
<400> SEQUENCE: 49
cgggatcctg cccaaatgag tttactggtg                                    30

<210> SEQ ID NO 50
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 50
ccgctcgagc tacgcctcca taaattcaat cc                                 32

<210> SEQ ID NO 51
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 51
ccgctcgagc tacactctct tctggtacag ctc                                33

<210> SEQ ID NO 52
<211> LENGTH: 24
<212> TYPE: PRT
<213> ORGANISM: Homo sapiens

<400> SEQUENCE: 52

Cys Thr Glu Asn Val Pro Met Lys Val Gln Asn Gln Glu Lys Ala Glu
1               5                   10                  15

Glu Leu Tyr Gln Lys Arg Val Leu
            20

<210> SEQ ID NO 53
<211> LENGTH: 29
<212> TYPE: PRT
<213> ORGANISM: Homo sapiens

<400> SEQUENCE: 53

Cys Gln Asn Tyr Val Met Ala Ser Phe Tyr Lys His Leu Gly Ile Glu
1               5                   10                  15

Phe Met Glu Ala Glu Glu Leu Tyr Gln Lys Arg Val Leu
            20                  25

<210> SEQ ID NO 54
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 54
cgactggagc acgaggacac tga                                           23

<210> SEQ ID NO 55
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 55
aattttcttg tccacctgg                                                19
```

```
<210> SEQ ID NO 56
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 56
ctaacactca ttcctgttga agctct                                             26

<210> SEQ ID NO 57
<211> LENGTH: 95
<212> TYPE: DNA
<213> ORGANISM: Artificial Sequence
<220> FEATURE:
<223> OTHER INFORMATION: Artificially synthesized primer sequence

<400> SEQUENCE: 57
atataaagct taccatggaa tggagctggg tgttcctgtt ctttctgtcc gtgaccacag         60
gcgtgcattc tgaggttcag ctgcagcagt ctggg                                   95

<210> SEQ ID NO 58
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 58
atatactcga gacagtgacc agagtcccta ggcc                                    34

<210> SEQ ID NO 59
<211> LENGTH: 104
<212> TYPE: DNA
<213> ORGANISM: Artificial Sequence
<220> FEATURE:
<223> OTHER INFORMATION: Artificially synthesized primer sequence

<400> SEQUENCE: 59
atataaagct taccatgtct gtgcctaccc aggtgctggg actgctgctg ctgtggctga         60
cagacgcccg ctgtgatgtt ttgatgaccc aaactccact ctcc                        104

<210> SEQ ID NO 60
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 60
atatacgtac gttttatttc cagcttggtc ccagcaccga ac                           42

<210> SEQ ID NO 61
<211> LENGTH: 95
<212> TYPE: DNA
<213> ORGANISM: Artificial Sequence
<220> FEATURE:
<223> OTHER INFORMATION: Artificially synthesized primer sequence

<400> SEQUENCE: 61
atataaagct taccatggaa tggagctggg tgttcctgtt ctttctgtcc gtgaccacag         60
gcgtgcattc tgaggtgcag ctggtggagt ctggg                                   95
```

```
<210> SEQ ID NO 62
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 62
atatactcga gacggtgact gaggttcctt gacc                                    34

<210> SEQ ID NO 63
<211> LENGTH: 97
<212> TYPE: DNA
<213> ORGANISM: Artificial Sequence
<220> FEATURE:
<223> OTHER INFORMATION: Artificially synthesized primer sequence

<400> SEQUENCE: 63
atataaagct taccatgtct gtgcctaccc aggtgctggg actgctgctg ctgtggctga        60
cagacgcccg ctgtgacatt gtgatgaccc agtctcc                                 97

<210> SEQ ID NO 64
<211> LENGTH: 38
<212> TYPE: DNA
<213> ORGANISM: Artificial Sequence
<220> FEATURE:
<223> OTHER INFORMATION: Artificially synthesized primer sequence

<400> SEQUENCE: 64
atatacgtac gttttagctc caacttggtc ccaccacc                                38

<210> SEQ ID NO 65
<211> LENGTH: 94
<212> TYPE: DNA
<213> ORGANISM: Artificial Sequence
<220> FEATURE:
<223> OTHER INFORMATION: Artificially synthesized primer sequence

<400> SEQUENCE: 65
atataaagct taccatggaa tggagctggg tgttcctgtt ctttctgtcc gtgaccacag        60
gcgtgcattc tcaggttcag ctgcagcagt ctgg                                    94

<210> SEQ ID NO 66
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 66
tagcgctcga gacagtgacc agagt                                              25

<210> SEQ ID NO 67
<211> LENGTH: 97
<212> TYPE: DNA
<213> ORGANISM: Artificial Sequence
<220> FEATURE:
<223> OTHER INFORMATION: Artificially synthesized primer sequence

<400> SEQUENCE: 67
atataaagct taccatgtct gtgcctaccc aggtgctggg actgctgctg ctgtggctga        60
cagacgcccg ctgtgacatt ttgatgactc agtctcc                                 97
```